US012606508B2

(12) United States Patent
Linciano et al.

(10) Patent No.: US 12,606,508 B2
(45) Date of Patent: Apr. 21, 2026

(54) CANNABIS EXTRACTS AND USES THEREOF

(71) Applicants: CONSIGLIO NAZIONALE DELLE RICERCHE, Rome (IT); Universita' degli Studi di Modena e Reggio Emilia, Modena (IT); SAPIENZA UNIVERSITÀ DI ROMA, Rome (IT)

(72) Inventors: Pasquale Linciano, Modena (IT); Cinzia Citti, Lecce (IT); Fabiana Russo, Modena (IT); Livio Luongo, Rome (IT); Monica Iannotta, Rome (IT); Carmela Belardo, Rome (IT); Sabatino Maione, Rome (IT); Maria Angela Vandelli, Modena (IT); Flavio Forni, Modena (IT); Giuseppe Gigli, Modena (IT); Aldo Laganá, Rome (IT); Anna Laura Capriotti, Rome (IT); Carmela Maria Montone, Rome (IT); Giuseppe Cannazza, Modena (IT)

(73) Assignees: CONSIGLIO NAZIONALE DELLE RICERCHE, Rome (IT); Universita' degli Studi di Modena e Reggio Emilia, Modena (IT); SAPIENZA UNIVERSITÀ DI ROMA, Rome (IT)

( * ) Notice: Subject to any disclaimer, the term of this patent is extended or adjusted under 35 U.S.C. 154(b) by 33 days.

(21) Appl. No.: 18/516,260

(22) Filed: Nov. 21, 2023

(65) Prior Publication Data

US 2024/0109830 A1 Apr. 4, 2024

Related U.S. Application Data

(63) Continuation of application No. 17/371,941, filed on Jul. 9, 2021, now abandoned.

(60) Provisional application No. 63/050,240, filed on Jul. 10, 2020.

(51) Int. Cl.
*C07C 37/11* (2006.01)
*C07C 39/23* (2006.01)
*C07D 311/80* (2006.01)

(52) U.S. Cl.
CPC .............. *C07C 37/11* (2013.01); *C07C 39/23* (2013.01); *C07D 311/80* (2013.01)

(58) Field of Classification Search
CPC ....................................................... C07C 37/11
See application file for complete search history.

(56) References Cited

U.S. PATENT DOCUMENTS 10,941,131 B1 * 3/2021 Grondin ............... C07D 311/80
2014/0271940 A1 9/2014 Wurzer

FOREIGN PATENT DOCUMENTS

GB 2478595 A * 9/2011 ............. A61P 35/00

OTHER PUBLICATIONS

Papahatjis et al., "C1¢-Cycloalkyl Side Chain Pharmacophore in Tetrahydrocannabinols", J. Med. Chem., 2007 (Year: 2007).*

(Continued)

*Primary Examiner* — Andrew D Kosar
*Assistant Examiner* — Gillian A Hutter
(74) *Attorney, Agent, or Firm* — Silvia Salvadori, P.C.; Silvia Salvadori

(57) ABSTRACT

The present disclosure concerns a group of cannabinoid compounds defined by formulas (I) to (IV), wherein $R_1$ is —H or —COOH, for the first time isolated and fully characterized in structure, absolute stereochemistry by the present applicant. Methods of isolation, characterization, stereoselective synthesis, biological activity, pharmaceutical composition and therapeutic applications of the present compounds as modulators of the cannabinoid CB1 receptor are also object of the disclosure.

(I)

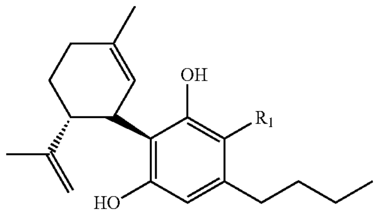

(II0

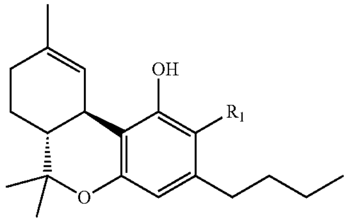

(III)

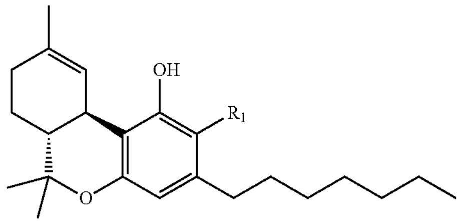

12 Claims, 39 Drawing Sheets

(56) References Cited

OTHER PUBLICATIONS

Linciano et al., "Isolation of a High-Affinity Cannabinoid for the Human CB1 Receptor from a Medicinal Cannabis sativa Variety", Journal of Natural Products, Dec. 31, 2019 (Year: 2019).*
"41233-93-6 (Potassium 2-Methyl-2-Butoxide) Product Description", Chemical Book, Dec. 11, 2017 (Year: 2017).*
"Delta 9-THCB", Cayman Chemical, Aug. 9, 2016 (Year: 2016).*
Papahtjis D et al., "C1'-cycloalkyl side chain pharmacore in tetrahydrocannabinols", J Med Chem 2007, 50, 4048-4060.

* cited by examiner

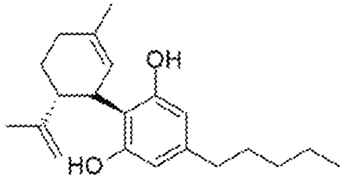

5'-methyl-4-pentyl-2'-(prop-1-en-2-yl)-1',2',3',4'-tetrahydro-[1,1'-biphenyl]-2,6-diol, Cannabidiol (CBD)

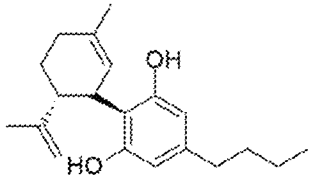

4-butyl-5'-methyl-2'-(prop-1-en-2-yl)-1',2',3',4'-tetrahydro-[1,1'-biphenyl]-2,6-diol, Cannabidibutol (CBDB)

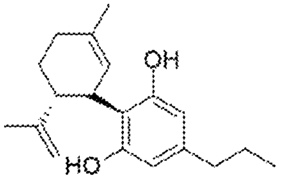

5'-methyl-2'-(prop-1-en-2-yl)-4-propyl-1',2',3',4'-tetrahydro-[1,1'-biphenyl]-2,6-diol, Cannabidivarin (CBDV)

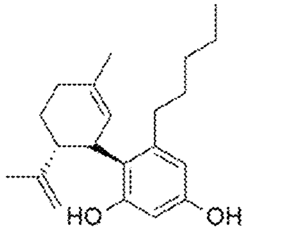

5'-methyl-6-pentyl-2'-(prop-1-en-2-yl)-1',2',3',4'-tetrahydro-[1,1'-biphenyl]-2,4-diol, abnormal CBD (*abn*-CBD)
1

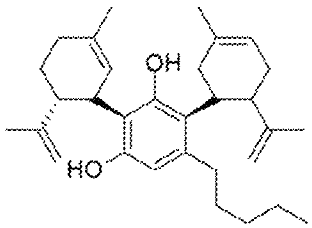

5,5''-dimethyl-6'-pentyl-2,2''-di(prop-1-en-2-yl)-1,1'',2,2'',3,3'',4'',6-octahydro-[1,1':3',1''-terphenyl]-2',4'-diol
2

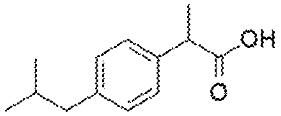

2-(4-isobutylphenyl)propanoic acid, Ibuprofen (IS)

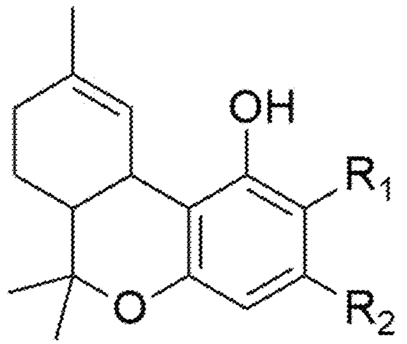
THC: $R_1$=H, $R_2$=$C_5H_{11}$
THCB: $R_1$=H, $R_2$=$C_4H_9$
THCV: $R_1$=H, $R_2$=$C_3H_7$
THCA: $R_1$=COOH, $R_2$=$C_5H_{11}$
THCBA: $R_1$=COOH, $R_2$=$C_4H_9$
THCVA: $R_1$=COOH, $R_2$=$C_3H_7$
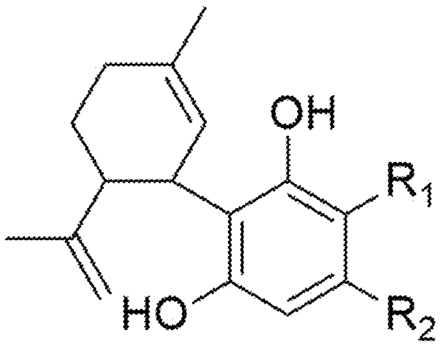
CBD: $R_1$=H, $R_2$=$C_5H_{11}$
CBDB: $R_1$=H, $R_2$=$C_4H_9$
CBDV: $R_1$=H, $R_2$=$C_3H_7$
CBDA: $R_1$=COOH, $R_2$=$C_5H_{11}$
CBDBA: $R_1$=COOH, $R_2$=$C_4H_9$
CBDVA: $R_1$=COOH, $R_2$=$C_3H_7$
Figure 11 a

| | R | hCB1 $K_i$ (nM) | hCB2 $K_i$ (nM) |
|---|---|---|---|
| (−)-*trans*-$\Delta^9$-THCV | -propyl | 75.4 | 62.8 |
| (−)-*trans*-$\Delta^9$-THCB | -butyl | 15 | 51 |
| (−)-*trans*-$\Delta^9$-THC | -pentyl | 40 | 36 |
| (−)-*trans*-$\Delta^9$-THCP | -heptyl | 1.2 | 6.2 |

CANNABIS EXTRACTS AND USES THEREOF

This Non-Provisional Application is a continuation application of U.S. Non-Provisional application Ser. No. 17/371,941, filed Jul. 9, 2021, which claims priority to and the benefit of U.S. Provisional Application Ser. No. 63/050,240 filed Jul. 10, 2020, the content of which are incorporated herein by reference in its in their entireties.

TECHNICAL FIELD

The present disclosure relates generally to *cannabis* extracts, in particular cannabinoid compounds derived from these extracts and related uses thereof.

BACKGROUND

What is needed are *cannabis* extracts and compounds derived from *cannabis* and related uses thereof.

SUMMARY

The present invention concerns a group of cannabinoid compounds for the first time isolated and fully characterized in structure, absolute stereochemistry by the present applicant; the biological activity of these compounds and their possible therapeutic applications are also experimentally investigated and disclosed herein.

The compounds object of the present invention are selected from the group consisting of:

| | | |
|---|---|---|
| (−)trans (1R,6R) cannabidibutol | [CBDB] | of formula (I), |
| (−)trans (1R,6R) $\Delta^9$ tetrahydrocannabutol | [$\Delta^9$ THCB] | of formula (II), |
| (−)trans (1R,6R) $\Delta^9$ tetrahydro-cannabiphorol | [$\Delta^9$ THCP] | of formula (III), |
| (−)trans (1R,6R) cannabidiphorol | [CBDP] | of formula (IV) |

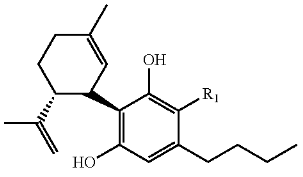

(I)

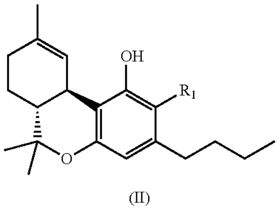

(II)

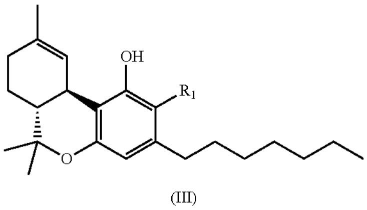

(III)

-continued

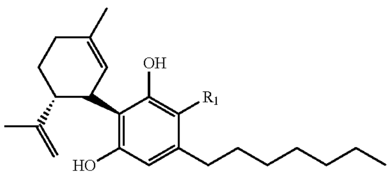

(IV)

wherein $R_1$ is —H.

The invention also includes the corresponding acid derivatives:

| | | |
|---|---|---|
| (−)trans (1R,6R) cannabidibutolic acid | [CBDBA] | of formula (I), |
| (−)trans (1R,6R) $\Delta^9$ tetrahydrocannabutolic acid | [$\Delta^9$ THCBA] | of formula (II), |
| (−)trans (1R,6R) $\Delta^9$ tetrahydrocannabiphorolic acid | [$\Delta^9$ THCPA] | of formula (III), |
| (−)trans (1R,6R) cannabidiphorolic acid | [CBDPA] | of formula (IV), |

wherein $R_1$ is —COOH.

Prior to the present invention, some of the compounds of formulas (I) to (IV) might have been partially described in their structure, while others were never described nor characterized at all; moreover, the biological activity and therapeutic potential for each of the present compounds, expressed as binding affinity to the cannabinoid CB1 receptor, was never investigated prior to this invention.

The compounds of formulas (I) to (IV) occur in small amounts in nature and can be isolated form hemp (*Cannabis sativa* L.), in particular from hemp cannabinoid active agents (CBD) and $\Delta^9$ tetrahydrocannabinol ($\Delta^9$ THC, or simply THC), wherein they may generally occur is small amounts as impurities. Non-limitative procedures for the isolation of the compounds of formulas (I) to (IV) from their natural sources are illustrated in the experimental part of this application.

The present invention is also directed to methods for the stereoselective synthesis of the compounds of formulas (I) to (IV). The so-obtained products have been used herein to confirm, by comparison, the full stereochemistry of their corresponding natural counterparts; however, the invention is not limited to this use and the synthetic stereoselective procedures disclosed herein can be used in general to manufacture the present compounds of formulas (I) to (IV) for any purposes, in particular for industrial production, in alternative to their extraction from hemp or hemp cannabinoids. The present synthetic methods also make available, for the first time in enabling way, the corresponding compounds with their complete stereochemical configuration.

The method to produce the cannabinoid compound CBDB of formula (I) comprises reacting (1S,4R)-1-methyl-4-(prop-1-en-2-yl)cycloex-2-enol with 5-butylbenzene-1,3-diol according to scheme (I) in presence of an acidic catalyst, obtaining CBDB.

Scheme (I)

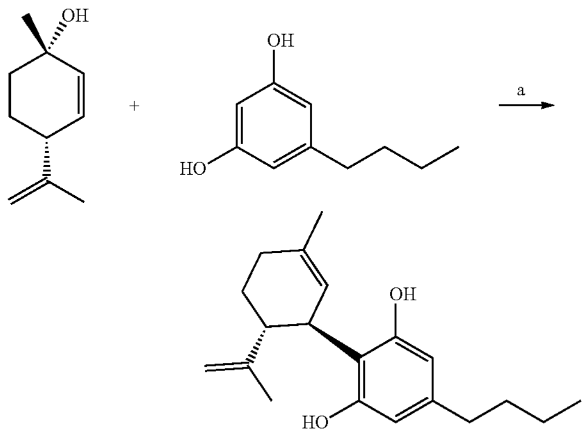

The above reaction (Friedel-Craft allylation) can be applied likewise to the production of the cannabinoid compound CBDP of formula (IV), with the difference that the compound to be reacted with (1S,4R)-1-methyl-4-(prop-1-en-2-yl)cycloex-2-enol is 5-heptylbenzene-1,3-diol according to the following scheme (II); the reaction is also performed in presence of an acidic catalyst, obtaining in this case CBDP.

Scheme (II)

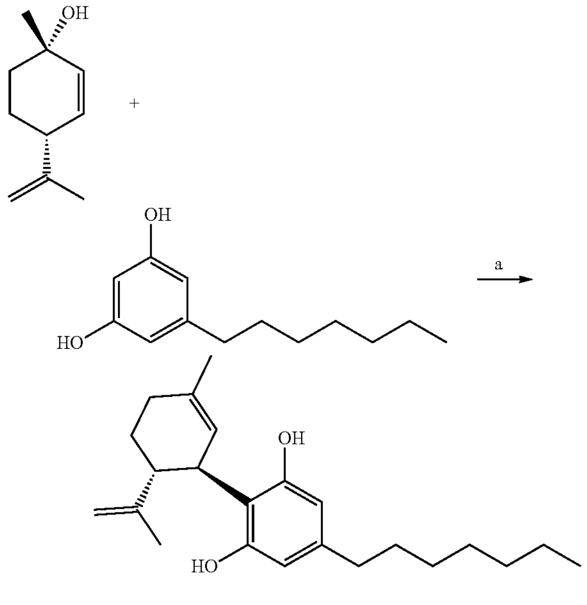

In both schemes (I) and (II) the acidic catalyst is preferably p-toluenesulphonic acid. Further, in both schemes (I) and (II), the reaction is preferably performed under inert atmosphere in a halogenated organic solvent at a temperature of −10±5° C., for a time ranging from 30 to 90 min. The halogenated solvent is more preferably dichloromethane.

The method to produce the cannabinoid compound Δ9 THCB of formula (II) comprises reacting the CBDB of the above described formula (I) with hydrochloric acid obtaining the intermediate compound (−)trans HCl-THCB of formula (V).

(V)

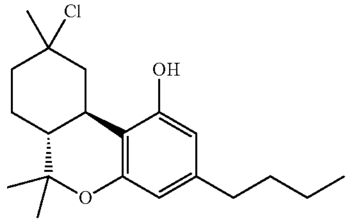

(-)-trans-HCl-THCB

The intermediate compound of formula (V) is then treated with a basic compound, obtaining Δ9 THCB.

In a preferred embodiment, the reagent CBDB is not used in pure form, but in a mixture with its thermodynamically more stable conversion product (−)trans Δ8 THCB of formula (VII)

(VII)

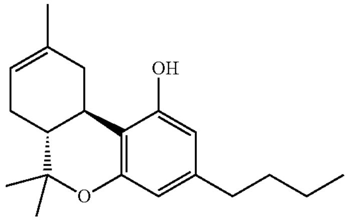

(-)-trans-$\Delta^8$-THCB

The mixture of CBDB with compound (VII) is easily obtained in a process of stereoselective synthesis of CBDB as previously described, wherein CBDB is not isolated immediately, but is allowed to remain in the reaction mixture, as long as a convenient amount of compound (VII), e.g. 40% or more of the original CBDB, is converted into compound (VII).

The above described method to produce the cannabinoid compound Δ9 THCB of formula (II) can be applied likewise to the production of the cannabinoid compound Δ9 THCB of formula (III), with the difference that the compound to be reacted with hydrochloric acid is the CBDP of formula (IV) previously described, obtaining in this case the intermediate compound (−)trans HCl-THCP of formula (VI), (VI)

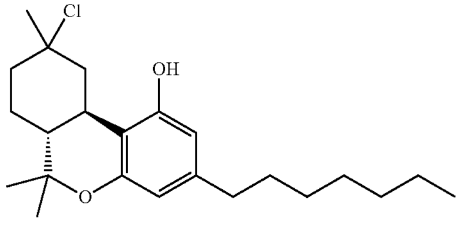

The intermediate compound (VI) is then treated with a basic compound, obtaining Δ9 THCP.

Also in this case, in a preferred embodiment, the reagent CBDP is not used in pure form, but in a mixture with its thermodynamically more stable conversion product (−)trans Δ8 THCP of formula (VIII)

(VIII)

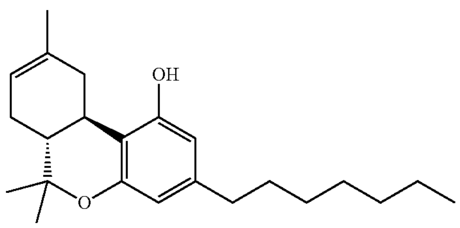

The mixture of CBDP with compound (VIII) is easily obtained in a process of stereoselective synthesis of CBDP as previously described, wherein CBDP is not isolated immediately, but is allowed to remain in the reaction mixture, as long as a convenient amount of compound (VIII), e.g. 40% or more of the original CBDP, is converted into compound (VIII).

In an even preferred embodiment, the mixture reacted with hydrochloric acid is exclusively or almost exclusively made of compound (VIII).

In both synthesis of Δ9 THCB e Δ9 THCP, the reaction with hydrochloric acid is preferably performed under catalysis of ZnCl2. Furthermore, in both synthesis of Δ9 THCB e Δ9 THCP, the basic compound reacted with the respective intermediates (V) and (VI) is preferably potassium amylate.

The above referred methods of stereoselective synthesis have been described for the compounds of formulas (I) to (IV) in which the group R1 is —H (hydrogen). The synthesis of the corresponding acid derivatives in which the group R1 is —COOH (carboxy) can be realized as described above, using the corresponding equivalent reagents in which R1 is —COOH, in particular using 6-carboxy 5-butylbenzene-1,3-diol in the above Scheme (I) or 6-carboxy 5-heptylbenzene-1,3-diol in the above Scheme (II).

Non-limitative examples of synthesis of the compounds of formula (I) to (IV), developed according to the above rules, are presented in full extension in the experimental section.

The present compounds are characterized by affinity to a cannabinoid receptor, in particular the cannabinoid receptor CB1. In some instances, the compounds are exclusively affine to the CB1 receptor; in other instances, they are mainly affine to the CB1, with a minor affinity to the CB2 receptor. In all instances, the CB1 affinity is dominant, with the consequence that the compounds can be used in the modulation of the CB1 receptor. The modulation can be of agonist or antagonist type; preferably it is of the agonist type.

In particular, it has been found that the length of the alkyl chain of the resorcinyl moiety present in formulas (I) to (IV) positively correlates with the potency/specificity of CB1 binding affinity, as confirmed by the fact that heptyl derivatives like the compound (III) showed the highest binding affinity to CB1. This finding was further supported by the evidence of docking pose studies in the CB1 receptor, also reported in the experimental section, whereby the full occupancy of the binding pocket of the hCB1 receptor was obtained only in case of the heptyl derivatives of formulas (III) and (IV).

Based on these findings, a further object of the present invention is a method of treating or preventing a disease mediated by the CB1 receptor comprising administering a compound claim 1 to a patient in need thereof.

A further object of the invention is a pharmaceutical composition comprising a compound of claim 1 in presence of one or more pharmaceutically acceptable excipients.

BRIEF DESCRIPTION OF DRAWINGS

The foregoing summary and the following detailed description are better understood when read in conjunction with the appended drawings. Exemplary embodiments are shown in the drawings; however, it is understood that the embodiments are not limited to the specific structures depicted herein.

FIG. 1 shows structure and names (IUPAC, INN and abbreviation) of cannabidiol (CBD), cannabidibutol (CBDB), cannabidivarin (CBDV), main by-products of synthesis of CBD (1 and 2) and ibuprofen (used as internal standard for HPLC-UV method), according to an exemplary embodiment of the present disclosure.

FIG. 11 shows structure of the main cannabinoids THC and CBD, their acidic precursors, THCA and CBDA, and their respective propyl and butyl homologues, according to an exemplary embodiment of the present disclosure.

FIG. 12(A) shows the extracted ion chromatograms (EICs) of the acidic forms before (native FM2) and after decarboxylation (decarboxylated FM2): EICs were chosen based on the exact mass calculated for $C_{22}H_{30}O_4$(THCA and CBDA), $C_{21}H_{28}O_4$(THCBA and CBDBA) and $C_{20}H_{26}O_4$ (THCVA and CBDVA).

FIG. 12(B) shows the EICs of the neutral species before (native FM2) and after decarboxylation (decarboxylated FM2): EICs were chosen based on the exact mass calculated for $C_{21}H_{30}O_2$(THC and CBD), $C_{20}H_{28}O_2$(THCB and CBDB) and $C_{19}H_{26}O_2$(THCV and CBDV), according to an exemplary embodiment of the present disclosure. Each peak is labelled with compound name and peak area.

FIGS. 15(A), 15(B), 15(C), 15(D), 15(E) and 15**(F), collectively, show the effect of THCB (10 and 20 mg/kg, i.p.) in the tetrad test, according to an exemplary embodiment of the present disclosure.

FIG. 15(A) shows a timeline of the tetrad procedure from $\Delta^9$-THCB administration according to an exemplary embodiment of the present disclosure.

FIG. 15(B) shows representative examples of movement path in vehicle or $\Delta^9$-THCB, according to an exemplary embodiment of the present disclosure.

FIG. 15(C) shows motor activity (distance, cm) in the OFT, according to an exemplary embodiment of the present disclosure.

FIG. 15(D) shows body temperature (change in body temperature, ° C.), according to an exemplary embodiment of the present disclosure.

FIG. 15(E) shows catalepsy (latency for moving, s) in the bar test, according to an exemplary embodiment of the present disclosure.

FIG. 17(A) shows extracted ion chromatograms (EIC) of CBDP and $\Delta^9$-THCP from a standard mixture at 25 and 10 ng/mL respectively FIG. 17(*a*) and from the native (red plot) and decarboxylated (black plot) FM2.

FIG. 17(B) shows extracted ion chromatograms (EIC) of CBDP and $\Delta^9$-THCP from a standard mixture at 25 and 10 ng/mL respectively FIG. 17(*a*) and from the native (red plot) and decarboxylated (black plot) FM2.

FIG. 17(C) shows a comparison of the high-resolution fragmentation spectra of synthetic and natural CBDP and $\Delta^9$-THCP in both positive (ESI+) and negative (ESI−) mode, according to an exemplary embodiment of the present disclosure.

FIG. 17(D) shows a comparison of the high-resolution fragmentation spectra of synthetic and natural CBDP and $\Delta^9$-THCP in both positive (ESI+) and negative (ESI−) mode, according to an exemplary embodiment of the present disclosure.

FIG. 18(A) shows reagents and conditions: a) 5-heptylbenzene-1,3-diol (1.1 eq.), pTSA (0.1 eq.), $CH_2Cl_2$, r.t., 90 min.; b) 5-heptylbenzene-1,3-diol (1.1 eq.), pTSA (0.1 eq.), DCM, r.t., 48 h; c) pTSA (0.1 eq.), $CH_2Cl_2$, r.t., 48 h; d) ZnCl2 (0.5 eq.), 4N HCl in dioxane (1 mL per 100 mg of $\Delta^8$-THCP), dry $CH_2Cl_2$, argon, 0° C. to r.t., 2 h. e) 1.75M potassium t-amylate in toluene (2.5 eq.), dry toluene, argon, −15° C., 1 h, according to an exemplary embodiment of the present disclosure.

FIG. 18(B) shows superimposition of $^1H$, $^{13}C$ NMR and circular dichroism spectra for natural (red line) and synthesized (blue line) (−)-trans-CBDP according to an exemplary embodiment of the present disclosure.

FIG. 18(C) shows superimposition of $^1H$, $^{13}C$ NMR and circular dichroism spectra for natural (red line) and synthesized (blue line) (−)-trans-CBDP, according to an exemplary embodiment of the present disclosure.

FIG. 18(D) shows superimposition of 1H, 13C NMR and circular dichroism spectra for natural (red line) and synthesized (blue line) (−)-trans-CBDP, according to an exemplary embodiment of the present disclosure.

FIG. 18(E) shows superimposition of $^1H$, $^{13}C$ NMR and circular dichroism spectra for natural (red line) and synthesized (blue line) (−)-trans-$\Delta^9$-THCP, according to an exemplary embodiment of the present disclosure.

FIG. 18(F) shows superimposition of $^1H$, $^{13}C$ NMR and circular dichroism spectra for natural (red line) and synthesized (blue line) (−)-trans-$\Delta^9$-THCP, according to an exemplary embodiment of the present disclosure.

FIG. 18(G) shows superimposition of $^1H$, $^{13}C$ NMR and circular dichroism spectra for natural (red line) and synthesized (blue line) (−)-trans-$\Delta^9$-THCP, according to an exemplary embodiment of the present disclosure.

FIG. 19(A) shows binding affinity ($K_i$) of the four homologues of $\Delta^9$-THC against human $CB_1$ and $CB_2$ receptors, according to an exemplary embodiment of the present disclosure.

FIG. 19(B) shows dose-response studies of $\Delta^9$-THCP against $hCB_1$ (in blue) and $hCB_2$ (in grey). All experiments were performed in duplicate and error bars denote s.e.m. of measurements, according to an exemplary embodiment of the present disclosure.

FIG. 20(A) shows time schedule of the tetrad tests in minutes from $\Delta^9$-THCP or vehicle administration, according to an exemplary embodiment of the present disclosure.

FIG. 20(B) shows locomotion decrease induced by $\Delta^9$-THCP administration in the open field test, according to an exemplary embodiment of the present disclosure.

FIG. 20(C) show locomotion decrease induced by $\Delta^9$-THCP administration in the open field test, according to an exemplary embodiment of the present disclosure.

FIG. 20(D) shows decrease of body temperature after $\Delta^9$-THCP administration; the values are expressed as the difference between the basal temperature (i.e., taken before $\Delta^9$-THCP or vehicle administration) and the temperature measured after $\Delta^9$-THCP or vehicle administration, according to an exemplary embodiment of the present disclosure.

FIG. 20(E) shows increase in the latency for moving from the catalepsy bar after $\Delta^9$-THCP administration, according to an exemplary embodiment of the present disclosure.

FIG. 20(F) shows increase in the latency after the first sign of pain shown by the mouse in the hot plate test following $\Delta^9$-THCP administration, according to an exemplary embodiment of the present disclosure. Data in FIGS. 20(*a*)-(*f*) are represented as mean±SEM of 5 mice per group, * indicate significant differences compared to 0 (vehicle injection), respectively, $*p<0.05$, $p<0.01$, $*p<0.001$ versus T7 0 mg/kg (vehicle), and the Kruskall-Wallis test followed by Dunn's post hoc tests.

DETAILED DESCRIPTION

Figure 2:
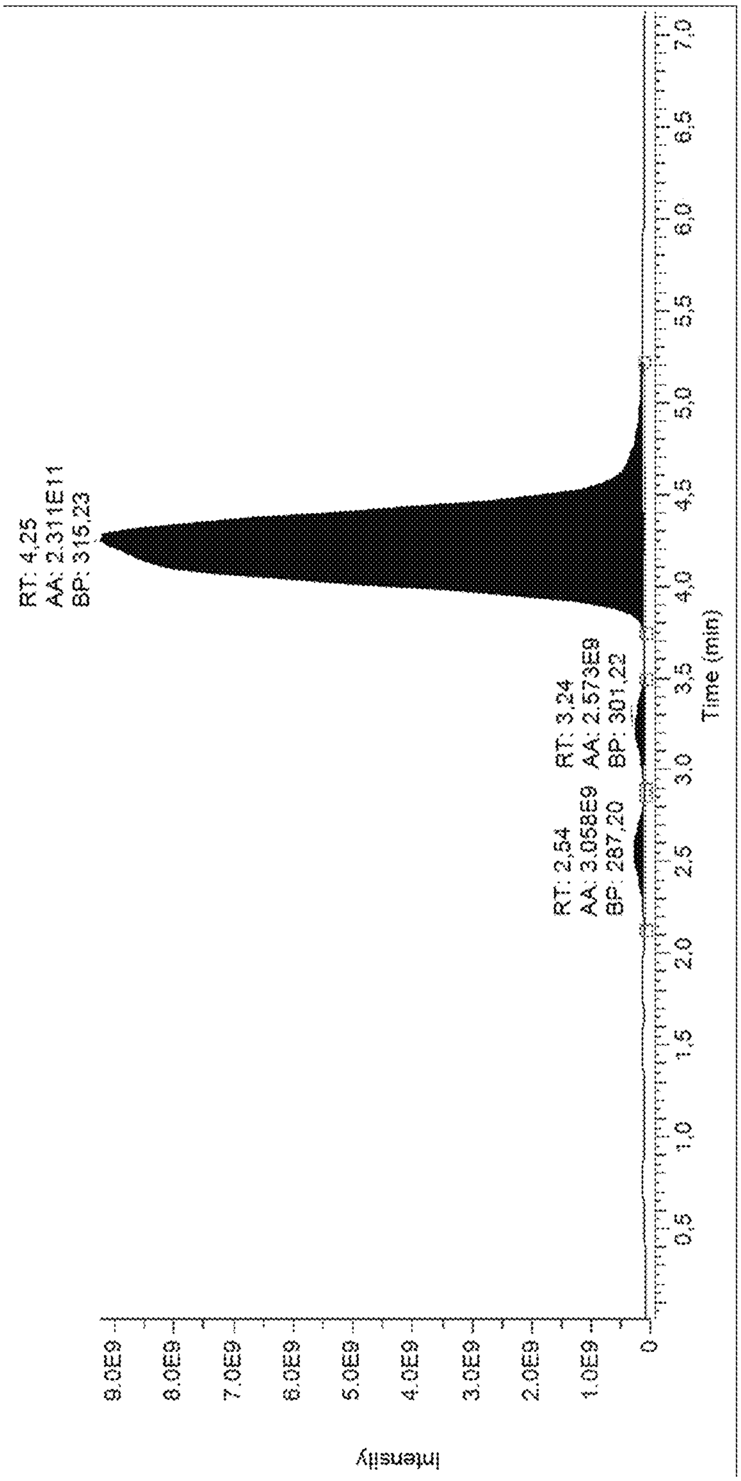
FIG. 2 shows total Ion Chromatogram (TIC) of a CBD authentic sample, according to an exemplary embodiment of the present disclosure. The mail peak is identified as CBD, the other two peaks at 2.54 and 3.24 min are impurity 1 and impurity 2 respectively.

The terminology used in the present disclosure is for the purpose of describing particular exemplary embodiments only and is not intended to be limiting. As used in the description of the embodiments of the disclosure and the appended claims, the singular forms "a," "an," and "the" are intended to include the plural forms as well, unless the context clearly indicates otherwise.

The term "and/or," as used herein, refers to and encompasses any and all possible combinations of one or more of the associated listed items.

The term "about," as used herein when referring to a measurable value such as an amount of a component, time, temperature, and the like, is meant to encompass variations of 20%, 10%, 5%, 1%, 0.5%, or even 0.1% of the specified amount. Unless otherwise defined, all terms, including technical and scientific terms used in the description, have the same meaning as commonly understood by one of ordinary skill in the art to which this disclosure belongs.

As used herein, the term "treating" or "treatment" refers to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom or condition. The treatment or amelioration of symptoms can be based on any objective or subjective parameter including, e.g., the result of a physical examination.

As used herein, the term "administering" refers to oral, topical, parenteral, intravenous, intraperitoneal, intramuscular, intralesional, intranasal, subcutaneous, or intrathecal administration to a subject, as well administration as a suppository or the implantation of a slow-release device, e.g., a mini-osmotic pump, in the subject.

As referred above, the present compounds are characterized by affinity to a cannabinoid receptor, in particular the cannabinoid receptor CB1. In some instances, the compounds are exclusively affine to the CB1 receptor; in other instances, they are mainly affine to the CB1, with a minor affinity to the CB2 receptor. In all instances, the CB1 affinity is dominant, with the consequence that the compounds can be used in the modulation of the CB1 receptor. The modulation can be of agonist or antagonist type; preferably it is of the agonist type.

There is no strict limitation as to the type of diseases mediated by the CB1 receptor being target of the present treatment. A non-limitative list thereof includes: metabolic syndromes such as type 2 diabetes, dyslipidemia, and obesity; eating disorders; constipation; cardiovascular diseases or disorders such as hypertension, congestive heart failure, cardiac hypertrophy, peripheral artery disease, cerebrovascular accidents, atherosclerosis, stroke, myocardial infarction, and cardiotoxicity associated with chemotherapy; fatty liver disease (steatohepatitis) and non-alcoholic fatty liver disease; kidney disease; diseases or disorders characterized by an addiction component such as smoking addiction or withdrawal, alcohol addiction or withdrawal, and drug addiction or withdrawal; bone diseases or disorders such as osteoporosis, Paget's disease of bone, and bone cancer; breast cancer; inflammatory diseases such as neuropathy and neuro-inflammatory disorders; autoimmune diseases such as rheumatoid arthritis, inflammatory bowel disease, and psoriasis; psychiatric diseases or disorders such as anxiety, mania, schizophrenia; disorders or diseases associated with memory impairment and/or loss of cognitive function such as Parkinson's disease, Alzheimer's disease and dementia; migraine; multiple sclerosis and Guillain-Barre syndrome; epilepsy; asthma.

The present compounds can be administered at any suitable dose in the methods of the invention. In general, the compounds are administered at a dose ranging from about 0.1 milligrams to about 1000 milligrams per kilogram of a subject's body weight (i.e., about 0.1-1000 mg/kg). The dose of a compound can be, for example, about 0.1-1000 mg/kg, or about 1-500 mg/kg, or about 25-250 mg/kg, or about 50-100 mg/kg. The dose can be about 1, 2, 3, 4, 5, 10, 15, 20, 25, 30, 35, 40, 45, 50, 55, 60, 65, 70, 75, 85, 90, 95, 100, 150, 200, 250, 300, 350, 400, 450, 500, 550, 600, 650, 700, 750, 800, 850, 900, 950 or 1000 mg/kg.

The dosages can be varied depending upon the requirements of the patient, the severity of the disorder being treated, and the particular formulation being administered. The dose administered to a patient should be sufficient to result in a beneficial therapeutic response in the patient. The size of the dose will also be determined by the existence, nature, and extent of any adverse side-effects that accompany the administration of the drug in a particular patient. Determination of the proper dosage for a particular situation is within the skill of the typical practitioner. The total dosage can be divided and administered in portions over a period of time suitable to treat to the condition or disorder.

Administration can be conducted for a period of time which will vary depending upon the nature of the particular disorder, its severity and the overall condition of the patient. Administration can be conducted, for example, hourly, every 2 hours, three hours, four hours, six hours, eight hours, or twice daily including every 12 hours, or any intervening interval thereof. Administration can be conducted once daily, or once every 36 hours or 48 hours, or once every month or several months. Following treatment, a patient can be monitored for changes in his or her condition and for alleviation of the symptoms of the disorder. The dosage can either be increased in the event the patient does not respond significantly to a particular dosage level, or the dose can be decreased if an alleviation of the symptoms of the disorder is observed, or if the disorder has been ablated, or if unacceptable side effects are seen with a particular dosage.

A therapeutically effective amount of a compound of the invention can be administered to the subject in a treatment regimen comprising intervals of at least 1 hour, or 6 hours, or 12 hours, or 24 hours, or 36 hours, or 48 hours between dosages. Administration can be conducted at intervals of at least 72, 96, 120, 168, 192, 216, or 240 hours, or the equivalent amount of days. The dosage regimen can consist of two or more different interval sets. For example, a first part of the dosage regimen can be administered to a subject multiple times daily, daily, every other day, or every third day. The dosing regimen can start with dosing the subject every other day, every third day, weekly, biweekly, or monthly. The first part of the dosing regimen can be administered, for example, for up to 30 days, such as 7, 14, 21, or 30 days. A subsequent second part of the dosing regimen with a different interval administration administered weekly, every 14 days, or monthly can optionally follow, continuing for 4 weeks up to two years or longer, such as 4, 6, 8, 12, 16, 26, 32, 40, 52, 63, 68, 78, or 104 weeks. Alternatively, if the disorder goes into remission or generally improves, the dosage may be maintained or kept at lower than maximum amount. If the condition or disorder relapses, the first dosage regimen can be resumed until an improvement is seen, and the second dosing regimen can be implemented again. This cycle can be repeated multiple times as necessary.

Additional active agents or therapies can be co-administered or otherwise combined with the compounds of the present invention. Additional active agents and therapies suitable for use in the methods of the invention include, but are not limited to, compounds used in the treatment of type-2 diabetes and obesity, such as insulin and insulin analogues, dipeptidyl peptidase-4 (DPP-4) inhibitors, glucagon-like peptide-1 analogues, hypoglycemic agents, such as alpha-glucosidase inhibitors, biguanides, sulfonyl ureas, thiazolidinediones, weight loss therapies, such as appetite suppressing agents, serotonin reuptake inhibitors, noradrenaline reuptake inhibitors, β3-adrenoceptor agonists, and lipase inhibitors. Compounds used in the treatment of cardiovascular disease and dysfunction can also be used in the methods invention, including, but not limited to, diuretics, angiotensin-converting enzyme (ACE) inhibitors, angiotensin II antagonists, beta-blockers, calcium antagonists, such as nifedipine, HMG-CoA-reductase inhibitors, such as statins, digoxin, aldosterone antagonists, and organic nitrates. Other lipid modulating agents including, but not limited to, fibrates and bile acid-binding resins can be used in the methods of the invention. The compounds of the invention can be used with compounds used to assist smoking cessation including, but not limited to, norepinephrine-dopamine reuptake inhibitors such as bupropion.

Compounds used in the treatment of bone diseases and disorders can be used in the methods of the invention. Such compounds include, but are not limited to anti-resorptive agents such as bisphosphonates, anabolic agents such as parathyroid hormone, RANKL inhibitors such as denosumab; and estrogen replacement and selective estrogen receptor modulators such as raloxifene. Compounds used in the treatment of breast cancer, such as compounds which modulate tubulin polymerization, such as paclitaxel; targeted therapies, such as antibodies against specific cell surface markers on tumor cells, such as antibodies against the HER2 oncoprotein, such as trastuzumab.

Compounds used in the treatment of a disease or disorder with an inflammatory or autoimmune component can be used in the methods of the invention. Such compounds include non-steroidal anti-inflammatory drugs (NSAIDs); disease-modifying anti-rheumatic drugs such as immunosuppressants; anti-TNF agents, such as infliximab, etanercept, and adalimumab; and anti B-cell therapies, such as rituximab.

Compounds used in the treatment of psychiatric diseases and disorders can be used in the methods of the invention. Such compounds include as GABAA modulators, such as benzodiazepines; 5HT1A receptor agonists, such as buspirone; beta blockers; antipsychotics, such as dopamine receptor blockers and other drugs which modulate monoamine receptors, transporters or metabolism, such as tricyclic antidepressants, selective serotonin reuptake inhibitors, and monoamine oxidase inhibitors; lithium; and anti-epileptic drugs, such as those which block sodium channels, those which block T-type calcium channels, or those which block GABA transaminase or reuptake, including phenytoin, carbamazepine, valproate and vigabatrin. Compounds used in the treatment of a disease or disorder characterized by impairment of memory and/or loss of cognitive function can also be used in the methods of the invention, including, but not limited to such dopamine agonists and anticholinesterases.

In another aspect, the invention provides a pharmaceutical composition comprising one or more compounds of formulas (I) to (IV) as above described and one or more pharmaceutically acceptable excipients.

The pharmaceutical compositions can be prepared by any of the methods well known in the art of pharmacy and drug delivery. In general, methods of preparing the compositions include the step of bringing the one or more compounds of formulas (I) to (IV) (active ingredient) into association with a carrier containing one or more accessory ingredients. The pharmaceutical compositions are typically prepared by uniformly and intimately bringing the active ingredient into association with a liquid carrier or a finely divided solid carrier or both, and then, if necessary, shaping the product into the desired formulation. The compositions can be conveniently prepared and/or packaged in unit dosage form.

The pharmaceutical compositions can be in the form of a sterile injectable aqueous or oleaginous solutions and suspensions. Sterile injectable preparations can be formulated using non-toxic parenterally-acceptable vehicles including water, Ringer's solution, and isotonic sodium chloride solution, and acceptable solvents such as 1,3-butanediol. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables.

Aqueous suspensions contain the active ingredient in admixture with excipients suitable for the manufacture of aqueous suspensions. Such excipients include, but are not limited to: suspending agents such as sodium carboxymethylcellulose, methylcellulose, oleagino-propylmethylcellulose, sodium alginate, polyvinyl-pyrrolidone, gum tragacanth and gum acacia; dispersing or wetting agents such as lecithin, polyoxyethylene stearate, and polyethylene sorbitan monooleate; and preservatives such as ethyl, n-propyl, and p-hydroxybenzoate.

Oily suspensions can be formulated by suspending the active ingredient in a vegetable oil, for example, arachis oil, olive oil, sesame oil or coconut oil, or in a mineral oil such as liquid paraffin. The oily suspensions can contain a thickening agent, for example beeswax, hard paraffin or cetyl alcohol. These compositions can be preserved by the addition of an anti-oxidant such as ascorbic acid.

Dispersible powders and granules (suitable for preparation of an aqueous suspension by the addition of water) can contain the active ingredient in admixture with a dispersing agent, wetting agent, suspending agent, or combinations thereof. Additional excipients can also be present.

The pharmaceutical compositions of the invention can also be in the form of oil-in-water emulsions. The oily phase can be a vegetable oil, for example olive oil or *arachis* oil, or a mineral oil, for example liquid paraffin or mixtures of these. Suitable emulsifying agents can be naturally-occurring gums, such as gum acacia or gum tragacanth; naturally-occurring phospholipids, such as soy lecithin; esters or partial esters derived from fatty acids and hexitol anhydrides, such as sorbitan monooleate; and condensation products of said partial esters with ethylene oxide, such as polyoxyethylene sorbitan monooleate.

Pharmaceutical compositions containing compounds of the invention can also be in a form suitable for oral use. Suitable compositions for oral administration include, but are not limited to, tablets, troches, lozenges, aqueous or oily suspensions, dispersible powders or granules, emulsions, hard or soft capsules, syrups, elixirs, solutions, buccal patches, oral gels, chewing gums, chewable tablets, effervescent powders, and effervescent tablets. Compositions for oral administration can be formulated according to any method known to those of skill in the art. Such compositions can contain one or more agents selected from sweetening agents, flavoring agents, coloring agents, antioxidants, and preserving agents in order to provide pharmaceutically elegant and palatable preparations.

Tablets generally contain the active ingredient in admixture with non-toxic pharmaceutically acceptable excipients, including: inert diluents, such as cellulose, silicon dioxide, aluminum oxide, calcium carbonate, sodium carbonate, glucose, mannitol, sorbitol, lactose, calcium phosphate, and sodium phosphate; granulating and disintegrating agents, such as corn starch and alginic acid; binding agents, such as polyvinylpyrrolidone (PVP), cellulose, polyethylene glycol (PEG), starch, gelatin, and acacia; and lubricating agents such as magnesium stearate, stearic acid, and talc. The tablets can be uncoated or coated, enterically or otherwise, by known techniques to delay disintegration and absorption in the gastrointestinal tract and thereby provide a sustained action over a longer period. For example, a time delay material such as glyceryl monostearate or glyceryl distearate can be employed. Tablets can also be coated with a semi-permeable membrane and optional polymeric osmogents according to known techniques to form osmotic pump compositions for controlled release.

Compositions for oral administration can be formulated as hard gelatin capsules wherein the active ingredient is mixed with an inert solid diluent (such as calcium carbonate, calcium phosphate, or kaolin), or as soft gelatin capsules wherein the active ingredient is mixed with water or an oil medium (such as peanut oil, liquid paraffin, or olive oil).

Compounds of the invention can also be administered topically as a solution, ointment, cream, gel, suspension, eye-drops, and the like. Still further, transdermal delivery of compounds of the invention can be accomplished by means of iontophoretic patches and the like. The compound can also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols.

In a related aspect, the invention provides a kit having a pharmaceutical composition as described above and instructions for use.

The present invention is further disclosed by means of the following non-limitative examples 1-3; each of these examples contains an own general presentation and prior art review, description of material and methods, presentation and discussion of results and a list of internal literature references.

Example 1

Analysis of Impurities of Cannabidiol from Hemp. Isolation, Characterization and Synthesis of Cannabidibutol, the Novel Cannabidiol Butyl Analog.

Highlights

Cannabidivarin (CBDV) and cannabidibutol (CBDB) are the two major impurities in cannabidiol (CBD) extracted from hemp. In this example, CBDB was isolated and fully characterized for the first time. A stereoselective synthesis was carried out and absolute configuration assigned to natural CBD. A match of all properties of isolated CBDB and synthesized CBDB was obtained. A simple and selective HPLC-UV method was developed and validated. The method was applied to ten batches of commercial CBD marketed by certified companies.

Abstract

Cannabidiol (CBD), one of the two major active principles present in *Cannabis sativa*, is gaining great interest among the scientific community for its pharmaceutical, nutraceutical and cosmetic applications. CBD can be prepared either by chemical synthesis or extraction from *Cannabis sativa* (hemp). The latter is more convenient from several points of view, including environmental and economic, but mainly for the absence of harmful organic solvents generally employed in the chemical synthesis. Although CBD produced by hemp extraction is the most widely employed, it carries two major impurities. The first one is cannabidivarin (CBDV), whereas the second one is supposed to be the butyl analog of CBD with a four-term alkyl side chain. In this work, we report the isolation by semi-preparative liquid chromatography and the identification of this second impurity. A comprehensive spectroscopic characterization, including NMR, UV, IR, circular dichroism and high-resolution mass spectrometry (HRMS), was carried out on this natural cannabinoid. In order to determine its absolute configuration and chemical structure, the stereoisomer (1R,6R) of the supposed cannabinoid was synthesized and the physicochemical and spectroscopic properties, along with the stereochemistry, matched those of the natural isolated molecule. According to the International Nonproprietary Name, we suggested the name of cannabidibutol (CBDB) for this cannabinoid. Lastly, an HPLC-UV method was developed and validated for the qualitative and quantitative determination of CBDV and CBDB in samples of CBD extracted from hemp and produced according to Good Manufacturing Practices regulations for pharmaceutical and cosmetic use.

1.1 INTRODUCTION

Since its discover by Adams in 1940 [1] and structure elucidation by Mechoulam and Shvo in 1963 [2], studies on cannabidiol (CBD, FIG. 1) have undergone profound changes over the time. Initially, it was considered an inactive cannabinoid [3], thus leaving the field to the research on the "active" constituent of *Cannabis sativa*, $\Delta^9$-tetrahydrocannabinol ($\Delta^9$-THC). While deepening the knowledge on THC, the studies on CBD were confined to the interaction with the more interesting psychotropic isomer [3]. The period of silence on CBD eventually stopped in the early 2000's, when there was a boost in the number of publications on this cannabinoid due to the plethora of pharmacological activities addressed to CBD alone, many of which with therapeutic potential [3]. More than four hundred papers were published last year on CBD compared to about twenty exactly twenty years ago (from Scopus search "cannabidiol"). In 2018 CBD was approved by FDA for the treatment of severe forms of infant epilepsy (Lennox-Gastaut syndrome and Dravet syndrome) and it is now commercialized by GW Pharmaceuticals (UK) as a 100 mg/mL oral solution with the name of Epidiolex® [4]. CBD in Epidiolex is extracted from hemp inflorescence and therefore it is produced according to the Good Manufacturing Practices (GMP). GMP covers all stages of production from the starting materials to the facilities, equipment and processes, but also record keeping, personnel qualifications and training, sanitation and cleanliness. Hence, a drug substance that is produced as an Active Pharmaceutical Ingredient (API) should comply to a series of specifications including a detailed report of the chemical composition. GW Pharmaceuticals clearly indicates that CBD in Epidiolex is 98% pure, thus it contains some impurities. In its application patent entitled "Use of cannabinoids in the treatment of epilepsy" [5], GW Pharmaceuticals lists the impurities in the extracted cannabidiol including cannabidiolic acid (CBDA) 0.15% w/w, cannabidivarin (CBDV, FIG. 1) 1% w/w, $\Delta^9$-THC 0.15% w/w and CBD-$C_4$ (FIG. 1) 0.5% w/w. The latter is intended as 4-butyl-5'-methyl-2'-(prop-1-en-2-yl)-1',2',3',4'-tetrahydro-[1,1'-biphenyl]-2,6-diol, which is the analog of CBD with a butyl side chain in place of the conventional pentyl chain on the resorcinol moiety. However, no record of its physicochemical and optical characterization can be found in the scientific literature.

The same considerations on GMP are valid for other forms of CBD different from the oil, intended for pharmaceutical use, such as CBD crystals. CBD in this solid form can be obtained by either extraction from *Cannabis sativa* inflorescence or by a stereoselective synthesis. Natural CBD is generally extracted with organic solvents or by supercritical carbon dioxide from *cannabis* inflorescence, which has been previously decarboxylated since the plant only produces its acidic precursor CBDA [6]. Alternatively, CBDA can be extracted and then decarboxylated by heating the extract to get CBD [6, 7]. The extract usually undergoes a "winterization" or dewaxing step in order to remove the waxes and then CBD is purified. Purification can be performed by chromatography or directly crystallized from the winterized extract from either pentane or hexane [5, 8]. As an alternative, pure CBD can be produced via a stereoselective synthesis as reported by Petrzilka et al. [9] and later improved by Baek et al. [10]. The synthetic route involves the acid condensation of p-mentha-2,8-dien-1-ol with olivetol. However, beside CBD, as the major product, two main by-products are always obtained, namely a CBD isomer defined as "abnormal CBD" (abn-CBD, 1, FIG. 1) and a CBD with an additional p-menthal,8-dien-3-yl moiety in 4' position, namely 5,5"-dimethyl-6'-pentyl-2,2"-di(prop-1-en-2-yl)-1,1",2,2",3,3",4",6-octahydro-[1,1':3',1"-terphenyl]-2',4'-diol (2, FIG. 1). Thus, chromatographic purification may be required to obtained CBD with a degree of purity suitable for the pharmaceutical use, with consequent final yield not greater than 60%. Therefore, from both economic and ecological point of view, the extraction of CBD from *cannabis* inflorescence still remains a suitable process for industrial CBD production.

Notwithstanding the increasing use of CBD in pharmaceutical and cosmetic products, there is no related monograph in the official pharmacopoeias. The only official document reporting a protocol for solid or oily CBD formulations is a monograph in the German codex DAC/NRF, which has legal value only in Germany [11]. The monograph reports the main physicochemical properties, the methods for identification including thin layer chromatography, and the methods for determining the purity including liquid chromatography coupled to UV detection (HPLC-UV). The monograph also reports the impurities that can be encountered in a sample of solid CBD, specifically cannabinol (CBN), $\Delta^9$-THC and $\Delta^8$-THC, which together with other minor non specified impurities should be not more than 0.5% (w/w). The same monograph reports the preparation of an oily formulation of CBD 50 mg/mL in MCT (medium-chained triglycerides). However, the monograph does not mention two of the main impurities that can be found in CBD extracted from hemp like CBDV and CBD-$C_4$. The amount of the two impurities in the final product could be relatively high, up to 1% and 0.5% (w/w) for CBDV and CBD-$C_4$ respectively [5]. Although GMP procedures might be slightly different among countries, they all complies to general rules. Stacking to ICH guidelines, detection of impurities in an Active Pharmaceutical Ingredient (API) is regulated by the document Q3A(R2), which fixes the threshold for the determination of organic impurities according to the daily dose of the drug substance. Specifically, an impurity should be identified when present at a level of 0.10% and qualified at a level of 0.15% in a drug substance with a daily dose below 2 g/day. In a drug substance with a daily dose above 2 g/day, an impurity should be identified and qualified when present at a level of 0.05%. According to these guidelines, both impurities CBDV and CBD-$C_4$ should be qualified and reported in the certificate of analysis of the CBD product. To this end, suitable analytical methods should be applied to quantify these two compounds. A certified analytical standard for CBDV is commercially available and few analytical methods for its quantitative determination can be found in the literature [7, 12]. On the other hand, no analytical standard is available for CBD-$C_4$ and no analytical method has been published. Moreover, its identification in *cannabis* samples or CBD products has been obtained by only means of mass spectrometry data. No further characterization has been performed and the cannabinoid has never been isolated for determination. To the best of our knowledge and according to exact structure search on SciFinder, the most comprehensive database for chemical literature, only three scientific papers reports the mass spectrometry profile of CBD-$C_4$ using either gas chromatography analysis coupled to mass spectrometry (GC-MS) [13, 14] or Sorptive Tape-like Extraction coupled with Laser Desorption Ionization Mass Spectrometry (STELDI-MS) [15].

In the light of the above, the aim of the present work was to provide a full chemical characterization of CBD-$C_4$ including high-resolution mass spectrometry data (MS and MS/MS in positive and negative ionization mode) and spectroscopic data [NMR ($^1$H, $^{13}$C, COSY, HSQC and HMBC), IR, UV, circular dichroism (CD) and optical rotatory power]. In order to determine the identity of CBD-$C_4$, a stereoselective synthesis of the trans isomer (1R,6R) was carried out and all chemical properties were compared with those of CBD-$C_4$ directly isolated from commercial CBD crystal (extracted from hemp and produced according to GMP regulations) by semi-preparative liquid chromatography. According to the International Nonproprietary Name (INN), we suggested for this CBD analog the name "cannabidibutol" (CBDB). With the pure analytical standard of CBDB in hand, a simple and sensitive liquid chromatography method coupled to UV detection (HPLC-UV) was developed and validated ad hoc in order to quantity both CBDV and CBDB in CBD samples extracted from hemp. The method was validated according to ICH guidelines (Q2(R1)) in terms of selectivity, linearity, accuracy, precision, dilution integrity and stability. Lastly, it was successfully applied to ten commercially available CBD samples marketed by certified companies.

1.2. EXPERIMENTAL

1.2.1 Chemicals and Reagents

Ethanol 96% analytical grade was bought from Carlo Erba (Milan, Italy). Acetonitrile, water and formic acid were all LC-MS grade and purchased from Carlo Erba. Cannabidivarin (CBDV) was purchased as a Cerilliant certified analytical standard (Sigma-Aldrich, Milan, Italy). Ibuprofen (FIG. 1) was bought from Farmalabor (Canosa di Puglia, Italy). Samples of pure cannabidiol (extracted from hemp and produced according to GMP regulations) were kindly provided by three companies: Ricerche Sperimentali Montale S.P.A. (Montale, Italy), Fagron Italia (Bologna, Italy) and CBDepot (Prague, Czech Republic). (1S,4R)-1-methyl-4-(prop-1-en-2-yl)cycloex-2-enol and 5-butylbenzene-1,3-diol were purchased from Combi-blocks (San Diego, CA, USA) and GreenPharma (Foligno, Italy), respectively. Chemicals and solvents for the synthesis were reagent grade and used without further purification.

1.2.2 Synthesis of (1'R,2'R)-5'-methyl-4-pentyl-2'-(prop-1-en-2-yl)-1',2',3',4'-tetrahydro-[1,1'-biphenyl]-2,6-diol, (−)-trans-Cannabidibutol (CBDB)

To a solution of 5-butylbenzene-1,3-diol (83 mg, 0.50 mmol, 1 eq.) and p-toluenesulfonic acid (9 mg, 0.05 mmol, 0.1 eq.) in dry dichloromethane (DCM) (5 mL) at −10° C., under argon atmosphere, a solution of (1S,4R)-1-methyl-4-(prop-1-en-2-yl)cycloex-2-enol and 5-butylbenzene-1,3-diol (76 mg, 0.50 mmol, 1 eq.) in 5 mL of dry DCM was added dropwise. The mixture was stirred in the same conditions for 1 h and then quenched with a saturated solution of $NaHCO_3$(10 mL). The resulting mixture was extracted with diethyl ether (2×10 mL). The combined organic phases were washed with brine, dried over anhydrous $Na_2SO_4$ and concentrated. The crude was purified over silica gel (crude: silica gel ratio 1/200, eluent:cyclohexane:DCM 8/2) and all the chromatographic fractions were analyzed by HPLC-UV and UHPLC-HESI-Orbitrap. The fractions containing exclusively CBDB without impurities were collected to give 48 mg of a reddish oil (32% yield, purity>99%).

1.2.3. Isolation of Natural Cannabidibutol

A sample of commercial CBD crystals (1 g) was dissolved in acetonitrile (10 mL) and 0.5 mL aliquots of the solution were injected in a semi-preparative LC system (Octave 10 Semba Bioscience, Madison, USA). The separation was carried out on a fully porous silica stationary phase (Luna 5 μm C18(2) 100 Å, 250×10 mm) (Phenomenex, Bologna, Italy) with a mobile phase composed of acetronitrile:0.1% aqueous formic acid 70:30 (v/v) at a flow rate of 5 mL/min.

The impurity CBDV eluted at about 12 min, CBDB eluted at about 14 min and CBD eluted between 15 and 20 min. The fractions containing CBDV and CBDB were collected and analyzed by analytical HPLC-UV. The fractions containing exclusively CBDB were combined and dried on the rotavapor at 70° C. An amount of about 1 mg of CBDB was obtained as a reddish oil.

1.2.4 Chemical and Spectroscopic Characterization of Cannabidibutol

One-dimensional $^1H$ and $^{13}C$ NMR and two-dimensional NMR (COSY, HSQC and HMBC) were acquired a DPX-600 Avance (Bruker) spectrometer (600.13 MHz for $^1H$ NMR and 150.92 MHz for $^{13}C$ NMR). A 10 mg aliquot of synthetic CBDB and 1 mg aliquot of CBDB isolated from CBD were solubilized in 700 and 250 μL of $CDCl_3$ (at 99.96% of deuteration) and placed in a 5 mm and 3 mm NMR tube, respectively. All NMR spectra were recorded at 298 K. $^1H$-NMR were acquired with a spectral width of 13204.2 Hz, a relaxation delay of 5 s, a pulse width of 11.23 Hz and 16 number of transient. Proton chemical shifts were reported in parts per million (ppm, 6 units) and referenced to the solvent residual peaks ($CDCl_3$ 6=7.26 ppm). Coupling constants are reported in Hertz (Hz). Splitting patterns are designed as s, singlet; d, doublet; t, triplet; q, quartet; dd, double doublet; m, multiplet; b, broad. $^{13}C$-NMR were acquired with a spectral width of 33.3 kHz, a relaxation delay of 5 s, a pulse width of 10.00 Hz and 128 and 10240 number of transient for syn-CBDB and ext-CBDB, respectively. Carbon chemical shifts were reported in parts per million (ppm, 6 units) and referenced to the solvent residual peaks ($CDCl_3$ 6=77.20 ppm). The COSY were recorded as a 1024×160 matrix with 2 transients per t1 increment and processed as a 1024×1024 matrix. The HSQC spectra were collected as a 1024×256 matrix with 4 transients per t1 increment and processed as a 1024×1024 matrix, and the one-bond heteronuclear coupling value was set to 145 Hz. The HMBC spectra were collected as a 2048×220 matrix with 8 transients per t1 increment and processed as a 2048×1024 matrix, and the long-range coupling value was set to 8 Hz. IR spectra were recorded at 25° C. on a Perkin-Elmer Spectrum Two ATR-IR, scanning from 450 to 4000 $cm^{-1}$. Circular dichroism (CD) and UV spectra were acquired on a Jasco (Tokyo, Japan) J-1100 spectropolarimeter using a 50 nm/min scanning speed. Quartz cells with a 10 mm path length were employed to record spectra in the 400-200 nm range. Optical rotation (a) was measured with the P-2000 Digital Polarimeter (cell-length 100 mm, volume 1 mL) from Jasco Europe (Milan, Italy).

1.2.5 HPLC-UV Analyses

High performance liquid chromatography (HPLC) analyses were carried out on an Agilent 1220 Infinity LC System (Waldbronn, Germany), consisting of a vacuum degasser, a binary pump, a manual injector, a column compartment and a UV detector. The separation of the analytes was performed with a Poroshell 120 C18 column (Poroshell 120 SB-C18, 3.0×150 mm, 2.7 μm, Agilent, Milan, Italy) eluting a mobile phase composed of 0.1% formic acid in both (A) water and (B) acetonitrile (ACN). An isocratic elution with 70% B was set for 10 minutes, then 95% B was pumped for 5 min and re-equilibration of the column was set for 2 min for a total run time of 17 min. The flow rate was maintained constant at 0.5 mL/min. The loading loop capacity was 6 μL. The loop was washed before each run first with 50 μL of ethanol 96% then with 50 μL of mobile phase. The UV trace was acquired at 228 nm. The analytes peaks were manually integrated using the EZChrom software (Agilent Technologies), which was employed also for controlling the online analysis.

1.2.6 UHPLC-HESI-Orbitrap Mass Spectrometry Analyses

Ultrahigh-performance liquid chromatography analyses were carried out for identification and purity test purposes. They were performed on a Thermo Fisher Scientific Ultimate 3000 equipped with a vacuum degasser, a binary pump, a thermostated autosampler, a thermostated column compartment and a Q-Exactive Orbitrap mass spectrometer with a heated electrospray ionization (HESI) source. The mass spectrometry parameters were optimized by direct infusion of the single analytes at the concentration of 1 μg/mL with a flow rate of 0.1 mL/min through a syringe pump. The HESI parameters were: capillary temperature, 320° C.; vaporizer temperature, 280° C.; electrospray voltage, 4.2 kV (positive mode) and 3.8 kV (negative mode); sheath gas, 55 arbitrary units; auxiliary gas, 30 arbitrary units; S lens RF level, 45. Control of online analyses was carried out using Xcalibur 3.0 software (Thermo Fisher Scientific, San Jose, CA, USA). The exact masses of the compounds were calculated by the Qualbrowser in Xcalibur 3.0 software. The analyses were acquired in full scan data-dependent acquisition (FS-dd-$MS^2$) in positive and negative mode at a resolving power of 70,000 FWHM at m/z 200. The other mass analyzer parameters were: scan range, m/z 250-400; AGC, 3e6; injection time, 100 ms; isolation window for the filtration of the precursor ions, m/z 2. Fragmentation of precursors was performed at 30 as normalized collision energy (NCE) by injecting working mix standard solution at a concentration of 5 μg/L. Detection was based on calculated $[M+H]^+$ and [M−H]− molecular ions with an accuracy of 2 ppm, retention time and fragmentation match (fragments m/z and intensity) with pure analytical standards. Analytical selectivity was assessed by UHPLC-HESI-Orbitrap MS using the same chromatographic conditions employed for the HPLC-UV method except for the different length of the column (Poroshell 120 SB-C18, 3.0×100 mm, 2.7 μm, Agilent, Milan, Italy).

1.2.7 Preparation of Standard Solutions

A stock solution of internal standard (ibuprofen 10 mg/mL) was prepared by dissolving 100 mg in 10 mL of acetonitrile. Three serial 1/10 dilutions of the internal standard (IS) stock solution were performed to obtain 100 mL of IS working solution with the final concentration of 1 μg/mL in ACN.

Stock solution of CBDV (1000 μg/mL in methanol) and CBDB (1000 μg/mL in ACN) were properly diluted in the IS working solution to obtain calibration standard solutions (CS) at the final concentrations of 0.28, 1.41, 2.82, 9.40, 28.2 and 56.4 μg/mL for CBDV and 0.12, 0.60, 1.20, 4.00, 12.0 and 24.0 μg/mL for CBDB. Independently prepared CBDV and CBDB mix solutions were prepared in IS and used as the low concentration quality control (LQC) (0.56 μg/mL for CBDV and 0.24 μg/mL for CBDB), medium concentration quality control (MQC) (18.8 μg/mL for CBDV and 8.00 μg/mL for CBDB), and high concentration quality control (HQC) (45.1 μg/mL for CBDV and 19.2 μg/mL for CBDB) samples. QCs were prepared as for calibration standards.

1.2.8 Method Validation

In order to demonstrate the reliability and robustness of the method, a method validation was carried out based on EMA guidelines and in agreement with international guidelines for analytical techniques for the quality control of pharmaceuticals (ICH guidelines) [16, 17]. The method was validated in terms of selectivity, linearity, accuracy, precision, dilution integrity and stability. No matrix effect or recovery were assessed as the matrix is represented by acetonitrile, for which no matrix effect should be encountered as it is present in the mobile phase.

Selectivity. Selectivity is performed in order to assess the ability of the method to differentiate and quantify the analytes in the presence of other components in the sample. It was investigated by analyzing blank samples, samples containing the analytes and authentic standards and comparing the retention times of potential interfering compounds with those of reference standards and IS. Identity of the analytes was assessed by comparing accurate (within 2 ppm error) m/z of $[M+H]^+$ and $[M-H]^-$ ions and MS/MS spectra of analytical standards with those obtained by UHPLC-HESI-Orbitrap for the analytes in authentic samples.

Linearity. Calibration curve was constructed at six non-zero calibration levels 0.28, 1.41, 2.82, 9.40, 28.2 and 56.4 μg/mL for CBDV, 0.12, 0.60, 1.20, 4.00, 12.0 and 24.0 μg/mL for CBDB, and 1.00 μg/mL for IS. Peak area ratios of analyte-to-IS were plotted vs actual concentrations. Calibration curve was built at the beginning of each validation day of five consecutive days (n=5). A linear correlation was assumed if the coefficient of determination ($R^2$) was greater than 0.998 using weighed regression method ($1/x^2$). The back calculated concentrations should be within 15% of the nominal concentrations, and within 20% of the lower limit of quantification (LLOQ).

Limit of detection (LOD) and limit of quantification (LOQ). Limit of detection (LOD) was estimated based on a 3:1 signal-to-noise (S/N) ratio. Standard stock solutions of the analytes were appropriately diluted at the levels of their respective estimated LOD values. The LOD values were then calculated as three times the standard deviation (SD) obtained by repeatedly analyzed standards (n=5). Lower limit of quantification (LLOQ) was estimated based on a 10:1 S/N ratio and calculated as ten times the SD of repeatedly analyzed standards. The upper limit of quantification (ULOQ) was set at 10% above the highest concentration of the analytes in a concentrated sample of CBD (10 mg/mL).

Autosampler carryover. Autosampler carryover was evaluated by running two blank samples after a calibration standard at the ULOQ and after a high concentration sample (CBD 10 mg/mL). The carryover should not be greater than 20% of the LOQ for the analytes and 5% for IS.

Accuracy and precision. The precision and accuracy were evaluated at four levels, LLOQ (0.28 μg/mL for CBDV and 0.12 μg/mL for CBDB), LQC (0.56 μg/mL for CBDV and 0.24 μg/mL for CBDB), MQC (18.8 μg/mL for CBDV and 8.00 μg/mL for CBDB), and HQC (45.1 μg/mL for CBDV and 19.2 μg/mL for CBDB). Each sample was analyzed in triplicate within a single day to determine the intra-day precision and accuracy. The replicate analyses were repeated on freshly prepared standard solutions for five successive days (n=15) to determine the inter-day precision and accuracy. The precision was expressed as coefficient of variation (CV), and the accuracy was expressed as the percentage of mean calculated compared to nominal concentration.

Dilution integrity. Dilution integrity was carried out using a spiking standard solution of the analytes prepared by diluting standard stock solutions to a final concentration that is three times that of the ULOQ (170.4 μg/mL for CBDV and 72.00 μg/mL for CBDB). Dilution integrity was demonstrated by diluting the spiking solution in IS to ⅕, 1/10 and 1/20 of its original concentration. Five replicates per dilution factor were run. The concentrations were calculated by applying the dilution factor 5, 10 and 20 against freshly prepared calibration curve. Dilution integrity is ensured as long as precision and accuracy are <15% and ±15% respectively.

Stability. The short-term stability of the standard analytes was determined for LQC and HQC samples for 24 h at room temperature and under refrigeration (2-8° C.). The drugs were considered stable if the mean concentration (n=3 for each sample) was within ±15% of the nominal concentration.

Preparation and analysis of CBD samples. Authentic CBD samples (API grade) were prepared by weighing 10 mg of solid crystals and dissolving them in 1 mL of IS working solution. A 100 μL aliquot of the solution was diluted with 900 μL of IS working solution to get a CBD concentration of 1 mg/mL. The HPLC-UV analyses of authentic CBD samples were carried out in triplicate employing the validated method described above.

1.3. RESULTS AND DISCUSSION

1.3.1 Identification of CBD Impurities by Mass Spectrometry

CBD samples were analyzed by UHPLC-HESI-Orbitrap, which represents the cutting-edge technology for mass spectrometry allowing for superior accuracy and precision (below 2 ppm error) in the determination of the exact mass and fragmentation profiles of organic compounds. The main peak in the chromatograms (FIG. 2) was identified as CBD by overlap of the extracted ion chromatogram (EIC, FIG. 3) and MS/MS spectra of the pure analytical standard of CBD analyzed in the same LC-MS conditions in both ESI+ and ESI− mode (FIG. 4). The MS spectrum of the peak at 4.2 min does not show any other interfering compound. The precursor ion $[M+H]^+$ has m/z 315.2314 and the [M−H]− has m/z 313.2179.

Figure 3:
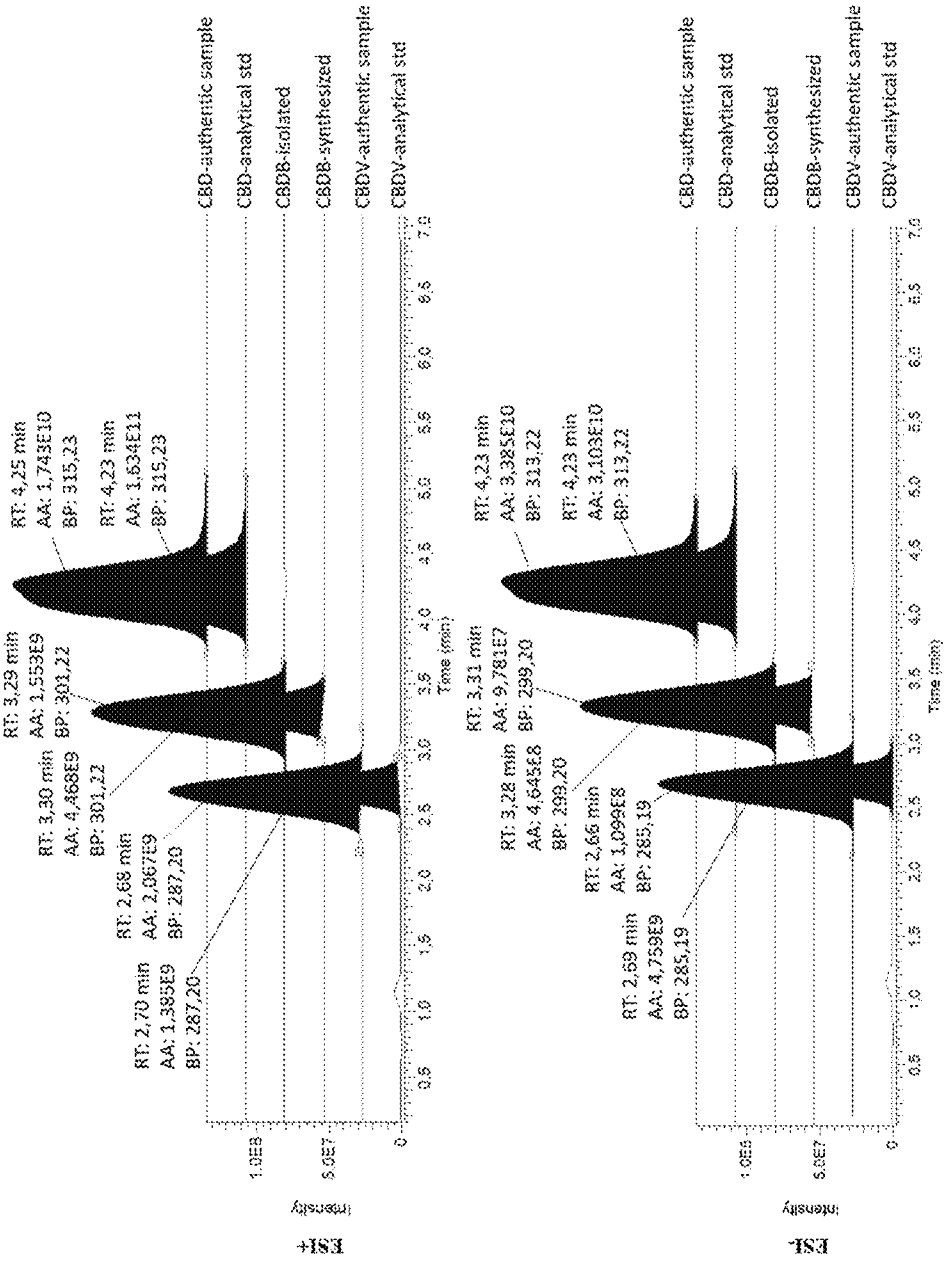
FIG. 3 shows extracted Ion Chromatograms (EIC) of CBD, CBDB and CBDV in positive (top) and negative (bottom) ionization mode, according to an exemplary embodiment of the present disclosure. Area of the peaks were obtained by extracting the exact mass (Appm=2) of CBD ($[M+H]^+$ 315.2314, $[M-H]^-$313.2179), CBDB ($[M+H]^+$ 301.2157, $[M-H]^-$299.2016) and CBDV ($[M+H]^+$ 287.2002, $[M-H]^-$285.1861). The chromatograms show the exact match of CBD and CBDV in samples with authentic analytical standards and the match of synthetic CBDB with natural isolated CBDB.
Figure 4A:
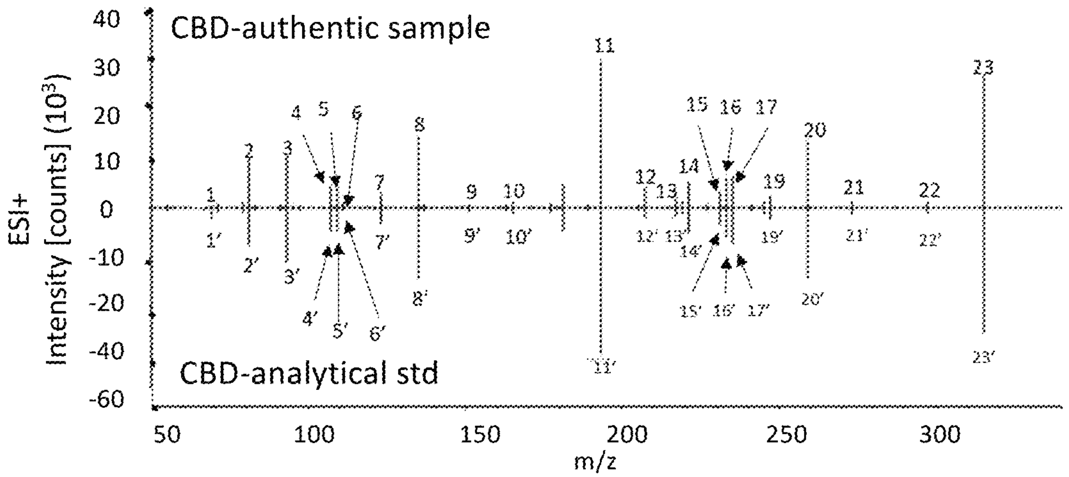
FIG. 4(A) shows match of MS/MS spectra of CBD in authentic samples and reference analytical standard in positive ionization mode by UHPLC-HESI-Orbitrap, according to an exemplary embodiment of the present disclosure.
Figure 4B:
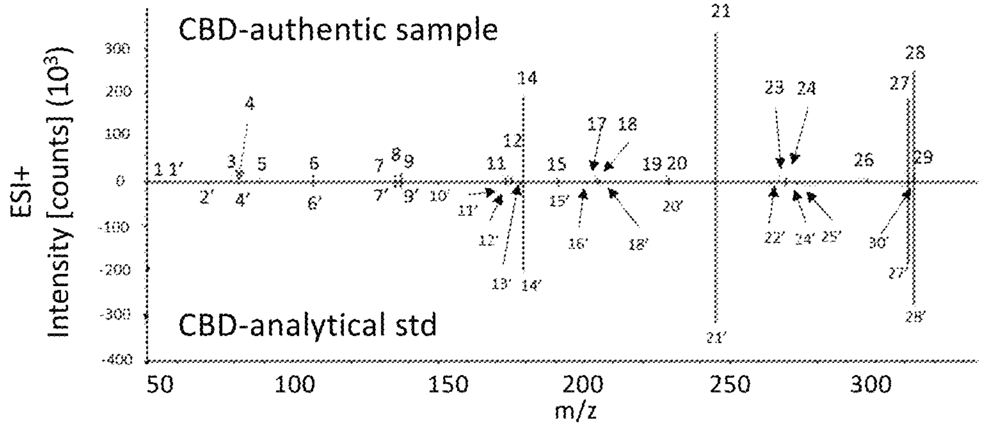
FIG. 4(B) shows match of MS/MS spectra of CBD in authentic samples and reference analytical standard in negative ionization mode by UHPLC-HESI-Orbitrap, according to an exemplary embodiment of the present disclosure.
Figure 5A:
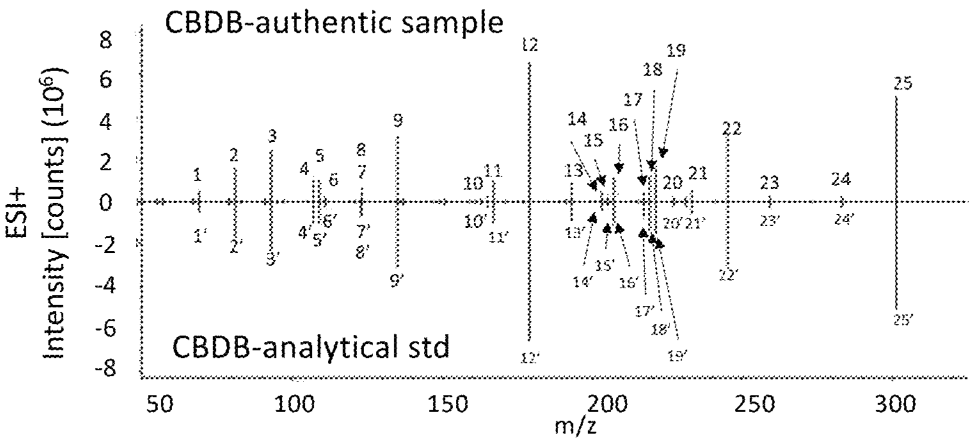
FIG. 5(A) shows match of MS/MS spectra of CBDB in authentic samples and reference analytical standard (synthetic CBDB) in positive ionization mode by UHPLC-HESI-Orbitrap, according to an exemplary embodiment of the present disclosure.
Figure 5B:
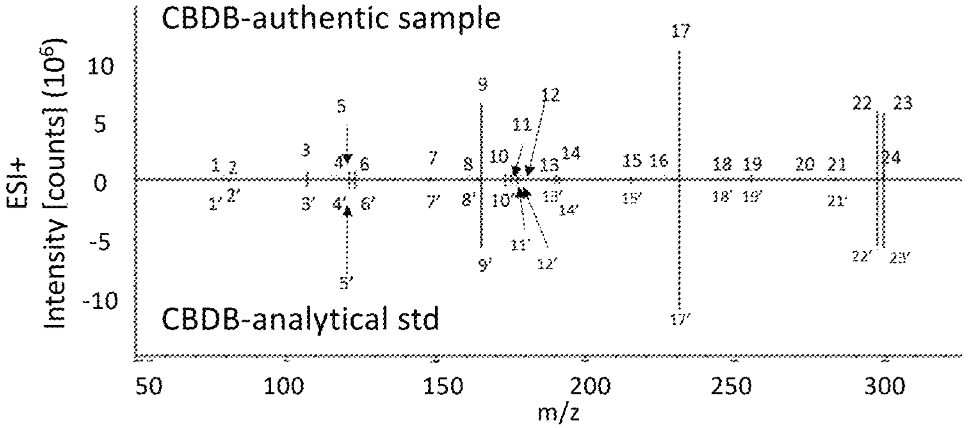
FIG. 5(B) shows match of MS/MS spectra of CBDB in authentic samples and reference analytical standard (synthetic CBDB) in negative ionization mode by USPLC-HESI-Orbitrap, according to an exemplary embodiment of the present disclosure.

As shown in FIG. 3, the peak at 2.6 min (impurity 1) corresponds to the ions $[M+H]^+$ with m/z 287.2002 and $[M-H]^-$ with m/z 285.1861. Both MS/MS spectra (ESI+ and ESI−) in FIG. 5 present a perfect match with those of cannabidivarin (CBDV) analyzed in the same conditions. The peak corresponding to this analyte does not present any interfering peak.

Figure 6A:
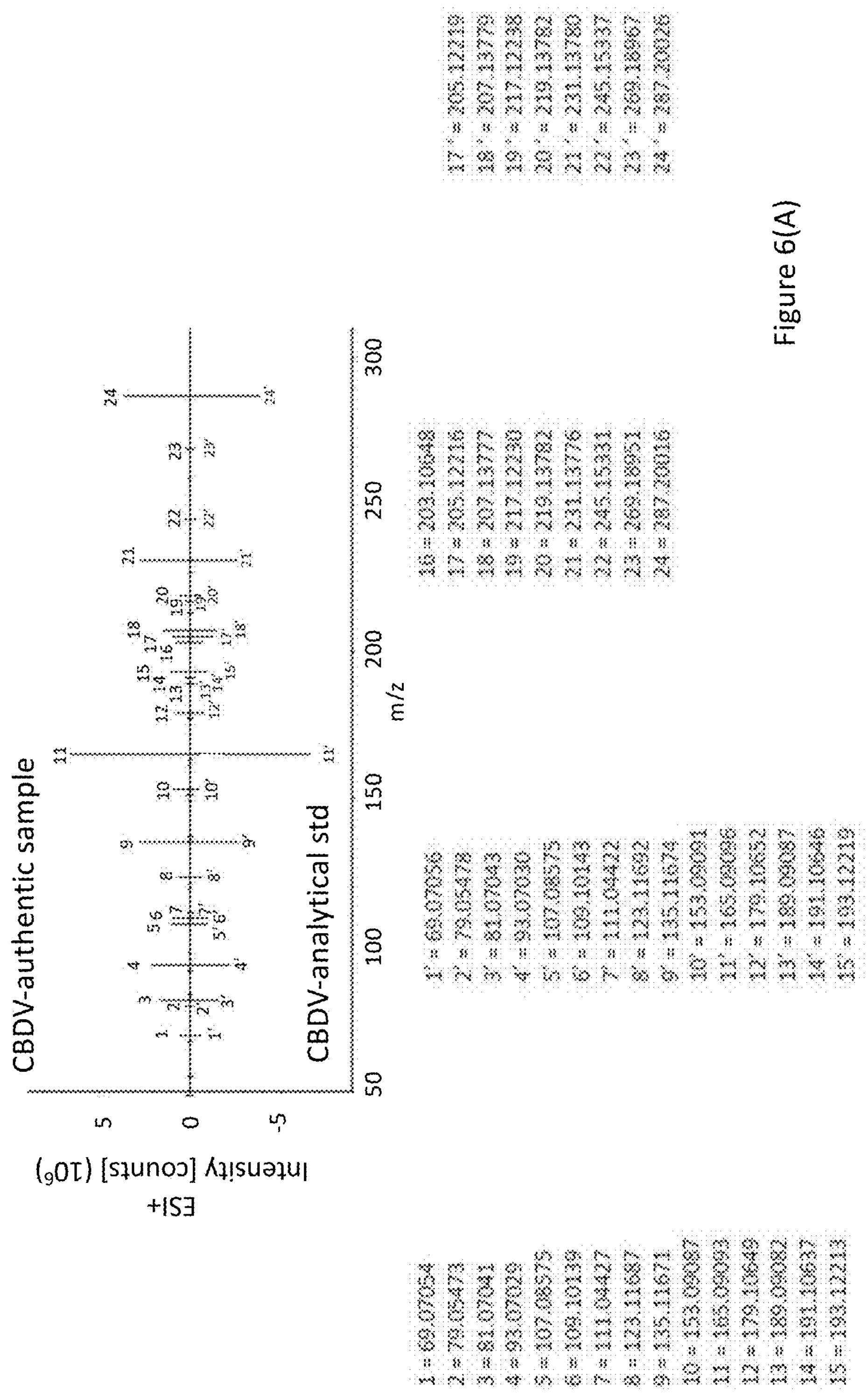
FIG. 6(A) shows match of MS/MS spectra of CBDV in authentic samples and reference analytical standard in positive ionization mode by UHPLC-HESI-Orbitrap, according to an exemplary embodiment of the present disclosure, according to an exemplary embodiment of the present disclosure.
Figure 6B:
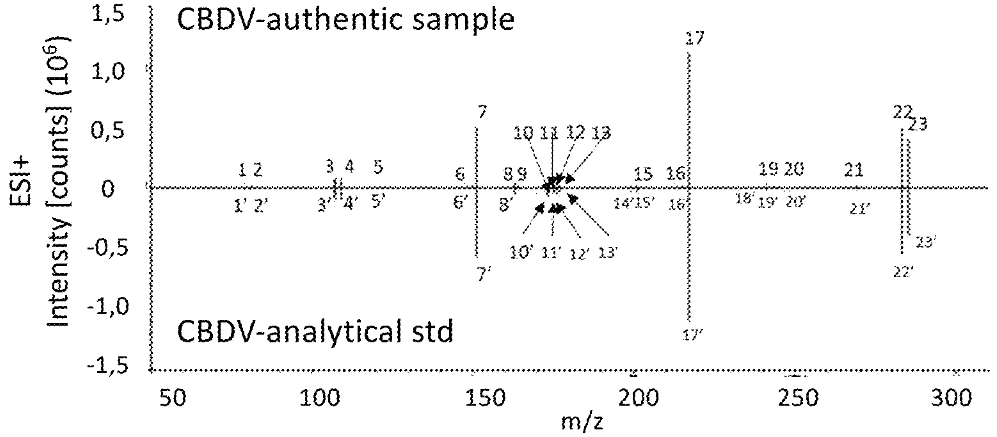
FIG. 6(B) shows match of MS/MS spectra of CBDV in authentic samples and reference analytical standard in negative mode by UHPLC-HESI-Orbitrap, according to an exemplary embodiment of the present disclosure.
Figure 7:
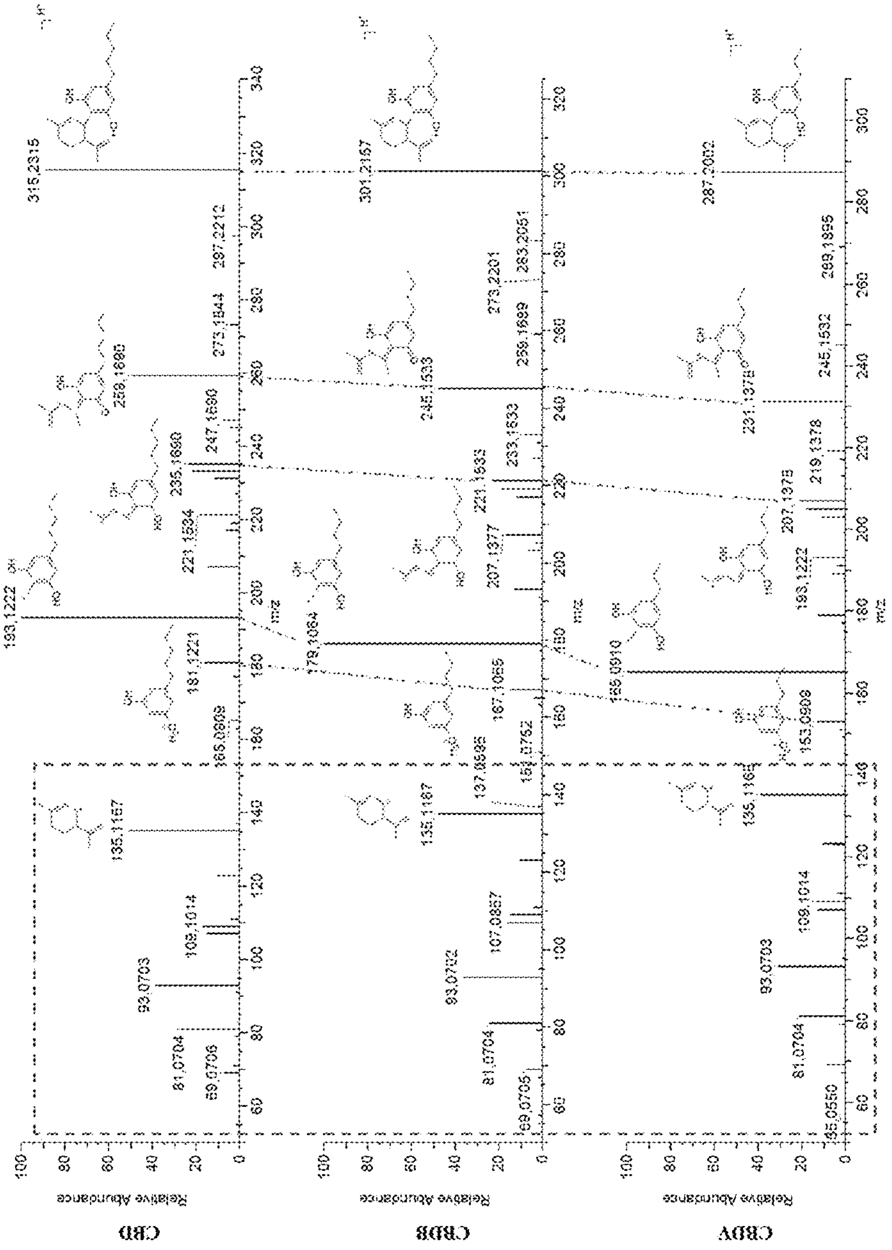
FIG. 7 shows fragmentation pattern of CBD, CBDB and CBDV in positive ionization mode, according to an exemplary embodiment of the present disclosure. The chemical protonated structure is indicated for the main fragments. Red dashed lines indicate the matching fragments between the three cannabinoids. The blue dashed box includes the unchanged fragments belonging to the terpene moiety, according to an exemplary embodiment of the present disclosure.
Figure 8:
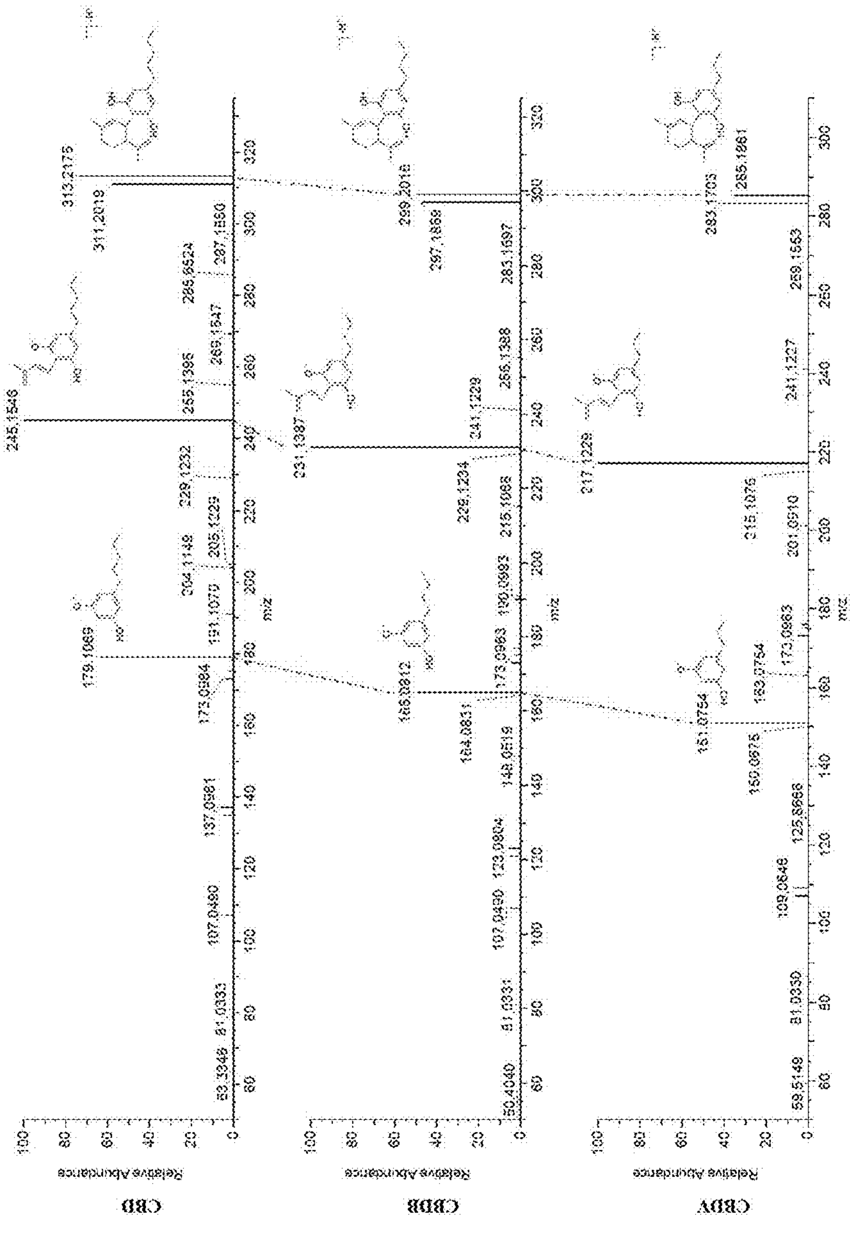
FIG. 8 shows fragmentation pattern of CBD, CBDB and CBDV in negative ionization mode. The chemical ionized structure is indicated for the main fragments. Red dashed lines indicate the matching fragments between the three cannabinoids, according to an exemplary embodiment of the present disclosure.

The peak at 3.3 min in FIG. 3 (impurity 2) corresponds to the ions $[M+H]^+$ with m/z 301.2157 and $[M-H]^-$ with m/z 299.2016. No interfering peak was detected at the retention time of this compound. Both MS/MS spectra (ESI+ and ESI−) of impurity 2 are shown in FIG. 6. The elution time is between that of CBDV and CBD, indicating that the polarity of the compound is greater than CBD and lower than CBDV. The molecular ions $[M+H]^+$ at m/z 301.2157 and [M−H]− at m/z 299.2016 correspond exactly to one methylene unit ($-CH_2-$) either inserted onto CBDV or removed from CBD. The fragmentation pattern in both ESI+ and ESI− mode corroborates the hypothesis that the difference lies in a methylene unit since both fragments and ion abundance perfectly match with those of CBDV and CBD. As highlighted in FIG. 7, which represents the fragmentation pattern of the three cannabinoids in positive ionization mode, the fragment at m/z 245.1533 in the MS/MS spectrum of impurity 2 has the same ionic abundance of the fragments at m/z 259.1960 and m/z 153.0909 in the MS/MS spectra of CBD and CBDV respectively. These fragments derive from the loss of four carbon units from the terpene moiety. Similarly, the fragment at m/z 221.1533 for impurity 2 derives from the breakage of the terpene group with only four carbon units left, as it also occurs for the fragments at m/z 235.1690 for CBD and m/z 207.1378 for CBDV. The base peak at m/z 179.1064 also differs by one methylene unit from the base peaks at m/z 193.1222 for CBD and m/z 165.0910 for CBDV, and corresponds to the complete loss of the terpene moiety except for one carbon unit. The fragment at m/z 167.1065 derives from the further loss of the last carbon unit of the terpene moiety to give the protonated molecule of resorcinol with four carbon atoms on the alkyl side chain. The corresponding fragments for CBD and CBDV are at m/z 181.1221 and m/z 153.0909, respectively. The other smaller fragments are enclosed in the blue dashed box and correspond to the fragmentation profile of the terpene moiety, which remains unchanged for all three cannabinoids. In a similar way, the fragmentation pattern of impurity 2 in negative ionization mode, shown in FIG. 8, is identical to those of CBD and CBDV differing by a methylene unit. The base peak at m/z 231.1387 in the spectrum of impurity 2 derives from a retro Diels-Alder reaction and loss of a part of the terpene moiety, similarly to the fragments at m/z 245.1546 and m/z 217.1229 for CBD and CBDV respectively. The other important fragment is at m/z 165.0912 deriving from the complete loss of the terpene moiety that leads to the ionized resorcinol molecule. The corresponding fragments for CBD and CBDV are at m/z 179.1069 and m/z 151.0754 respectively. All fragments and molecular ions show the same ionic abundance. These data are in agreement with the hypothesis that impurity 2 is a cannabinoid with molecular formula $C_{20}H_{28}O_2$. The data are also in accordance with the high-resolution mass spectrometry characterization of CBD, CBDB and CBDV reported in the literature [18].

1.3.2 Isolation of Natural CBDB

The isolation of impurity 2 from CBD can give an identification. To this end, a semi-preparative chromatographic method was developed employing a semi-preparative column with a fully porous C18 silica stationary phase (250×10 mm) and a mobile phase composed of ACN and water 70:30 (v/v). This method allowed for the isolation of about 1 mg of impurity 2 starting from 1 g of a commercial hemp derived CBD. The amount of isolated compound resulted sufficient to perform a comprehensive spectroscopic characterization, including NMR, optical rotatory power, UV and CD (Exhibit A—Supporting Information), in order to determine its chemical structure by comparison with the spectroscopic data of synthetic CBDB.

1.3.3 Synthesis of CBDB

To best of our knowledge, the synthesis and full spectroscopy characterization of CBDB has never been reported in the literature and its existence has been hypothesized only by means of MS data. In absence of an analytical standard or any spectroscopic reference of CBDB that could be used for the identification of impurity 2, we synthesized and carried out a full spectroscopic profile of the molecule (−)-trans-CBDB. The latter was prepared by Friedel-Craft allylation of 5-butylbenzene-1,3-diol with (1S,4R)-1-methyl-4-(prop-1-en-2-yl)cycloex-2-enol, using pTSA as catalyst as reported in Scheme 1.

Scheme 1. Reagents and conditions: a) pTSA (0.1 eq.), DCM dry, Argon, -10° C., 1 h 32% yield.

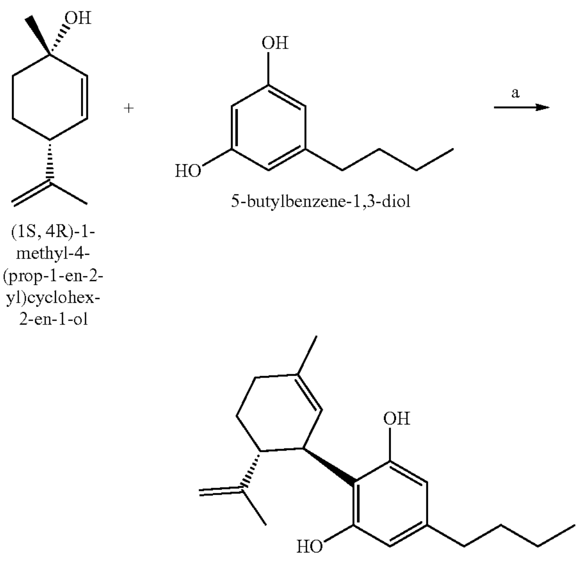

(1S, 4R)-1-methyl-4-(prop-1-en-2-yl)cyclohex-2-en-1-ol 5-butylbenzene-1,3-diol (-)-trans-CBDB

1.3.4 Spectroscopic Characterization of Syn-CBDB and Ext-CBDB

Figure 9A:
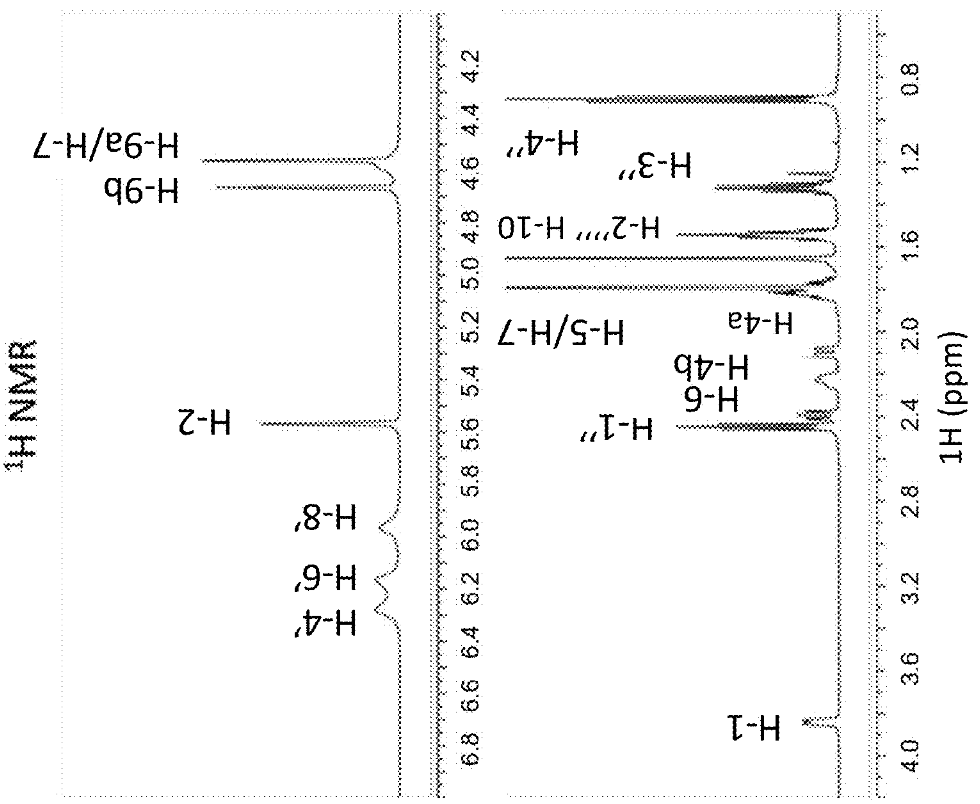
FIG. 9(A) shows $^{1}$H-NMR spectra and peaks assignment for CBDB, according to an exemplary embodiment of the present disclosure.
Figure 9B:
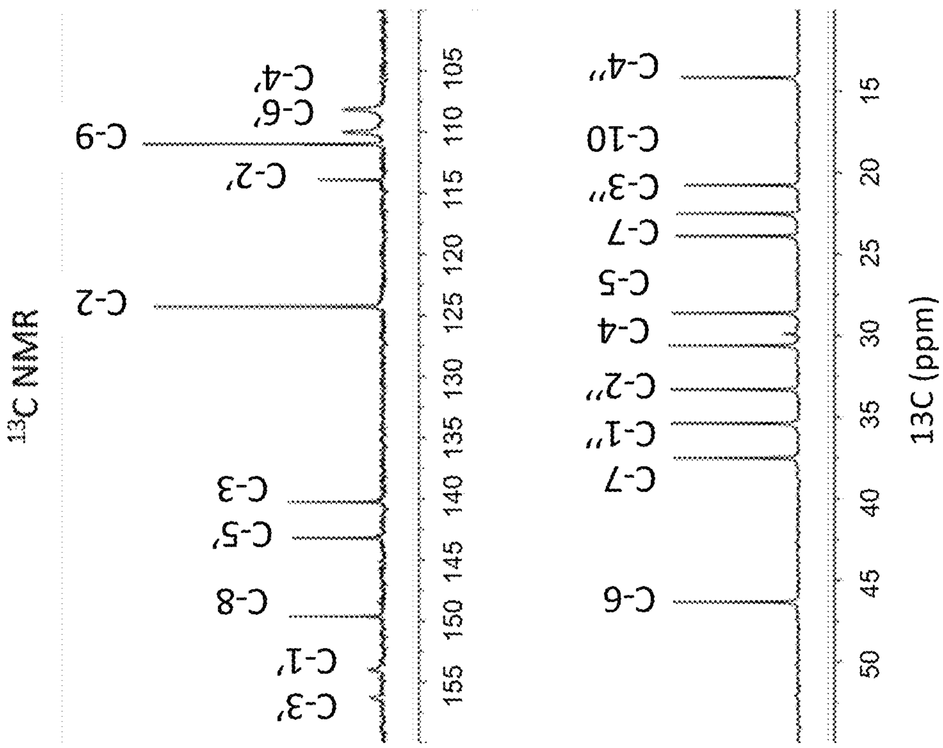
FIG. 9(B) shows $^{13}$C-NMR spectra and peaks assignment for CBDB, according to an exemplary embodiment of the present disclosure.

The chemical identity of synthetic CBDB and its $^{1}$H assignments were achieved by analysing $^{1}$H-NMR, $^{13}$C-NMR and COSY spectra. The protonated carbon atoms were assigned by analysis of the HSQC spectra, and the quaternary carbons were assigned based on HMBC spectra. Table 1 and FIG. 9 show the $^{1}$H and $^{13}$C NMR complete assignments for CBDB, determining the chemical structure of the new synthesized cannabinoid. However, since the molecule of CBDB possesses two stereocenters, it could exist as four possible stereoisomers. The synthetic procedure adopted may have lead to the stereoselective synthesis of (−)-trans-CBDB, and the exact position of the double bonds and the configuration of carbon 1 and 6 were fully investigated and determined by NMR.

Indeed, even though the NMR is not able to discriminate between a couple of enantiomers, a slight shift of the proton signals could be detected among a couple of diastereomers (i.e. cis/trans isomers). Because CBDB and CBD differ only for a methylene in the alkyl chain on the resorcinol moiety, no significative difference in the proton chemical shifts of the terpene moiety may exist among the two molecules. Thus, in order to define first a cis or trans configuration for the synthetic CBDB, we compared its $^{1}$H-NMR with the spectra of (−)-trans-CBD [19] and (−)-cis-CBD [9]. As reported in Table 2, it is possible to observe a close match between the H-1, H-2 and H-6 signals of synthetic CBDB and the corresponding signals of (−)-trans-CBD. In contrast, cis-CBD presents a shielding for H-1 and H-2 (from 3.81-

3.84 to 3.35-3.75 and from 5.54 to 5.40, respectively) and a deshielding for H-6 (from 2.38 to 2.90). These outcomes suggested, therefore, a trans configuration for the synthetic CBDB. However, as trans-CBDB can exist as an enantiomeric couple (1R,6R) or (1S,6S), in order to establish the absolute configuration of C-1 and C-6, the optical rotatory power was determined, resulting in an $[\alpha]_D^{20}=-121°$ (c. 1.6, ACN). This value is in line with the $[\alpha]_D^{20}=-125°$ of (−)-trans-CBD, allowing the assignment of the (1R,6R) absolute configuration and the identification of the synthetic CBDB as (−)-(1R,6R)-CBDB.

Figure 10A:
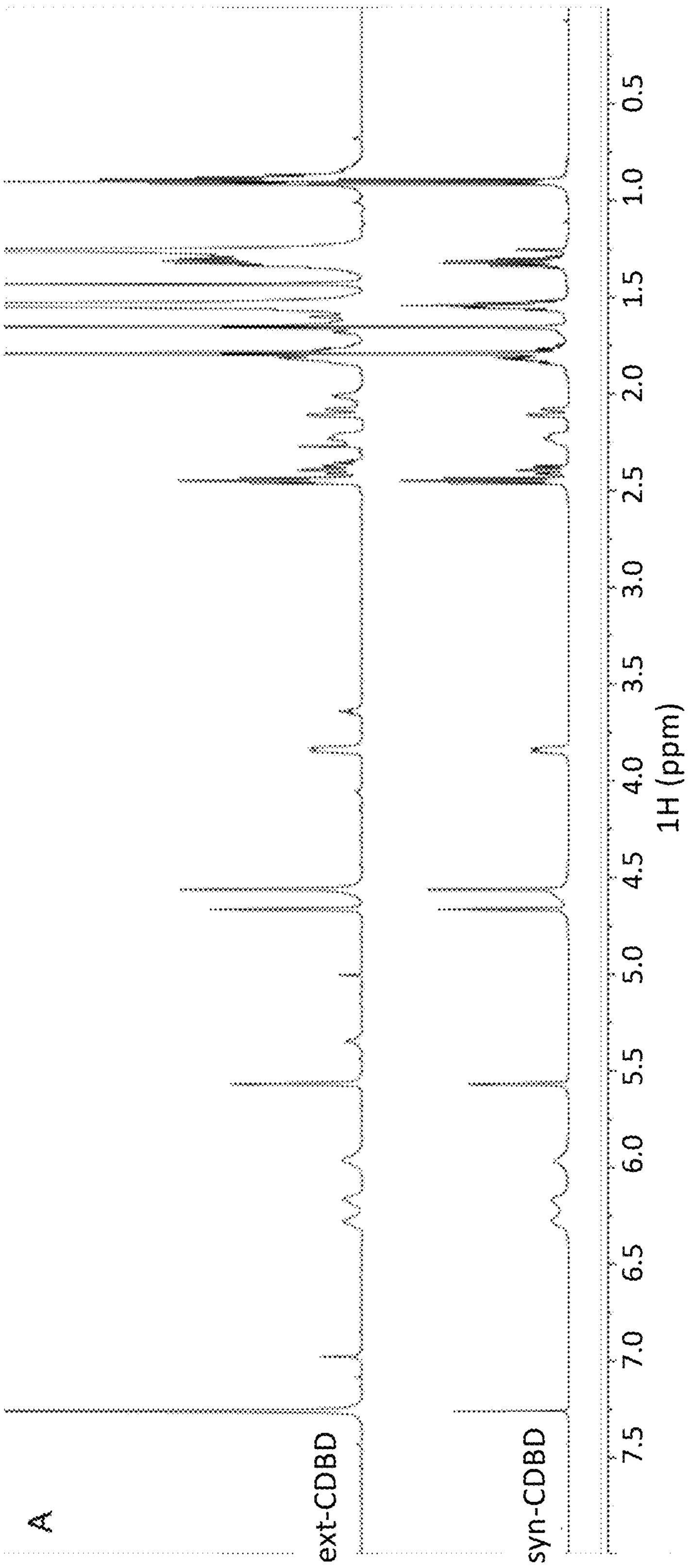
FIG. 10(A) shows superimposition of $^{1}$H-NMR (A) of isolated natural (ext-CBDB, red spectra) and synthesized (syn-CBDB, blue spectra), according to an exemplary embodiment of the present disclosure.
Figure 10B:
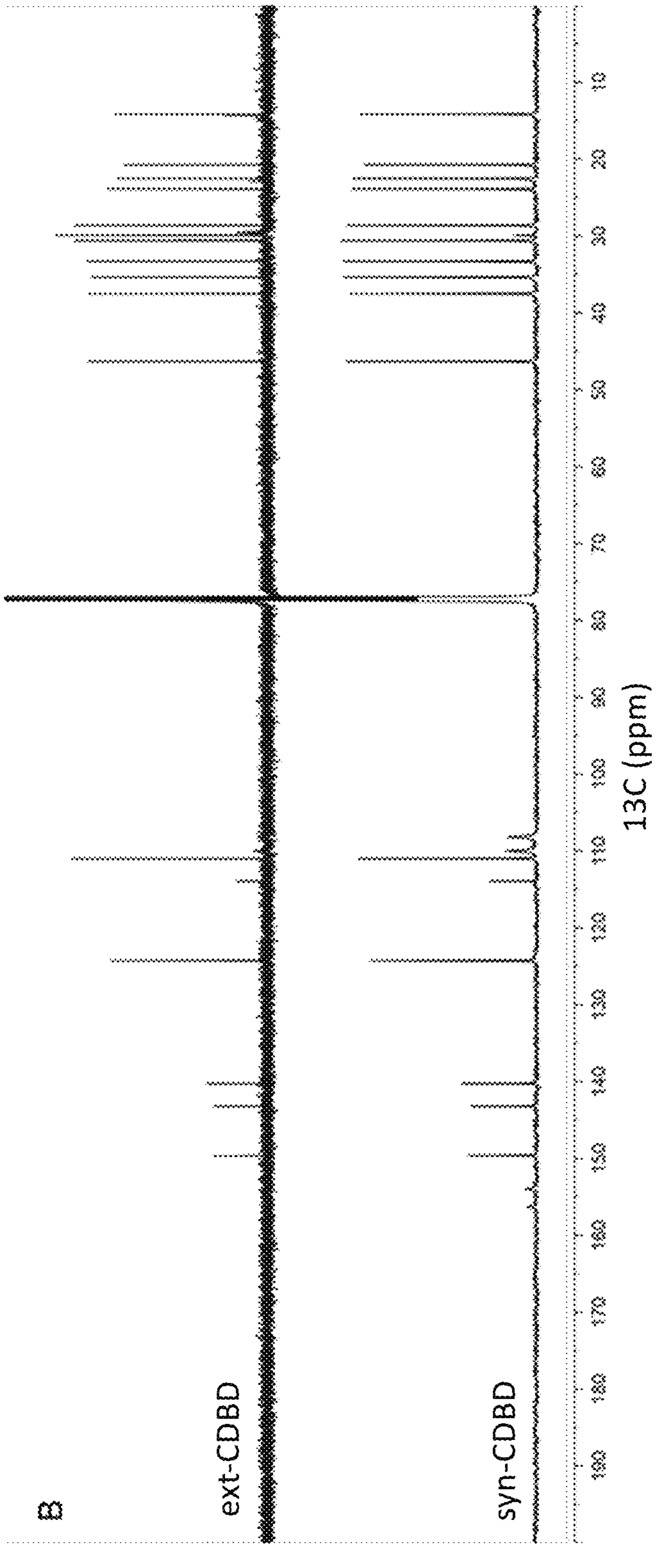
FIG. 10(B) shows superimposition of $^{13}$C-NMR spectra of isolated (ext-CBDB, red spectra) and synthesized (syn-CBDB, blue spectra), according to an exemplary embodiment of the present invention.

Based on the chemical structure and stereochemistry of the synthesized (−)-trans-CBDB, the latter was used as reference compound to determine the identity of the impurity 2. The NMR spectra, UPLC retention time, m/z precursor ions ($[M+H]^+$ and $[M-H]^-$), MS, UV and CD spectra of both synthetic CBDB and impurity 2 (isolated natural CBDB) were compared. As reported in FIG. 10, a perfect superimposition between the spectroscopic data of the two molecules was observed. Moreover, the specific rotatory power of isolated CBDB resulted in an $[\alpha]_D^{20}=-116°$ (c. 0.5, ACN) comparable to the value obtained for the synthetic CBDB. Therefore, based on these considerations, we can state that the impurity 2 present in the CBD extracted from hemp inflorescence is (−)-trans-CBDB.

1.3.5 HPLC-UV Method Development and Validation

Our research group has recently published several works on the development and optimization of analytical methods for the separation of cannabinoids by LC-UV and LC-MS [7, 12, 18, 20-23]. In order to achieve the optimal resolution of the analytes CBDV and CBDB, a core shell column (Poroshell 120 SB-C18, 3.0×150 mm, 2.7 μm) was employed. The mobile phase consisted of 0.1% aqueous formic acid and acetonitrile (30:70, v/v), which allowed for the separation of the analytes within 7 min and of the main peak of CBD within 10 min. FIG. S2 in the Exhibit A—Supplementary Material shows the LC-UV chromatograms of a standard mixture at different concentration levels and an example of an authentic CBD sample. In order to assess the reliability and robustness of the method, a validation according to EMA and ICH guidelines was performed in terms of linearity, selectivity, carryover, accuracy, precision, dilution integrity and stability [16, 17], and the results are described below. The tables of the validation results are reported in the Exhibit A—Supplementary Material.

Linearity. Linearity was assessed for CBDV and CBDB in the ranges 0.28-56.4 μg/mL for CBDV and 0.12-24.0 μg/mL for CBDB. The concentration-response relationship was based on a weighted linear regression ($1/x^2$) in order compensate for the error at low concentrations considering the high dynamic range covered by the calibration curve. The coefficient of determination ($R^2$) was found above 0.999 for both analytes CBDV and CBDB, thus the correlation of concentration vs UV response was considered linear in the specified range (Table S1).

Limit of quantification (LOQ) and limit of detection (LOD). LOD was calculated as described in the methods section and was found 0.10 μg/mL for CBDV and 0.04 μg/mL for CBDB. The LLOQ, which is also the lowest calibration point was 0.28 μg/mL for CBDV and 0.12 μg/mL for CBDB. The ULOQ was set 10% above the highest concentration found for the analytes by injecting a high concentration CBD sample (10 mg/mL). Considering that the highest concentration of CBDV and CBDB in that concentrated CBD sample was 51.0 and 21.0 μg/mL, respectively, the ULOQ was set at 56.4 and 24.0 μg/mL for CBDV and CBDB, respectively.

Autosampler carryover. The analyses performed to assess the autosampler carryover indicated that the peak area corresponding to the analytes was not greater than 17% of the LLOQ and it was totally absent for the IS, thus ensuring good reliability of the quantification of the analytes.

Accuracy and precision (CV). Intra-day accuracy ranged from 98.23 to 104.9% for CBDV and from 100.3 to 105.5% for CBDB. Intra-day precision, expressed as coefficient of variation (CV), was found in the range 0.98-2.25% for CBDV and in the range 1.62-12.0% for CBDB. Inter-day accuracy ranged from 102.0 to 109.0% for CBDV and from 91.67 to 102.0% for CBDB. Inter-day CV was in the range 0.96-2.76% for CBDV and in the range 2.37-9.14% for CBDB. The acceptance criteria of EMA guidelines are established in the range 85-115% for accuracy and below 15% for CV (Table S2). Given the data above, it can be inferred that the developed method is accurate and precise.

Dilution integrity. For dilution integrity accuracy and CV were evaluated across five analyses of a highly concentrated standard mixture of CBDV and CBDB prepared with a concentration three times higher than the ULOQ and diluted to 1/5, 1/10 and 1/20. The accuracies were found in the range 96.72-99.53% for CBDV and in the range 93.47-96.00% for CBDB. The CV was below 3% for both analytes (Table S3). Since accuracy and precision were within ±15% of the nominal concentration, the results met the EMA acceptance criteria, ensuring that samples with concentrations greater than the ULOQ could be diluted and quantified with a good level of confidence. Moreover, this suggests that the calibration range could be extended above the ULOQ set in this method.

Stability. The stability of the analytes was evaluated at two concentration levels, LQC and HQC, at two different temperatures, room temperature (25° C.) and under refrigeration (2-8° C.), in a time interval of 24 hours. The analytes were found stable in both conditions as the calculated concentration was within 5% of the nominal concentration using a freshly prepared calibration curve (Table S4).

1.3.6 Analyses of Authentic CBD Samples

Authentic CBD samples (1 mg/mL), coming from different batches produced according to GMP regulations by hemp extraction and provided by three manufacturers, were analyzed according to the developed HPLC-UV method as described in the experimental section. The results obtained for the concentrations of CBDV and CBDB present in the samples are reported in Table 3. These impurities were present in amounts lower than 0.5%, in particular CBDV was found in the range 0.07-0.41% and CBDB was in the range 0.08-0.19%. The values are extremely variable across the ten samples, most likely because both hemp variety and industrial product manufacturing affect the amount of impurities eventually present in the final product. CBDV has already been detected in several hemp varieties in extremely variable concentrations [7, 24-27]. CBDB was also detected in some hemp varieties but its concentrations have never been determined due to the lack of the corresponding analytical standard [13, 14, 28]. It is reasonable to assume that the concentrations of CBDV and CBDB in CBD samples are a mirror of the concentrations of these analytes in the original plant material from which CBD is extracted. Moreover, since CBD is generally extracted from hemp by crystallization without further purification, the structural similarity of CBDV, CBDB and CBD leads to a co-crystallization of the three compounds. Chromatography would be the only means that can allow to remove such impurities and obtain a 99.99% pure CBD. However, this involves the use of organic solvents, which in turn can be found as a residual impurity in the final product, thus representing a detrimental method from an ecological point of view.

1.4 CONCLUSIONS

One of the major impurities of CBD extracted from hemp, cannabidibutol (CBDB), was fully characterized for the first time. A stereoselective synthesis was developed in order to determine its identity and stereochemistry. This allowed to obtain for the first time the authentic analytical standard, which was employed for the development and validation of an HPLC-UV method for its qualitative and quantitative determination in commercial samples of CBD produced according to GMP regulations. Such standard and analytical method may bridge the gap for pharmaceutical and cosmetic industries that produce CBD. Moreover, although the monograph of CBD in the German DAC code does not mention the presence of either CBDV or CBDB, the latter are the two major impurities in CBD extracted and crystallized from hemp. These two impurities should be included along with the analytical method for their determination in a desirable monograph on CBD of an official pharmacopoeia. Considering that CBDB is present in hemp, as reported by few articles, it may be found also in the acidic form as cannabidibutolic acid (CBDBA), without ruling out the presence of the corresponding ring-closed isomer, tetrahydrocannabutolic acid (THCBA), and of the neutral derivative tetrahydrocannabutol (THCB). The ongoing research in our laboratory aims at identifying these molecules in different *cannabis* varieties.

5. Tables

TABLE 1

$^{1}$H and $^{13}$NMR assignments (δ) of CBDB[a].

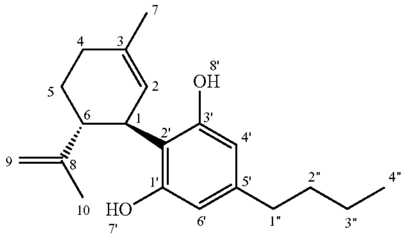

| Position | $^{1}$H-NMR[b] | $^{13}$C-NMR |
|---|---|---|
| 1 | 3.82-3.86 (m) | 37.50 |
| 2 | 5.57 (s) | 124.29 |
| 3 | | 140.25 |
| 4a | 2.08-2.12 (m) | 30.59 |
| 4b | 2.22-2.24 (m) | |
| 5 | 1.76-1.85 (m) | 28.60 |
| 6 | 2.40 (dt) | 46.32 |
| 7 | 1.79 (s) | 23.87 |
| 8 | | 149.62 |
| 9a | 4.56 (s) | 111.01 |
| 9b | 4.67 (s) | |
| 10 | 1.65 (s) | 20.76 |
| 1' | | 154.01 |
| 2' | | 113.92 |

TABLE 1-continued $^{1}$H and $^{13}$NMR assignments (δ) of CBDB[a].

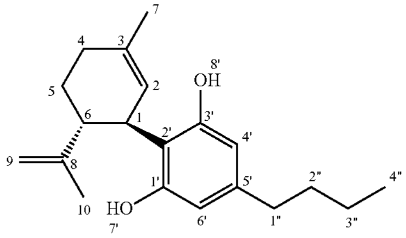

| Position | $^{1}$H-NMR[b] | $^{13}$C-NMR |
|---|---|---|
| 3' | | 156.29 |
| 4' | 6.17 (bs) | 108.17 |
| 5' | | 143.19 |
| 6' | 6.28 (bs) | 110.02 |
| 7' | 4.58 (bs) | |
| 8' | 5.97 (s) | |
| 1" | 2.45 (t) | 35.37 |
| 2" | 1.52-1.57 (m) | 33.29 |
| 3" | 1.32 (sxt) | 22.51 |
| 4" | 0.90 (t) | 14.15 |

[a]NMR spectra were recorded in $CDCl_3$ 99.9% of deuteration on a Bruker 600 spectrometer with $^{1}$H at 600 MHz and $^{13}$C at 151 MHz. Chemical shifts are reported in parts per million (ppm, δ units). Proton chemical shifts were referenced to the solvent residual peak of $CDCl_3$ (7.26 ppm).

[b]Splitting patterns are designed as s, singlet; t, triplet; sxt, sextet; dt, double triplet; m, multiplet; b, broad.

TABLE 2

Comparison between the chemical shift of the proton signals of the terpene moiety among trans-CBDB, trans-CBD and cis-CBD.

| | | $^{1}$H-NMR (δ) | |
|---|---|---|---|
| Position | trans-CBDB | (−)-trans-CBD | (−)-cis-CBD |
| 1 | 3.82-3.86 | 3.81-3.84 | 3.75-3.35 |
| 2 | 5.57 | 5.54 | 5.40 |
| 6 | 2.40 | 2.38 | 2.90 |

TABLE 3

Analysis of authentic CBD samples produced according to GMP regulations. The values are expressed as mean percentage (w/w) of three analyses (n = 3, standard deviation is not indicated as it was lower than 0.0001 for all samples).

| Sample | CBDV (%) | CBDB (%) |
|---|---|---|
| CBD-1 | 0.07 | 0.08 |
| CBD-2 | 0.15 | 0.10 |
| CBD-3 | 0.34 | 0.16 |
| CBD-4 | 0.25 | 0.13 |
| CBD-5 | 0.19 | 0.17 |
| CBD-6 | 0.17 | 0.11 |
| CBD-7 | 0.33 | 0.16 |
| CBD-8 | 0.41 | 0.19 |
| CBD-9 | 0.33 | 0.23 |
| CBD-10 | 0.27 | 0.22 |

1.6 REFERENCES

[1] R. Adams, M. Hunt, J. H. Clark, Structure of Cannabidiol, a Product Isolated from the Marihuana Extract of Minnesota Wild Hemp. I, Journal of the American Chemical Society 62(1) (1940) 196-200.

[2] R. Mechoulam, Y. Shvo, Hashish-I: The structure of Cannabidiol, Tetrahedron 19(12) (1963) 2073-2078.

[3] A. W. Zuardi, Cannabidiol: from an inactive cannabinoid to a drug with wide spectrum of action, Brazilian Journal of Psychiatry 30 (2008) 271-280.
[4] Y. T. Yang, J. P. Szaflarski, The US Food and Drug Administration's Authorization of the First *Cannabis*-Derived Pharmaceutical: Are We Out of the Haze?FDA's Authorization of the First *Cannabis*-Derived PharmaceuticalFDA's Authorization of the First *Cannabis*-Derived Pharmaceutical, JAMA Neurology 76(2) (2019) 135-136.
[5] S. W. Geoffrey Guy, Alice MEAD, Orrin Devinsky, Use of cannabinoids in the treatment of epilepsy, GW Pharma Limited, US, 2016-04-21.
[6] WHO Expert Committee on Drug Dependence, fortieth report, WHO Technical Report Series, N. 1013, Geneva: World Health Organization, 2018, pp. 25-27.
[7] C. Citti, B. Pacchetti, M. A. Vandelli, F. Forni, G. Cannazza, Analysis of cannabinoids in commercial hemp seed oil and decarboxylation kinetics studies of cannabidiolic acid (CBDA), Journal of Pharmaceutical and Biomedical Analysis 149 (2018) 532-540.
[8] D. V. H. C. M. Eiroa Martinez, M. V. Fernandez, G. F. Woerlee, Cannabidiol isolate from industrial-hemp and use thereof in pharmaceutical and/or cosmetic preparations, ECHO Pharmaceuticals B. V., International Patent, 2016-29-09.
[9] T. Petrzilka, W. Haefliger, C. Sikemeier, G. Ohloff, A. Eschenmoser, [Synthesis and optical rotation of the (−)-cannabidiols], Helv Chim Acta 50(2) (1967) 719-723.
[10] S.-H. Baek, M. Srebnik, R. Mechoulam, Boron triflouride etherate on alimina—a modified Lewis acid reagent.: An improved synthesis of cannabidiol, Tetrahedron Letters 26(8) (1985) 1083-1086.
[11] DAC/NRF, DAC C-052: Cannabidiol, NRF 22.10: Ölige Cannabidiol-Lösung 50 mg/ml, Germany, 2015.
[12] C. Citti, D. Braghiroli, M. A. Vandelli, G. Cannazza, Pharmaceutical and biomedical analysis of cannabinoids: A critical review, Journal of Pharmaceutical and Biomedical Analysis 147 (2018) 565-579.
[13] R. Martin Smith, Identification of Butyl Cannabinoids in Marijuana, (1997).
[14] D. J. Harvey, Characterization of the butyl homologues of delta1-tetrahydrocannabinol, cannabinol and cannabidiol in samples of *cannabis* by combined gas chromatography and mass spectrometry, The Journal of pharmacy and pharmacology 28(4) (1976) 280-5.
[15] M. M. Eiras, D. N. de Oliveira, M. S. Ferreira, M. Benassi, S. O. S. Cazenave, R. R. Catharino, Fast fingerprinting of cannabinoid markers by laser desorption ionization using silica plate extraction, Analytical Methods 6(5) (2014) 1350-1352.
[16] ICH Harmonised Tripartite Guideline. Validation of Analytical Procedures: Text and Methodology Q2(R1), 2005.
[17] European Medicines Agency. Guideline on bioanalytical method validation, 2012.
[18] C. Citti, P. Linciano, S. Panseri, F. Vezzalini, F. Forni, M. A. Vandelli, G. Cannazza, Cannabinoid Profiling of Hemp Seed Oil by Liquid Chromatography Coupled to High-Resolution Mass Spectrometry, Frontiers in Plant Science 10(120) (2019).
[19] Z. P. Shultz, G. A. Lawrence, J. M. Jacobson, E. J. Cruz, J. W. Leahy, Enantioselective Total Synthesis of Cannabinoids-A Route for Analogue Development, Organic Letters 20(2) (2018) 381-384.
[20] C. Citti, G. Ciccarella, D. Braghiroli, C. Parenti, M. A. Vandelli, G. Cannazza, Medicinal *cannabis*: Principal cannabinoids concentration and their stability evaluated by a high performance liquid chromatography coupled to diode array and quadrupole time of flight mass spectrometry method, Journal of Pharmaceutical and Biomedical Analysis 128 (2016) 201-209.
[21] C. Citti, F. Palazzoli, M. Licata, A. Vilella, G. Leo, M. Zoli, M. A. Vandelli, F. Forni, B. Pacchetti, G. Cannazza, Untargeted rat brain metabolomics after oral administration of a single high dose of cannabidiol, Journal of Pharmaceutical and Biomedical Analysis 161 (2018) 1-11.
[22] C. Citti, U. M. Battisti, D. Braghiroli, G. Ciccarella, M. Schmid, M. A. Vandelli, G. Cannazza, A Metabolomic Approach Applied to a Liquid Chromatography Coupled to High-Resolution Tandem Mass Spectrometry Method (HPLC-ESI–HRMS/MS): Towards the Comprehensive Evaluation of the Chemical Composition of *Cannabis* Medicinal Extracts, Phytochemical Analysis 29(2) (2018) 144-155.
[23] F. Palazzoli, C. Citti, M. Licata, A. Vilella, L. Manca, M. Zoli, M. A. Vandelli, F. Forni, G. Cannazza, Development of a simple and sensitive liquid chromatography triple quadrupole mass spectrometry (LC-MS/MS) method for the determination of cannabidiol (CBD), Δ9-tetrahydrocannabinol (THC) and its metabolites in rat whole blood after oral administration of a single high dose of CBD, Journal of Pharmaceutical and Biomedical Analysis 150 (2018) 25-32.
[24] F. Pollastro, O. Taglialatela-Scafati, M. Allarà, E. Muñoz, V. Di Marzo, L. De Petrocellis, G. Appendino, Bioactive Prenylogous Cannabinoid from Fiber Hemp (*Cannabis sativa*), Journal of Natural Products 74(9) (2011) 2019-2022.
[25] P. Berman, K. Futoran, G. M. Lewitus, D. Mukha, M. Benami, T. Shlomi, D. Meiri, A new ESI-LC/MS approach for comprehensive metabolic profiling of phytocannabinoids in *Cannabis*, Scientific Reports 8(1) (2018) 14280.
[26] K. W. Hillig, P. G. Mahlberg, A chemotaxonomic analysis of cannabinoid variation in *Cannabis* (Cannabaceae), American Journal of Botany 91(6) (2004) 966-975.
[27] P. Morales, P. H. Reggio, N. Jagerovic, An Overview on Medicinal Chemistry of Synthetic and Natural Derivatives of Cannabidiol, Frontiers in Pharmacology 8(422) (2017).
[28] L. O. Hanuš, S. M. Meyer, E. Muñoz, O. Taglialatela-Scafati, G. Appendino, Phytocannabinoids: a unified critical inventory, Natural Product Reports 33(12) (2016) 1357-1392.

Example 2

Isolation of a High Affinity Cannabinoid for Human CB1 Receptor from a Medicinal *Cannabis* Variety: $\Delta^9$-Tetrahydrocannabutol, the Butyl Homologue of $\Delta^9$-Tetrahydrocannabinol Abtract: The butyl homologues of $\Delta^9$-tetrahydrocannabinol, $\Delta^9$-tetrahydrocannabutol ($\Delta^9$-THCB), and of cannabidiol, cannabidibutol (CBDB), were isolated from a medicinal *cannabis* variety (FM2) inflorescence. A comprehensive spectroscopic characterization, including NMR, UV, IR, circular dichroism and high-resolution mass spectrometry, were carried out on both cannabinoids. The chemical structure and absolute configuration of the isolated cannabinoids were determined by match with the spectroscopic data of the respective compounds obtained by stereoselective synthesis. The butyl homologue of $\Delta^9$-THC, $\Delta^9$-THCB, showed an affinity for the human CB1 ($K_i$=15 nM) and CB2 receptors ($K_i$=51 nM) comparable to that of (−)-trans-$\Delta^9$-THC. Docking studies suggested the key bonds responsible for THC-like binding affinity for CB1. The formalin test in vivo was performed on the two compounds in order to reveal possible analgesic and anti-inflammatory properties. The tetrad test in mice showed a partial agonistic activity of $\Delta^9$-THCB towards CB1 receptor.

2.1 INTRODUCTION $\Delta^9$-Tetrahydrocannabinol ($\Delta^9$-THC) and cannabidiol (CBD) are two active principles of *Cannabis sativa* L. (FIG. 11), a plant used for a plethora of medicinal and nutraceutical properties.[1,2] The use of *cannabis* extracts has been approved by several countries for the treatment of a series of pathological conditions, such as chronic pain and pain associated with multiple sclerosis and spinal cord injury; nausea and vomiting caused by chemotherapy, radiotherapy, HIV therapies; lack of appetite in patients with cachexia, anorexia, chemotherapy or those with AIDS and anorexia nervosa; glaucoma; Tourette syndrome.[3-6] Δ9-THC and CBD are present in different ratios of concentrations according to the *cannabis* variety. Indeed, specific varieties have been selected to produce predominantly THC leaving CBD levels below 1% (w/w), and vice versa. Alternatively, some pathologies may require the treatment with *cannabis* varieties containing balanced levels of both cannabinoids.[7, 8] To this end, some companies have developed a number of certified varieties with standardized concentrations of THC and CBD. For example, in The Netherlands the company Bedrocan produces five varieties: Bedrocan (22% THC, <1% CBD), Bedica (14% THC, <1% CBD, indica), Bedrobinol (14% THC, <1% CBD, sativa), Bediol (6.3% THC, 8% CBD), and Bedrolite (<1% THC, 9% CBD). In Italy, the Military Chemical-Pharmaceutical Institute currently produces two varieties named FM1 (13-20% THC, <1% CBD) and FM2 (5-8% THC, 7-12% CBD). Canada has several licensed producers of medicinal *cannabis*, including Canopy Growth Corporation, Aurora *Cannabis* Enterprises Inc., MedRelief Corp, Tilray and many others; each of them has developed its own varieties. Different variety means different concentrations of the active principles, which includes mainly THC and CBD, but also other cannabinoids with lower concentrations but endowed of several pharmacological properties. Many reports are devoted to the determination of cannabinoids in different *cannabis* varieties.[9-16] Metabolomics is a useful tool that allows for the detection and identification of a great number of compounds simultaneously.[9, 17, 18] Metabolomics has been successfully applied in the past fifteen years in the field of plant science and has led to huge progresses in the knowledge of *cannabis* constituents.[9, 19-24] Our research group has devoted great effort to the development of suitable analytical methods for the qualitative and quantitative determination of cannabinoids in different matrices, spanning medicinal preparations, food products and animal tissues.[14, 22-26] Our most recent work has regarded the development of an analytical method for the determination of a novel homologue of CBD with a 4-term alkyl side chain instead of a pentyl chain named cannabidibutol (4-butyl-5'-methyl-2'-(prop-1-en-2-yl)-1',2',3',4'-tetrahydro-[1,1'-biphenyl]-2,6-diol, CBDB).[27, 28] Although CBDB (FIG. 11) has been previously detected in some *cannabis* varieties by metabolomics-based techniques,[29, 30] only recently our research group fully characterized this cannabinoid for the first time.[27,28] CBDB was isolated from CBD samples extracted from industrial hemp, suggesting that it should be present in the original plant material. As for the other cannabinoids, *cannabis* plant may produce the acidic form of CBDB that is cannabidibutolic acid (CBDBA), which is then converted to its neutral counterpart via a decarboxylation reaction triggered by heat (FIG. 11).[31] THC rich *cannabis* varieties should contain, although in relatively small amount, the ring closed homologues of CBDB and CBDBA, $\Delta^9$-tetrahydrocannabutol ($\Delta^9$-THCB) and tetrahydrocannabutolic acid (THCBA) (FIG. 11). Before this work, $\Delta^9$-THCB has been already detected in *cannabis* plant material, along with CBDB, but it has been characterized only by its mass spectrometric profile.[29,32,33]

The metabolomics analysis of ethanolic extracts of different varieties of the species *Cannabis sativa* showed that the FM2 variety presented the highest amounts of butyl derivatives of acidic cannabinoids, particularly higher than the corresponding Dutch strain Bediol (by Bedrocan, The Netherlands). For this reason, FM2 was selected for the isolation of CBD and THC butyl homologues. Chemical and spectroscopic properties of isolated neutral compounds were compared to in house synthesized standards. The latter were then employed for the semi-quantification of CBDB and $\Delta^9$-THCB in authentic FM2 samples. Finally, we tested these compounds in a widely used model of acute inflammatory pain induced by intra-paw formalin injection in order to investigate possible anti-inflammatory and analgesic properties of the compounds under investigation.

Figure 12A:
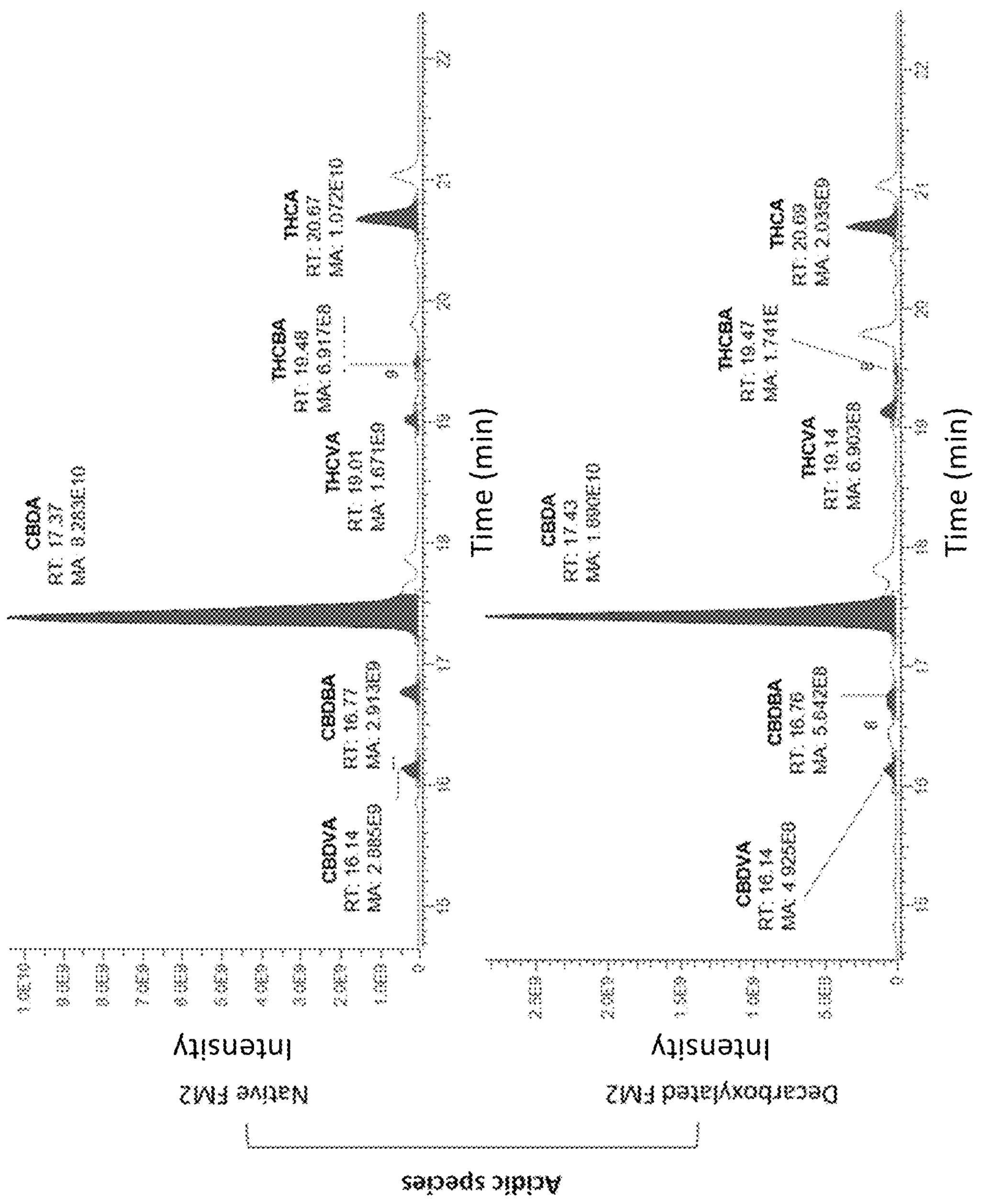
FIGS. 12(A) and 12(B) collectively show shows UHPLC-HRMS chromatograms of an FM2 ethanolic extracts.
Figure 12B:
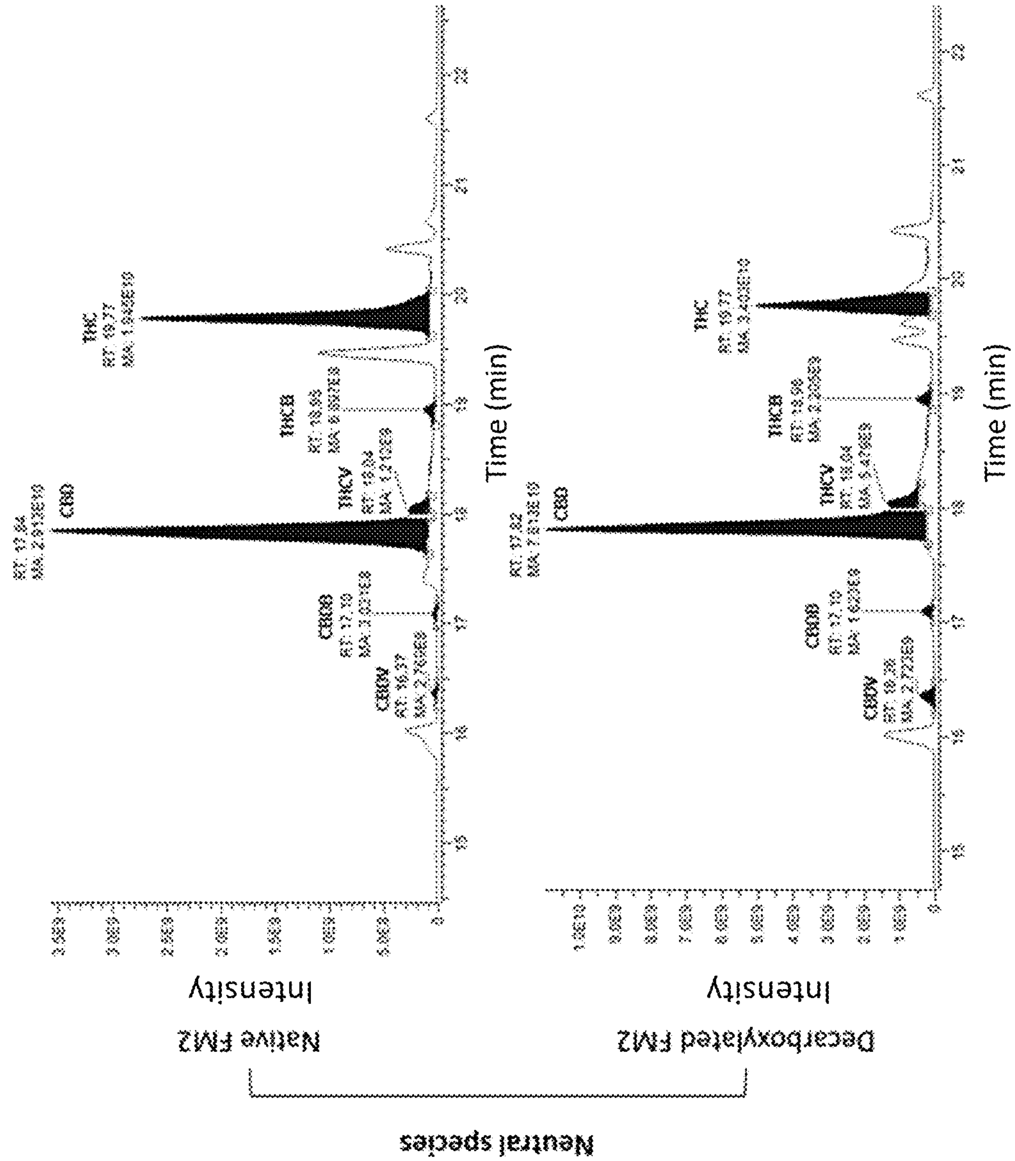

2.2. RESULTS AND DISCUSSION 2.2.1 Characterization of FM2 *Cannabis* Variety by UHPLC-HESI-Orbitrap. The Italian *cannabis* variety FM2 is characterized by a balanced high amount of both THC and CBD. Although these two are the most abundant cannabinoids and their content has been standardized in order to reduce chemical variability of medicinal preparations, other minor cannabinoids are present in the inflorescence. One of the most useful analytical tools for the characterization of an FM2 ethanol extract is represented by the metabolomics approach with the aid of the Orbitrap technology. The accuracy and precision of the high-resolution mass spectrometry (HRMS) is interfaced to a liquid chromatography platform that operates with a sub-3 μm fused-core particle stationary phase, which ensures high efficiency and resolution power with modest back pressures.[14, 22-25, 34, 35] The analysis of the FM2 ethanol extract showed the presence of high amounts of the acidic precursors of CBD and THC, CBDA and THCA, and trace amounts of the neutral species since no decarboxylation process occurred during either the extraction procedure or the storage (FIG. 12). Moreover, CBDA and THCA homologues were also detected in the chromatogram. Specifically, the peak of CBDA (17.4 min) was preceded by the peaks of its propyl and butyl homologues, cannabidivarinic acid (CBDVA) and CBDBA, which eluted at 16.1 min and 16.8 min respectively. Similarly, the peak of THCA (20.7 min) was preceded by the peaks of tetrahydrocannabivarinic acid (THCVA) and THCBA that eluted at 19.0 min and 19.5 min respectively. The identification of THCA, CBDA, THCVA and CBDVA was determined by the analysis of the corresponding analytical standards in the same conditions. However, due to the lack of the analytical standards of CBDBA and THCBA, the structural identification was based on exact mass (Δppm<2) and high-resolution MS/MS spectrum (FIG. S1-6, Exhibit B—Supporting Information). Moreover, given the general difficulty in isolating the acidic forms of cannabinoids, the best way to determine the structural identification is to decarboxylate the native plant material by heat, thus providing the corresponding neutral forms. The decarboxylated inflorescence was extracted as for the native one and subject to UHPLC-HESI-Orbitrap analysis. The peak areas of the acidic species are clearly lower after decarboxylation, while the peak areas of the neutral species showed an increase as a consequence of the conversion of their precursors.

The interpretation of the high-resolution fragmentation spectra determined a four-carbon side chain on the resorcinyl moiety. The precursor ions of the butyl homologues differed by a methylene unit from the pentyl and propyl homologues, as well as the chromatographic retention time, suggested that the lipophilicity of the butyl homologues is intermediate between the propyl and the pentyl ones. CBDA and THCA homologues can be better distinguished by their fragmentation profile in negative ionization mode rather than the one in positive mode. In particular, THCA homologues are generally more poorly fragmented than CBDA homologues in negative ionization mode (FIGS. S1 and S2 respectively, Exhibit B—Supporting Information). HRMS spectra of CBDBA end THCBA in positive ionization mode were also analyzed and compared with their propyl and pentyl homologues (FIG. S3 and S4, respectively, Exhibit B—Supporting Information). Except for the relative abundance (RA) of the fragments, no marked differences could be noted between CBD and THC homologues of the same series (e.g. CBDA and THCA, CBDBA and THCBA, CBDVA and THCVA).

The chromatogram of the decarboxylated extract showed an increase in the peak area of the neutral species. As shown in FIG. 12, the order of elution was: cannabidivarin (CBDV) (16.4 min), CBDB (17.1 min), CBD (17.8 min), $\Delta^9$-tetrahydrocannabivarin ($\Delta^9$-THCV) (18.0 min), $\Delta^9$-THCB (19.0 min) and $\Delta^9$-THC (19.8 min). The identity of CBDV, CBD, $\Delta^9$-THCV and $\Delta^9$-THC was assigned by analysis of the pure analytical standards in the same LC-MS conditions. The analysis of the MS and MS/MS spectra in positive and negative ionization mode of the neutral derivative of CBDBA indicated a perfect match with those of the authentic standard of CBDB synthesized in our previous work.[27] On the other hand, the neutral derivative of THCBA was identified by comparison with its pentyl and propyl counterpart as a pure analytical standard is not available. The MS/MS spectrum of $\Delta^9$-THCB in positive ionization mode is undistinguishable from that of its CBD counterpart,[27] but different in negative ionization mode. The few fragments present in the high-resolution spectrum of $\Delta^9$-THCB in negative mode have low abundance compared to those in the spectrum of CBDB. The spectrum of $\Delta^9$-THCB in positive mode is easily comparable to those of $\Delta^9$-THCV and $\Delta^9$-THC in terms of m/z and RA of the fragments (FIG. S6, Exhibit B—Supporting Information).

2.2.2 Isolation of Natural CBDB and $\Delta^9$-THCB. In order to provide an identification of CBDB and THCB, we isolated the two compounds from decarboxylated FM2 inflorescence by means of semi-preparative liquid chromatography. About 1 mg of pure CBDB and 1 mg of pure $\Delta^9$-THCB were recovered starting from 4 g of decarboxylated plant material. Both compounds were fully characterized by NMR, IR, UV, CD, optical rotation and HRMS. The properties of isolated CBDB were compared to those of the previously synthesized analytical standard,[27,28] thus determining its identity. On the other hand, the pure analytical standard of $\Delta^9$-THCB has never been available. To this end, we developed a stereoselective synthesis of the (6aR,10aR) isomer and carried out the assessment of the structural identity and absolute configuration of the two chiral centers of $\Delta^9$-THCB present in the native *cannabis* inflorescence.

2.2.3 Stereoselective synthesis and spectroscopic characterization of (−)-trans-$\Delta^9$-THCB and matching with extracted $\Delta^9$-THCB. The stereoselective synthesis of (−)-trans-THCB was initially performed by direct condensation of 5-butylbenzene-1,3-diol with (1S,4R)-1-methyl-4-(prop-1-en-2-yl)cycloex-2-enol using $BF_3{\cdot}Et_2O$ or ZnCl2 as Lewis' acid, as already reported in literature for the synthesis of the homologue $\Delta^9$-THC.[36-39] Unfortunately, with these substrates, this procedure led to a complex mixture of isomers of CBDB and $\Delta^9$-THCB resulting in an arduous and low-yield isolation of (−)-trans-$\Delta^9$-THCB by standard chromatographic techniques. Therefore, with the aim to obtain high amount of pure (−)-trans-$\Delta^9$-THCB, the synthetic approach described in Scheme 1 was followed. The Friedel-Craft allylation of 5-butylbenzene-1,3-diol with (1S,4R)-1-methyl-4-(prop-1-en-2-yl)cycloex-2-enol, using pTSA as catalyst, and for a reaction time no longer than 60 minutes, allows to obtain selectively (−)-trans-CBDB, as already reported in our previous work.[27] In contrast, longer reaction times allow the reaction to proceed with the cyclization of CBDB to $\Delta^9$-THCB (not isolable at this stage) and then, quantitatively, to the more thermodynamically stable isomers (−)-trans-A-THCB. By addition of hydrochloric acid to the $\Delta^8$ double bond, using $ZnCl_2$ as catalyst, (−)-trans-$\Delta^8$-THCB was quantitatively converted to (−)-trans-HCl-THCB. Finally, elimination of hydrochloric acid on HCl-THCB, performed with potassium t-amylate as base, occurred selectively in position 2 of the terpene moiety, leading to (−)-trans-$\Delta^9$-THCB in 91% of yield (Scheme 1).

Scheme 1. Synthesis of (-)-trans-$\Delta^9$-THCB.

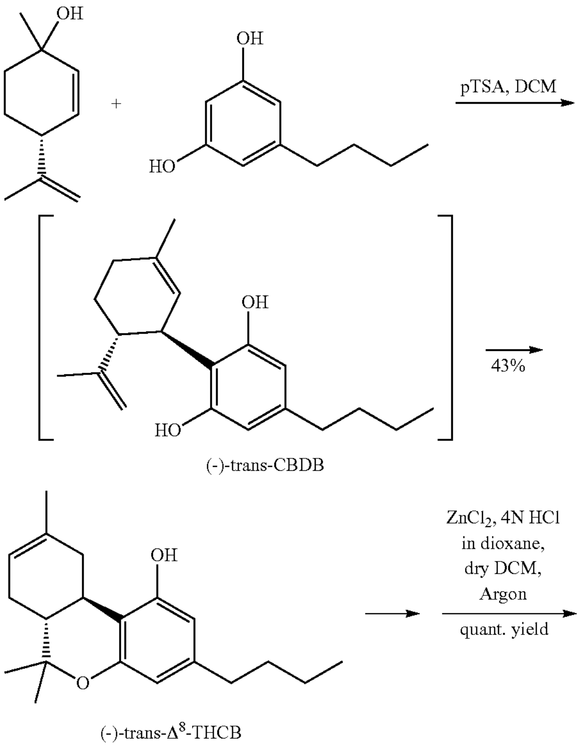

(-)-trans-CBDB (-)-trans-$\Delta^8$-THCB

-continued

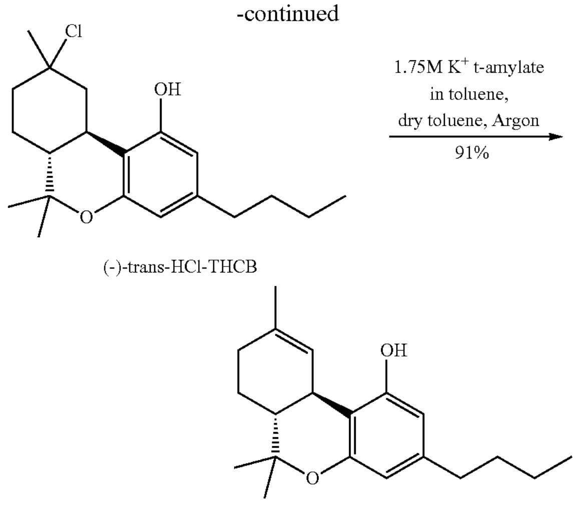

(-)-trans-HCl-THCB (-)-trans-Δ9-THCB

The chemical identity of synthetic (−)-trans-Δ9-THCB and its $^{1}H$ and $^{13}C$ assignments were achieved by analyzing $^{1}H$ and $^{13}C$ NMR spectra. Table 4 and FIG. S1-2 (Exhibit B—Supporting Information) show the $^{1}H$ and $^{13}C$ NMR complete assignments for (−)-trans-Δ9-THCB. The synthetic protocol adopted goes through the synthesis of (−)-trans-CBDB, whose stereochemistry was fully investigated and determined in our previous work[27] and subsequent isomerization to Δ9-THCB. Althought the synthetic conditions may not affect the configuration of the stereocenters of the final (−)-trans-Δ9-THCB,[38, 40] we determined the exact position of the double bonds and the cis/trans configuration of the terpene ring. Since (−)-trans-Δ9-THC with (−)-trans-Δ9-THCB differ only by a methylene in the alkyl chain on the resorcinol moiety, no significant difference in the proton chemical shifts of the terpene moiety may exist between the two molecules. The NMR spectra of (−)-trans-Δ9-THC and (−)-trans-Δ9-THCB were acquired in the same solvent.[41] A near-perfect match in the chemical shift of the two molecules was observed, thus determining the chemical structure of the new synthesized cannabinoid and in particular the Δ9 position of the double bond and the trans configuration of the dihydro-pyran ring. In addition, the exact configuration of carbon 1 and 6 of the synthesized Δ9-THCB was determined by the optical rotatory power. (−)-trans-Δ9-THCB showed an $[\alpha]_D^{20}$−143° in acetonitrile comparable with the $[\alpha]_D^{20}$=−152° in ethanol of (−)-trans-Δ9-THC.[42] Since both molecules resulted levogyre, this suggests that the configuration at carbon 1 and 6 is the same for Δ9-THC and Δ9-THCB, namely (1R, 6R).

TABLE 4

$^{1}H$ and $^{13}$ NMR Assignments (δ) of (−)-trans-Δ9-THCB and (−)-trans-Δ9-THC in $CDCl_3$[a]

| | (−)-trans-Δ9-THCB | | (−)-trans-Δ9-THC[41] | |
|---|---|---|---|---|
| position[b] | $^{1}H$ NMR | $^{13}C$ NMR | $^{1}H$ NMR | $^{13}C$ NMR |
| 1 | — | 154.91 | — | 154.7 |
| 2 | 6.14 (1H, s) | 107.69 | 6.14 (1H, d, J = 1.6 Hz) | 107.5 |
| 3 | — | 142.90 | — | 142.8 |
| 4 | 6.27 (1H, s) | 109.18 | 6.27 (1H, d, J = 1.6 Hz) | 110.1 |
| 4a | — | 154.33 | — | 154.2 |
| 6 | — | 77.35 | — | 76.7 |
| 6a | 1.66-1.72 (1H, m) | 45.95 | 1.69 (1H, m) | 45.8 |
| 7 | a- 1.89-1.93 (1H, m) | 25.16 | a- 1.90 (1H, m) | 25.0 |
| | b- 1.37-1.43 (1H, m) | | b- 1.40 (1H, m) | |
| 8 | 2.15-2.17 (2H, m) | 31.31 | 2.16 (2H, m) | 31.2 |
| 9 | — | 134.54 | — | 134.3 |
| 10 | 6.29 (1H, s) | 123.88 | 6.31 (1H, q, J = 1.6 Hz) | 13.7 |
| 10a | 3.20 (1H, d, J = 12.0 Hz) | 33.72 | 3.20 (1H, d, J = 10.9 Hz) | 33.6 |
| 10b | — | 110.24 | — | 110.8 |
| 11 | 1.68 (3H, s) | 23.50 | 1.68 (3H, s) | 23.4 |
| 12 | 1.41 (3H, s) | 27.71 | 1.41 (3H, s) | 27.6 |
| 13 | 1.09 (3H, s) | 19.41 | 1.09 (3H, s) | 19.3 |
| OH | 4.64 (1H, bs) | — | 4.87 (1H, s) | — |
| 1' | 2.45 (2H, t, J = 8.0 Hz) | 35.31 | 2.42 (2H, td, J = 7.3, 1.6 Hz) | 35.5 |
| 2' | 1.56 (2H, qnt, J = 8.0 Hz) | 33.25 | 1.55 (2H, q, J = 7.8 Hz) | 30.6 |
| 3' | 1.36 (2H, sxt, J = 8.0 Hz) | 22.48 | | 31.5 |
| | | | 1.29 (4H, m) | |
| 4' | 0.90 (3H, t, J = 8.0 Hz) | 14.09 | | 22.5 |
| 5' | N/A | N/A | 0.87 (3H, t, J = 7.0 Hz) | 14.0 |

[a]Chemical shift, in ppm, are referenced to the chloroform residual signal (7.26 ppm for $^{1}H$ and 77.20 ppm for $^{13}C$). Coupling constants are reported in hertz (Hz). Splitting patterns are designed as s, singlet; d, doublet; t, triplet; qnt, quintet; sxt, sextet; m, multiplet; b, broad.

[b]According to dibenzopyran numbering.

N/A. Not applicable

Based on the chemical structure and stereochemistry of synthetic $\Delta^9$-THCB, the latter was used as reference compound to determine the identity of the (−)-trans-$\Delta^9$-THCB identified in FM2 *cannabis* variety. The UHPLC retention time, m/z precursor ions ($[M+H]^+$ and $[M-H]^-$) and fragmentation spectra of both molecules showed a perfect match. Moreover, the comparison of $^1H$ and $^{13}C$ NMR, UV and CD spectra of both synthetic $\Delta^9$-THCB and isolated $\Delta^9$-THCB resulted in a perfect overlap (FIGS. S17-S18, Exhibit B—Supporting Information). Therefore, based on these considerations, we can state that the new identified cannabinoid present in the extracted from FM2 hemp inflorescence is the (−)-trans-$\Delta^9$-THCB.

2.2.4 Binding affinity at human CB1 and CB2 receptors. The binding affinity of (−)-trans-$\Delta^9$-THCB against purified human CB1 and CB2 receptors was determined in a radioligand binding assay. The capability of the ligand to displace radiolabeled [$^3$H] CP55940 or [$^3$H]WIN 55212-2 from CB1 and CB2 receptors, respectively, was measured at ten concentration ranging from 1 nM to 30 uM and the $IC_{50}$ and $K_i$ values were calculated (Table 5 and Exhibit B—Supporting Information). CP55940 (CB1 $IC_{50}$=1.7 nM, CB1 $K_i$=0.93 nM) and WIN 55212-2 (CB2 $IC_{50}$=2.7 nM, CB2 $K_i$=1.7 nM) were used as reference compounds. (−)-trans-$\Delta^9$-THCB binds with high affinity to both human CB1 and CB2 receptors with a $K_i$ of 15 and 51 nM, respectively. Comparing these data with those reported in the literature, (−)-trans-$\Delta^9$-THCB resulted three times more active than (−)-trans-$\Delta^9$-THC ($K_i$=40 nM) and five times more active than (−)-trans-$\Delta^9$-THCV ($K_i$ of 75.4 nM) against CB1 receptor, whereas no significative difference in biding affinity were observed against CB2 receptor for the three cannabinoids.[43]

TABLE 5

Binding Affinity ($IC_{50}$ and $K_i$) of (−)-trans-$\Delta^9$-THCB at human CB1 and CB2 Receptors.

| | hCB1 | | hCB2 | |
|---|---|---|---|---|
| | $IC_{50}$ in nM | $K_i$ in nM | $IC_{50}$ in nM | $K_i$ in nM |
| (−)-trans-$\Delta^9$-THCB | 28 | 15 | 79 | 51 |
| CP 55940 | 1.7 | 0.93 | — | — |
| WIN 55212-2 | — | — | 2.7 | 1.7 |

SD is within ±10% of the value

Figure 13:
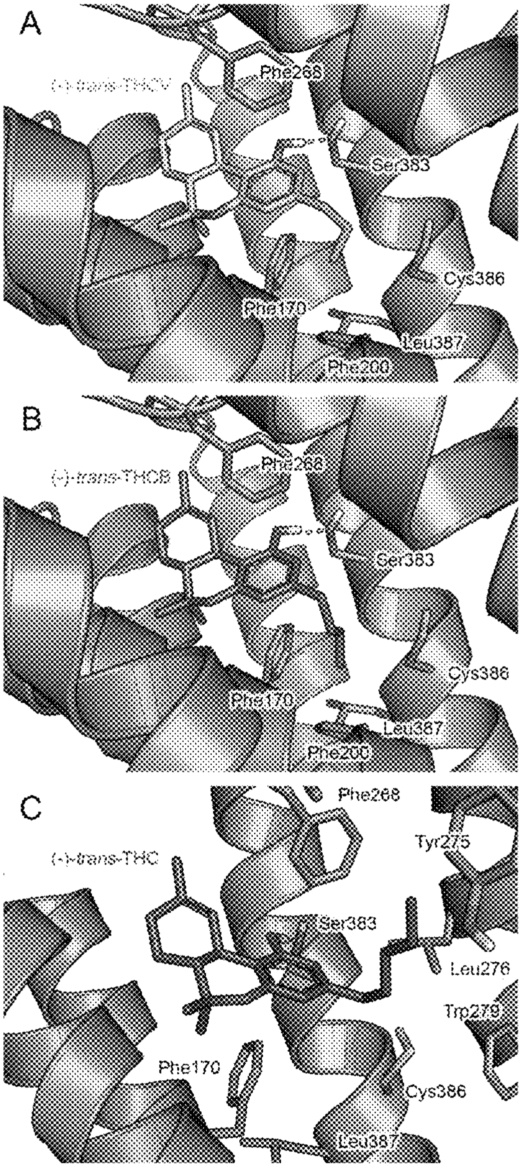
FIG. 13 shows docking pose of (−)-trans-$\Delta^9$-THCV (a, orange sticks), (−)-trans-$\Delta^9$-THCB (B, deep blue sticks) and (−)-trans-$\Delta^9$-THC (C, purple sticks) in complex with CB1 receptor (PDB ID: 5XRA, deep teal cartoon), according to an exemplary embodiment of the present disclosure. Important amino acidic residues are reported in deep teal sticks. H-bond are reported in yellow dotted line. Heteroatoms are colored in red (oxygen), yellow (sulphur).

In order to explore the binding affinity against CB1 receptor, docking simulation for the three THC homologues was performed. The x-ray structure of the active conformation of CB1 receptor in complex with the agonist AM11542 (PDB ID: 5XRA) was used as reference for docking since marked structural changes in the orthosteric ligand-binding site were observed with the respect of the inactive conformation.[44-46] As reported in FIG. 13A-C, the three tetrahydrocannabinols (THC, THCV and THCB) exhibited similar binding poses in the orthosteric ligand-binding site. In particular, no significative differences were observed for the pose of the tetrahydrobenzo[c]chromene core located in the main hydrophobic site. The aromatic ring of resorcinol is involved in an edge-to-face π-π interaction with Phe170 and Phe268, whereas the hydroxyl group is engaged in a H-bond with Ser383 (FIG. 13A-C). The main difference between the three ligands is observed in the position of the aliphatic side chain. Indeed, the pentyl side chain of $\Delta^9$-THC protrudes into the long tunnel formed by helices III, V and VI, undergoing hydrophobic interactions with Leu193, Val196, Tyr275, Leu276, Trp279 and Met363. In contrast, the propyl chain of $\Delta^9$-THCV is located in a small hydrophobic sub-pocket located near the entrance of the tunnel and delimited by Phe170, Phe200, Leu387, Met363, Leu359 and Cys386 (FIG. 13A). This sub pocket accommodates the C1'-gem-dimethyl group introduced in many synthetic cannabinoids, accounting for a notable enhancement in potency and efficacy observed for these homologues.[47-50] Although structure-activity relationship (SAR) studies with classical cannabinoids have shown that the C3 alkyl chain lengths modulate the ligand affinity at CB1 receptor, (−)-trans-$\Delta^9$-THCB was 3-times more active than (−)-trans-$\Delta^9$-THC. Interestingly, from docking calculation the butyl chain of THCB does not extend within the tunnel, such as for THC. In contrast, it accommodates within the sub-pocket, maximizing the hydrophobic interaction with Phe170, Phe200, and Leu387 (FIG. 13B) and accounting for the higher affinity against CB1 than $\Delta^9$-THC and $\Delta^9$-THCV.

2.2.5 Semi-Quantification of CBDB and $\Delta^9$-THCB in the FM2 Variety. The concentration of total CBD and total THC in the FM2 variety measured by gas chromatography coupled to flame ionization detector (GC-FID) provided in the certificate of analysis by the Military Chemical-Pharmaceutical Institute was 59 mg/g and 42 mg/g respectively. In order to provide an approximate concentration of their butyl homologues, a semi-quantitative analysis was carried out by performing an external calibration for each analyte, including CBD, $\Delta^9$-THC, CBDB and $\Delta^9$-THCB. The FM2 ethanol extract was injected into the HPLC-Q-Exactive system and the concentration calculated for CBDB and $\Delta^9$-THCB was 0.5 mg/g and 0.4 mg/g (w/w) respectively. The values obtained for CBD and $\Delta^9$-THC (56 and 39 mg/g respectively) were in accordance with those provided by the Institute of Florence.

Figure 14A:
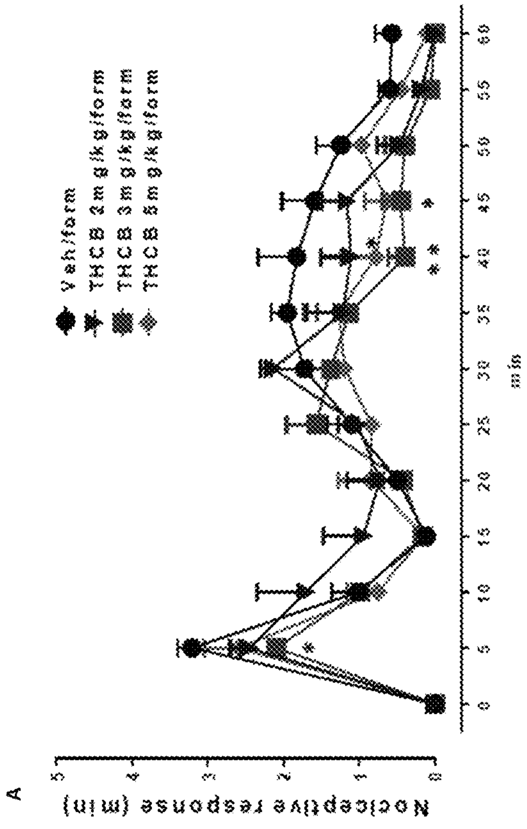
FIG. 14(A) shows the effect of $\Delta^9$-THCB (2, 3 and 5 mg/kg, i.p.) in the formalin test in mice. The total time of the nociceptive response was measured every 5 min and expressed in min (see experimental section), according to an exemplary embodiment of the present disclosure. Data are represented as means±S.E.M. (n=5). * and ** indicate statistically significant differences vs. Veh/form, $p<0.05$ and $p<0.01$ respectively.
Figure 14B:
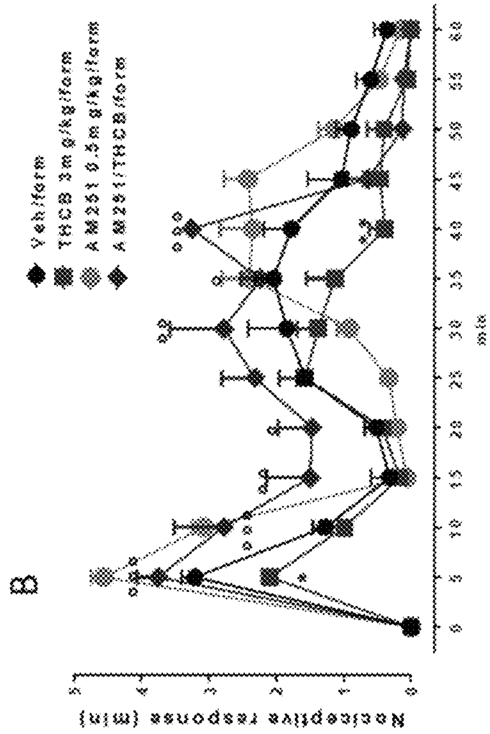
FIG. 14(B) shows the effect of AM251 (0.5 mg/Kg i.p.) $\Delta^9$-THCB (3 mg/kg, i.p.) in the formalin test in mice, according to an exemplary embodiment of the present disclosure. The total time of the nociceptive response was measured every 5 min and expressed in min (see methods). Data are represented as means±S.E.M. (n=5). * and ** indicate statistically significant differences vs. Veh/form, $p<0.05$ and $p<0.01$ respectively. ○, ○ and ○○○ indicate statistically significant differences vs THCB, $p<0.05$, $p<0.01$ and $p<0.001$, respectively., according to an exemplary embodiment of the present disclosure.
Figure 14C:
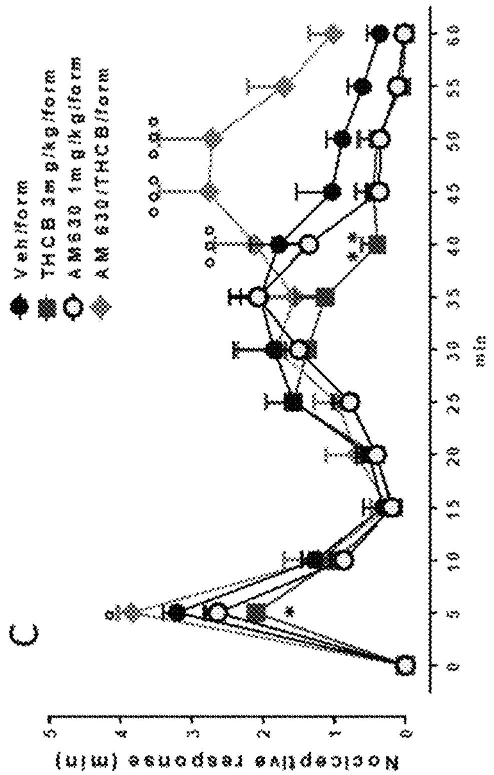
FIG. 14(C) shows the effect of AM630 (1 mg/kg i.p.) $\Delta^9$-THCB (3 mg/kg, i.p.) in the formalin test in mice, according to an exemplary embodiment of the present disclosure. The total time of the nociceptive response was measured every 5 min and expressed in min (see methods). Data are represented as means±S.E.M. (n=5). * and  indicate statistically significant differences vs. Veh/form, $p<0.05$ and $p<0.01$ respectively. ○, ○○○ and ○○○ indicate statistically significant differences vs THCB, $p<0.05$, $p<0.01$ and $p<0.001$, respectively., according to an exemplary embodiment of the present disclosure.

2.2.6 Effect of the new compounds on the formalin test in mice. Nociceptive response to subcutaneous formalin induced an early, short lasting first phase (0-7 min) followed by a quiescent period and then a second, prolonged phase (15-60 min) of tonic hyperalgesia. Systemic administration of $\Delta^9$-THCB (3 mg/kg, i.p.) ($F_{(3,12)}$=2.09 P=0.15) reduced both first and second phase of formalin test (FIG. 14A). Pre-treatment with both AM251 ($F_{(3,12)}$=6.23 P=0.01) and AM630 ($F_{(3,12)}$=4.14 P=0.03) prevented the analgesic effects induced by $\Delta^9$-THCB (FIG. 14B-C). These data suggest that the pharmacological effect of $\Delta^9$-THCB is likely to be mediated by the cannabinoid system. Interestingly, the effect on the first phase of the formalin test, could also suggest us that other mechanisms at the basis of $\Delta^9$-THCB pharmacological action might be involved. The possible involvement of other receptors such as Transient Receptors Potential channels family (TRPs) might also explain, at least in part, biphasic effect at different doses.[51] Indeed, $\Delta^9$-THCB is effective at 3 mg/Kg, whereas its pharmacological effect in preventing formalin-induced nocifensive behavior is similar or even reduced. Further studies may be investigate the potential effect of this compound on other type of chronic pain including neuropathic pain.

Figure 15A:
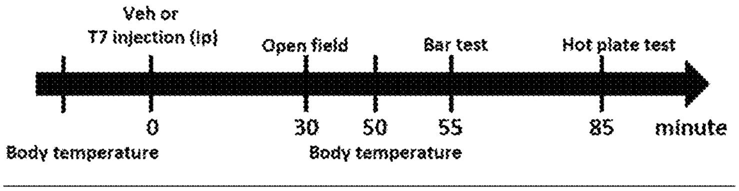
Figure 15B:
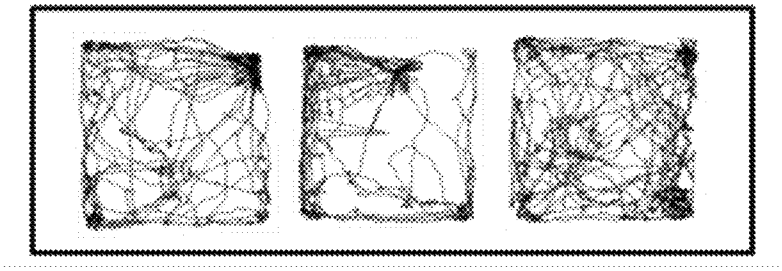
Figure 15C:
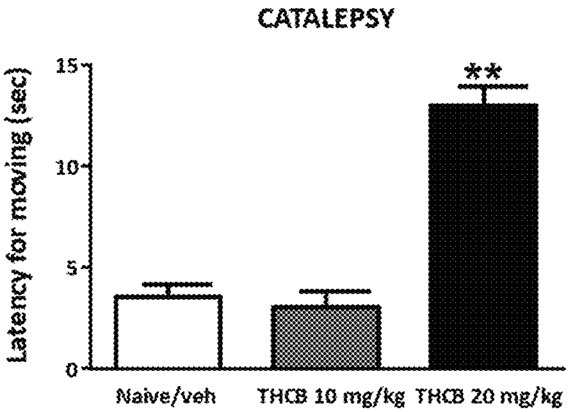
Figure 15D:
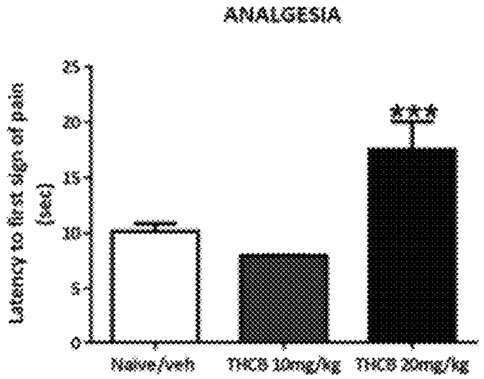
Figure 15E:
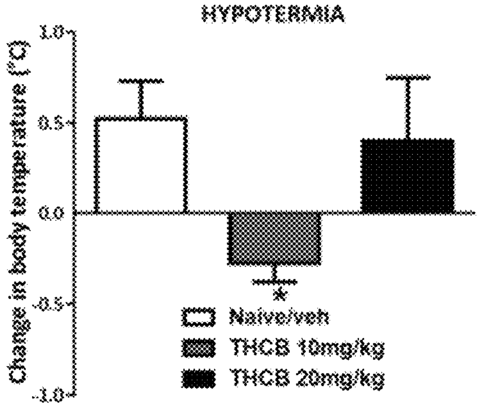
Figure 15F:
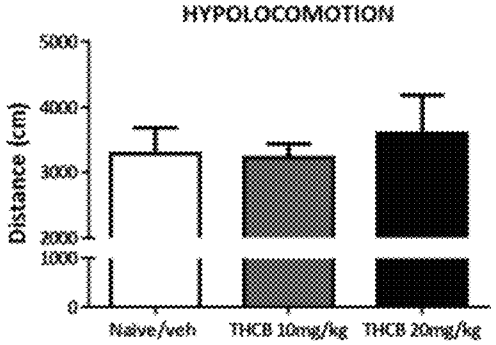
FIG. 15(F) shows analgesia (latency to first sign of pain, s) in the hot plate test, according to an exemplary embodiment of the present disclosure. Data in FIGS. 15(A)-(E) are represented as mean±SEM of 4 mice per group. * indicates significant differences compared to 0 (vehicle injection); specifically: *$p<0.05$, $p<0.01$, *$p<0.001$ vs. vehicle and the Kruskall-Wallis test followed by Dunn's post hoc tests was used for statistical analysis.

2.2.7 In vivo determination of the cannabimimetic profile of $\Delta^9$-THCB. The cannabinoid activity of $\Delta^9$-THCB was evaluated by the tetrad of behavioral tests on mice. The tetrad includes the assessment of spontaneous activity, immobility index (catalepsy), analgesia and changes in rectal temperature. Decrease of locomotor activity, catalepsy, analgesia and hypothermia are well-known signs of physiological manifestations of cannabinoid or cannabimimetic activity. After intraperitoneal (i.p.) administration (FIG. 15A), $\Delta^9$-THCB at 10 and 20 mg/kg did not show any alteration on the spontaneous activity of mice in the open field, (FIG. 15B) (Naïve/veh: 3283 cm±390.5, 10 mg/kg:

3220 cm±212.4, 20 mg/kg: 3591 cm±597.9, P=0.7061). Moreover, $\Delta^9$-THCB administration induced a significant increase, only at 20 mg/kg, in the latency for moving from the catalepsy bar (FIG. 15C) (Naïve/veh: 3.50 sec±0.65, 10 mg/kg: 3.0 sec±0.82, 20 mg/kg: 13.0 sec±0.91, P=0.0074). In the hot plate test (FIG. 15F), $\Delta^9$-THCB administration (only at 20 mg/kg) induced a significant antinociceptive effect as compared to the vehicle treated mice (Naïve/veh: 10.15 sec±0.70, 10 mg/kg: 7.94 sec±0.06, 20 mg/kg: 17.50 sec±2.53, p=0.0006) (FIG. 15D). On the other hand, $\Delta^9$-THCB administration did not induce significant changes in the rectal temperature (Naïve/veh: 0.53° C.±0.21, 10 mg/kg: −0.28° C.±0.10, 20 mg/kg: 0.40° C.±0.35, p=0.0379) (FIG. 15E). These results suggest a partial interaction of $\Delta^9$-THCB with CB1 receptor, at least in naïve conditions. On the other hand, the formalin test indicates that the capability of this new cannabinoid in modulating the CB receptors is increased in a pathological state. Further studies are ongoing to elucidate the actual pharmacological mechanism of action of $\Delta^9$-THCB and CBDB.

2.2.8 Concluding Remarks. The butyl homologues of CBD (CBDB) and $\Delta^9$-THC ($\Delta^9$-THCB) were isolated from a medicinal *cannabis* variety. For the first time their absolute configuration was assigned and their chemical and spectroscopic properties were characterized and compared to those of authentic standards obtained via a stereoselective synthesis. The results obtained with the biological tests indicated that the binding affinity of $\Delta^9$-THCB for hCB1 is similar to that of $\Delta^9$-THC and higher than that of $\Delta^9$-THCV. Docking studies suggested that the fitting of $\Delta^9$-THCB into hCB1 receptor pocket is different from that of $\Delta^9$-THC, thus justifying the outcome of the binding experiments. Moreover, $\Delta^9$-THCB showed analgesic effects in the formalin test in mice, although more in-depth investigation may provide additional understanding its potential effects in different types of chronic pain. The results of the tetrad test indicated that $\Delta^9$-THCB should be a partial agonist for $CB_1$ receptor although further studies may be required to completely disclose its pharmacological mechanism in vivo. For the pharmacological research, $\Delta^9$-THCB and CBDB might represent two new phytocannabinoids to focus on in the near future in order to unveil the disconcerting plethora of medicinal properties of *cannabis*.

2.3 EXPERIMENTAL SECTION 2.3.1 General Experimental Procedures. Ethanol 96% (analytical grade), acetonitrile, water and formic acid (LC-MS grade) were purchased from Carlo Erba (Milan, Italy). $\Delta^9$-Tetrahydrocannabivarin ($\Delta^9$-THCV), $\Delta^9$-tetrahydrocannabinol ($\Delta^9$-THC) and cannabidiol (CBD) were purchased as Cerilliant certified analytical standards (Sigma-Aldrich, Milan, Italy). (1S,4R)-1-methyl-4-(prop-1-en-2-yl)cycloex-2-enol and 5-butylbenzene-1,3-diol were purchased from Combi-blocks (San Diego, CA, USA) and GreenPharma (Foligno, Italy), respectively. Chemicals and solvents for the synthesis were reagent grade and used without further purification. Reactions were monitored by thin-layer chromatography on silica gel plates (60F-254, E. Merck) and visualized with UV light, or alkaline $KMnO_4$ aqueous solution. NMR spectra were recorded on a Bruker 400 spectrometer with $^1H$ at 400.134 MHz and $^{13}C$ at 100.62 MHz or with a Bruker 600 spectrometer with $^1H$ at 600.130 MHz and $^{13}C$ at 150.902 MHz. Proton chemical shifts were referenced to the solvent residual peaks ($CDCl_3$ δ=7.26 ppm). Chemical shifts are reported in parts per million (ppm, δ units). Coupling constants are reported in hertz (Hz). Splitting patterns are designed as s, singlet; d, doublet; t, triplet; q quartet; dd, double doublet; m, multiplet; b, broad. $^1H$ NMR were acquired with a spectral width of 8278 Hz, a relaxation delay of 1 s, and 32 number of transient. $^{13}C$ NMR were acquired with a spectral width of 23.9 kHz, a relaxation delay of 1 s, and 1024 and 6144 number of transient for synthetic $\Delta^9$-THCB and extracted $\Delta^9$-THCB, respectively. Carbon chemical shifts were reported in parts per million (ppm, δ units) and referenced to the solvent residual peaks ($CDCl_3$ δ=77.20 ppm). The COSY were recorded as a 2048×256 matrix with 2 transients per t1 increment and processed as a 2048×1024 matrix. The HSQC spectra were collected as a 2048×256 matrix with 4 transients per t1 increment and processed as a 2048×1024 matrix, and the one-bond heteronuclear coupling value was set to 145 Hz. The HMBC spectra were collected as a 4096×256 matrix with 16 transients per t1 increment and processed as a 4096×1024 matrix, and the long-range coupling value was set to 8 Hz.

(6aR,10aR)-3-butyl-6,6,9-trimethyl-6a,7,10,10a-tetrahydro-6H-benzo[c]chromen-1-ol, (−)-trans-$\Delta^8$-tetrahydrocannabidibutol ($\Delta^8$-THCB)

To a solution of 5-butylbenzene-1,3-diol (332 mg, 2.0 mmol, 1 eq.) and p-toluenesulfonic acid (40 mg, 0.2 mmol, 0.1 eq.) in dry dichloromethane ($CH_2Cl_2$) (10 mL) at room temperature, under argon atmosphere, a solution of (1S,4R)-1-methyl-4-(prop-1-en-2-yl)cycloex-2-enol (314 mg, 2.0 mmol, 1 eq.) in 10 mL of dry $CH_2Cl_2$ was added dropwise. The mixture was stirred at room temperature for 2 days and then quenched with a saturated solution of $NaHCO_3$(10 mL). The resulting mixture was extracted in diethyl ether (2×10 mL). The combined organic phases were collected, washed with brine, dried over anhydrous $Na_2SO_4$ and concentrated. The crude was purified over silica gel (crude:silica ratio 1:200, eluent:cyclohexane: $CH_2Cl_2$ 7:3) to give 260 mg of a reddish oil (43% yield). $^1H$ NMR (400 MHz, $CDCl_3$) δ 6.28 (1H, d, J=1.4 Hz), 6.10 (1H, d, J=1.5 Hz), 5.49-5.34 (1H, m), 4.62 (1H, s), 3.19 (1H, dd, J=4.5, 15.8 Hz), 2.70 (1H, td, J=4.7, 10.8 Hz), 2.45 (2H, td, J=2.5, 7.5 Hz), 2.21-2.07 (1H, m), 1.90-1.75 (3H, m), 1.73-1.68 (3H, m), 1.63-1.50 (2H, m), 1.39-1.29 (5H, m), 1.11 (3H, s), 0.91 (3H, t, J=7.3 Hz). HRESIMS m/z 301.2165 [M+H]+(calcd for $C_{20}H_{29}O_2^+$, 301.2162).

(6aR,10aR)-3-butyl-9-chloro-6,6,9-trimethyl-6a,7,8,9,10,10a-hexahydro-6H-benzo[c]chromen-1-ol (HCl-THCB)

To a solution of $\Delta^8$-THCB (260 mg, 0.87 mmol, 1 eq.) in dry $CH_2Cl_2$ (10 mL) at room temperature and under nitrogen atmosphere, $ZnCl_2$ 1N in $Et_2O$ (430 μL, 0.43 mmol, 0.5 eq.) was added. The mixture was stirred in the same condition for 30 minutes and then cooled at 0° C. A large excess of HCl 4N in dioxane (1 mL) was added, the temperature spontaneously raised at room temperature and left reacted for 24 h. The solvent was evaporated and the residue re-solubilized in diethyl ether. The organic layer was washed with a saturated solution of $NaHCO_3$, brine, dried over anhydrous $Na_2SO_4$ and concentrated to give 293 mg of a yellowish oil (quant. yield). $^1H$ NMR (400 MHz, $CDCl_3$) δ 6.25 (1H, s), 6.08 (1H, s), 4.63 (1H, s), 3.71 (3H, s), 3.44 (1H, dt, J=2.8, 14.2 Hz), 3.05 (1H, td, J=2.9, 11.3 Hz), 2.44 (2H, dd, J=6.4, 8.9 Hz), 2.17 (1H, dt, J=2.6, 10.7 Hz), 1.79-1.28 (10H, m), 1.13 (3H, s), 0.90 (3H, t, J=7.3 Hz). $^{13}C$ NMR (101 MHz, $CDCl_3$) δ 13.95, 19.15, 22.36, 24.24, 27.70, 31.37, 33.03, 34.23, 35.08, 42.08, 44.88, 48.76, 67.10, 72.63, 107.67, 108.91, 110.14, 142.83, 154.45, 155.09. HRESIMS m/z 339.1900 $[M+H]^+$ (calcd for $C_{20}H_{30}{}^{37}[Cl]O_2{}^+$, 339.1899), m/z 337.1932 $[M-H]^-$ (calcd for $C_{20}H_{30}{}^{35}[Cl]O_2{}^+$, 337.1929).

(6aR,10aR)-3-butyl-6,6,9-trimethyl-6a,7,8,10a-tetrahydro-6H-benzo[c]chromen-1-ol, (−)-trans-$\Delta^9$-THCB To a solution of 1.75 N potassium t-amylate in toluene (1.23 mL, 2.15 mmol, 2.5 eq.), in dry toluene (10 mL) at −15° C. and under argon atmosphere, a solution of HCl-THCB (290 mg, 0.86 mmol, 1 eq.) in dry toluene (10 mL) was added. The mixture was stirred in the same condition for 30 minutes and then at room temperature for 1 h. The mixture was diluted with diethyl ether and quenched with a 1% solution of ascorbic acid. The organic layer was washed with brine, dried over anhydrous $Na_2SO_4$ and concentrated to give 235 mg of a greenish oil (91% yield). 10 mg of (−)-trans-$\Delta^9$-THCB were further purified by semipreparative HPLC to prepare a pure analytic standard (purity >99.9%). $[\alpha]_D^{20}$ 143° (c 2.3, ACN). $^1$H NMR (400 MHz, $CDCl_3$) δ 6.30 (1H, dt, J=1.7, 3.6 Hz), 6.27 (1H, d, J=1.7 Hz), 6.14 (1H, d, J=1.7 Hz), 4.84 (1H, bs), 3.22 (1H, dt, J=2.8, 10.8 Hz), 2.47 (2H, td, J=1.7, 7.3 Hz), 2.26-2.16 (2H, m), 2.02-1.90 (1H, m), 1.68 (3H, t, J=1.8 Hz), 1.58-1.49 (2H, m), 1.45-1.30 (7H, m), 1.11 (3H, s), 0.92 (3H, t, J=7.3 Hz). $^{13}$C NMR (101 MHz, $CDCl_3$) δ 154.76, 154.17, 142.75, 134.38, 123.72, 110.09, 109.03, 107.54, 77.20, 45.81, 35.17, 33.58, 33.11, 31.17, 27.57, 25.02, 23.36, 22.34, 19.27, 13.95. HRESIMS m/z 301.2157 $[M+H]^+$ (calcd for $C_{20}H_{29}O_2{}^+$, 301.2162), m/z 299.2016 $[M-H]^-$ (calcd for $C_{20}H_{27}O_2{}^-$, 299.2017).

Plant Material. FM2 *cannabis* inflorescence (batch n. 6A 32/1) was obtained by the Military Chemical Pharmaceutical Institute (Firenze, Italy) with the authorization of the Italian Minister of Health (prot. n. SP/062). The inflorescence (5 g) was finely ground and divided into two batches: a 500 mg batch was extracted with 50 mL of ethanol 96% each according to the procedure indicated by the monograph of *Cannabis Flos* of the German Pharmacopoeia[52]. The remainder (4.5 g) was subjected to decarboxylation in oven at 120° C. for 2 h. A 500 mg aliquot of this batch was extracted as the previous one and both were analyzed by UHPLC-HESI-Orbitrap after proper dilution (×10). The remaining 4 g were dissolved into 40 mL of ethanol 96% and used for isolation of $\Delta^9$-THCB by semi-preparative liquid chromatography.

Isolation of Natural CBDB and $\Delta^9$-THCB. A sample of FM2 inflorescence (4 g) was dissolved in ethanol 96% (40 mL) and 0.5 mL aliquots of the solution were injected in a semi-preparative LC system (Octave 10 Semba Bioscience, Madison, USA). The chromatographic conditions used are reported in the paper by Citti et al.[27] The column employed was a Luna C18 with a fully porous silica stationary phase (Luna 5 μm C18(2) 100 Å, 250×10 mm) (Phenomenex, Bologna, Italy) and a mixture of acetronitrile:0.1% aqueous formic acid 70:30 (v/v) was used as mobile phase at a flow rate of 5 mL/min. CBDB and $\Delta^9$-THCB (retention time 18.7 min and 34.0 min respectively) were isolated as reported in our previous work.[27] The fractions containing CBDB and $\Delta^9$-THCB were analyzed by UHPLC-HESI-Orbitrap. The fractions containing exclusively either one or the other cannabinoid were separately combined and dried on the rotavapor at 70° C. An amount of about 1 mg of CBDB and about 1 mg of $\Delta^9$-THCB were obtained, both as reddish oils.

UHPLC-HESI-Orbitrap Metabolomic Analysis. The analyses of FM2 plant material were performed on a Thermo Fisher Scientific Ultimate 3000 equipped with a vacuum degasser, a binary pump, a thermostated autosampler, a thermostated column compartment and a Q-Exactive Orbitrap mass spectrometer with a heated electrospray ionization source (UHPLC-HESI-Orbitrap). The direct infusion of the single analytes (1 μg/mL) at 0.1 mL/min was employed to optimize the parameters of the mass spectrometer. The HESI parameters were set as follows: capillary temperature, 320° C.; vaporizer temperature, 280° C.; electrospray voltage, 4.2 kV (positive mode) and 3.8 kV (negative mode); sheath gas, 55 arbitrary units; auxiliary gas, 30 arbitrary units; S lens RF level, 45. The Xcalibur 3.0 software (Thermo Fisher Scientific, San Jose, CA, USA) was used to control online analyses. The analyses were acquired in full scan data-dependent acquisition (FS-dd-$MS^2$) in positive and negative mode at a resolving power of 70,000 FWHM at m/z 200. The other mass analyzer parameters were: scan range, m/z 250-400; AGC, 3e6; injection time, 100 ms; isolation window for the filtration of the precursor ions, m/z 2. Fragmentation of precursors was performed at 30 as normalized collision energy (NCE) by injecting a standard mixture of the analytes at a concentration of 1 μg/L. Detection was based on calculated $[M+H]^+$ and $[M-H]^-$ molecular ions with an accuracy of 2 ppm, retention time and MS/MS spectrum match with pure analytical standards.

The chromatographic separation was performed on a Poroshell 120 SB-C18 (3.0×100 mm, 2.7 μm, Agilent, Milan, Italy) eluting 0.1% aqueous formic acid (A) and acetonitrile (B) as mobile phase. A linear gradient from 5% to 95% B was set over 20 min, followed by an isocratic elution at 95% B for 5 min, and re-equilibration to the initial conditions (5% B) for further 5 min. The flow rate was maintained constant at 0.5 mL/min and the injection volume was 5 μL.

In order to provide a semi-quantitative analysis of the butyl homologues of CBD and $\Delta^9$-THC, we performed a calibration curve with external standard. A stock solution of CBDB and $\Delta^9$-THCB (1 mg/mL) were properly diluted to obtain 5 calibration standards with the final concentrations of 0.50, 1.50, 3.75, 7.50 and 11.25 μg/mL for both analytes. The linearity was assessed by the coefficient of determination, which was greater than 0.998 for both analytes.

Binding at CB1 and CB2 Receptors. The binding affinity of (−)-trans-$\Delta^9$-THCB against human CB1 and CB2 receptors was determined in a radioligand binding assay performed by Eurofins Discovery. The compound was tested at ten concentrations, ranging from 1 nM to 30 μM, in duplicate. The compound binding was calculated as a % inhibition of the binding of a radioactively labeled ligand specific for each target. [$^3$H]CP55940 (at 2 nM, $K_d$=2.4 nM)[53] and [$^3$H]WIN 55212-2 (at 0.8 nM, $K_d$=1.5 nM)[54] were used as specific radioligand for hCB1 and hCB2, respectively. The results were expressed as a percent inhibition of control specific binding obtained in the presence of the tested compounds using eq. 1.

$$\%\ in = 100 - \left(\frac{\text{measured specific binding}}{\text{control specific binding}} * 100\right) \quad \text{eq. 1}$$

The $IC_{50}$ values (concentration causing a half-maximal inhibition of control specific binding) were determined by non-linear regression analysis of the competition curves generated with mean replicate values (eq. 2)[55].

$$Y = D + \left[\frac{A - D}{1 + \left(\frac{C}{C_{50}}\right)^{nH}}\right] \quad \text{eq. 2}$$

Where Y is the specific binding, A is the left asymptote of the curve, D is the right asymptote f the curve, C is the compound concentration, $C_{50}$ is the $IC_{50}$ value and nH is the slope factor. This analysis was performed using software developed at Cerep (Hill software) and validated by comparison with data generated by the commercial software SigmaPlot® 4.0 for Windows® (© 1997 by SPSS Inc.). The inhibition constants ($K_i$) were calculated using the Cheng Prusoff equation:

$$Ki = \frac{IC_{50}}{\left(1 + \frac{L}{K_D}\right)} \quad \text{eq. 3}$$

where L is the concentration of radioligand in the assay, and $K_D$ is the affinity of the radioligand for the receptor. CP 55940 (CB1 $IC_{50}$=1.7 nM, CB1 $K_i$=0.93 nM) and WIN 55212-2 (CB2 $IC_{50}$=2.7 nM, CB2 $K_i$=1.7 nM) were used as reference compounds against hCB1 and hCB2, respectively and the results are in accordance with the values reported in literature.[53,54]

Docking calculation. The crystal structure for the active conformation of CB1 (PDB ID: 5XRA) was used as reference protein for docking calculation. The protein was prepared using the protein preparation wizard module of the Schrodinger suite[56]. The protonation and tautomeric states of the residues were adjusted at pH 7.0[57, 58]. Water molecules were removed, and the hydrogens position was minimized with the OPLS_2005 force field. The chemical structures of $\Delta^9$-tetrahydrocannabinol ($\Delta^9$-THC), $\Delta^9$-tetrahydrocannabivarin ($\Delta^9$-THCV), and $\Delta^9$-tetrahydrocannabidibutol ($\Delta^9$-THCB), were drawn using ChemDraw 12.0 and prepared using the LigPrep module of Schrödinger suite with the OPLS_2005 force field[59]. The three ligands were docked into the orthosteric binding site of the active conformation of the CB1 structure by using the Glide module of Schrödinger suite[60].

Formalin test in mice. Male CD-1 mice 6-8 weeks (Envigo, Italy), were housed under controlled conditions (12 h light/12 h dark cycle; temperature 20-22 C; humidity 55-60%) with chow and tap water available ad libitum. All surgeries and experimental procedures were approved by the Animal Ethics Committee of University of Campania "L. Vanvitelli" (Naples). Animal care was in compliance with Italian (D.L. 116/92) and European Commission (O.J. of E.C. L358/1 18/12/86) regulations on the protection of laboratory animals. All efforts were made to minimize animal suffering and to reduce the number of animals used. All the experiments were performed in a randomized manner by the same operator blind to pharmacological treatments. Mice weighing 28-32 g were used after 1 week-acclimation period and received formalin (1.25% in saline, 30 µL) in the dorsal surface of one side of the hind-paw. Each mouse, randomly assigned to one of the experimental groups (n=5), was placed in a plexiglass cage and allowed to move freely for 15-20 min. A mirror was placed at a 45° angle under the cage to allow full view of the hind-paws. Lifting, favoring, licking, shaking and flinching of the injected paw were recorded as nocifensive behavior.[61] The total time of the nociceptive response was measured every 5 min for 60 minutes and expressed in min (mean±SEM). Mice received vehicle (0.5% DMSO in saline) or different doses of $\Delta^9$-THCB (2, 3 and 5 mg/kg, i.p.) 20 min before formalin injection alone or in combination with AM251 (0.5 mg/kg, i.p.) or AM630 (1 mg/kg, i.p.). The antagonists were administered 10 min before drugs injection.

Tetrad test. Male C57BL6/J mice 6-8 weeks (Envigo, Italy) were housed under controlled conditions (12 h light/12 h dark cycle; temperature 20-22 C; humidity 55-60%) with chow and tap water available ad libitum. All surgeries and experimental procedures were approved by the Animal Ethics Committee of University of Campania "L. Vanvitelli," Naples. Animal care was in compliance with Italian (D.L. 116/92) and European Commission (O.J. of E.C. L358/1 8/12/86) regulations on the protection of laboratory animals. All efforts were made to minimize animal suffering and to reduce the number of animals used. All the experiments were performed in a randomized manner by the same operator blind to pharmacological treatments.

Mice (n=4) were treated with $\Delta^9$-THCB (10 and 20 mg/kg) or vehicle (0.9% saline and 0.05% DMSO) by intraperitoneal (i.p.) administration. Mice were evaluated for hypomotility (open field test), hypothermia (body temperature test), antinociceptive (hot plate test), and cataleptic effects (bar test), using the tetrad tests as described in the protocol by Metna-Laurent M. et al.[62] Statistical analysis was performed using the Kruskall-Wallis test and Dunn's post hoc tests.

Body temperature test. A probe was gently inserted for 1 cm into the mouse rectum after the animal had been immobilized. The probe was washed and cleaned with 70% ethanol and the dried with a paper towel. The body temperature was measured after stabilization of the value in ° C. in basal conditions and at 50 minutes after drug or vehicle administration.

Open field test. The open field test (OFT) was performed 30 min after drug or vehicle injection. The apparatus was cleaned before each test using a 70% EtOH solution. After randomly assigning naïve mice to a treatment group, the operator started to record animal behaviors, which were stored and analyzed using an automated behavioral tracking system (Smart v3.0, Panlab Harvard Apparatus). Mice were placed in an OFT arena (l×w×h: 44 cm×44 cm×30 cm), and ambulatory activity (total distance travelled in cm), was recorded for 15 min and analyzed.

Bar test. The bar used was a 40 cm long and 0.4 cm wide in diameter glass rod, which was horizontally elevated by 5 cm above the surface. Both forelimbs of the mouse were positioned on the bar and its hind legs on the floor of the cage, ensuring that the animal was not lying down on the floor. The chronometer was stopped when the mouse descended from the bar (i.e., when the two forepaws touched the floor) or after the 10 min cut-off time. Catalepsy was measured as the time duration each mouse held the bar by both his forelimbs (latency for moving in seconds).

Hotplate test. Each mouse was placed on a hot plate (Ugo Basile), which was kept at a constant temperature of 52° C. The nociceptive response (NR) was recorded as characteristic actions of the mouse like licking of the hind paws, as well as jumping. The latency to the NR was measured in sec 85 minutes after drug or vehicle administration. A 30 or 60 sec cut-off time was used in order to prevent tissue damage.

Statistics for in vivo experiments. Data are represented as means±standard error of the mean (S.E.M). Statistical analysis of the data was performed by analysis of variance two-way ANOVA followed by Bonferroni post hoc or Dunnett's multiple comparison test. All statistical analyses were performed by using GraphPAD software (San Diego, California). Differences were considered significant at $p<0.05$.

2.4 ASSOCIATED CONTENT

Figure 16A:
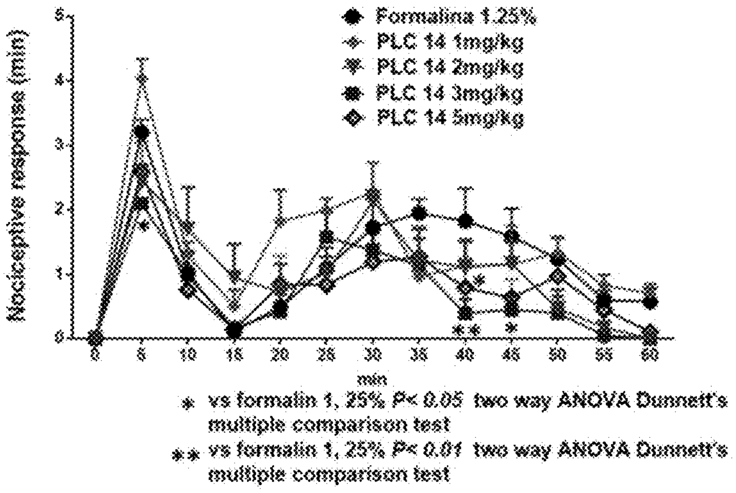
FIG. 16 shows effect of THCB (PLC14) or CBDB (PLC4), at different doses, on the two phases of formalin test, according to an exemplary embodiment of the present disclosure.
Figure 16B:
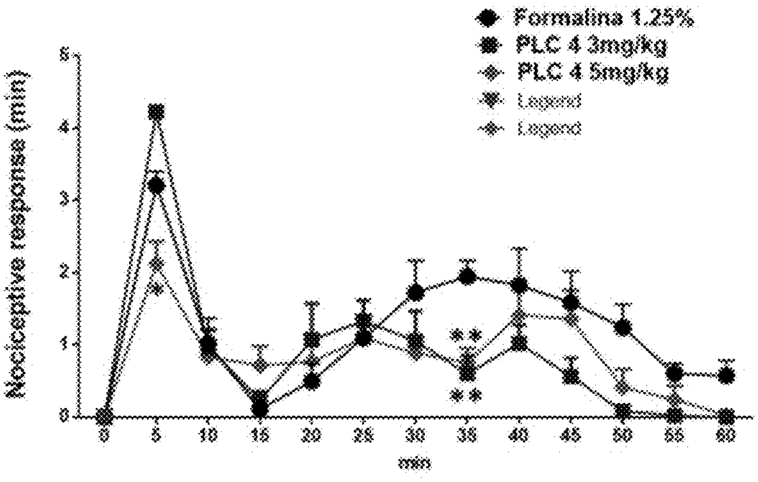

Exhibit B—Supporting Information and FIG. 16. Spectroscopic data of synthetic and extracted $\Delta^9$-THCB: original NMR and circular dichroism (CD) spectra for the new compound.

2.5 REFERENCES (1) Pisanti, S.; Bifulco, M. *J. Cell. Physiol.* 2019, 234, 8342-8351.

(2) Frassinetti, S.; Moccia, E.; Caltavuturo, L.; Gabriele, M.; Longo, V.; Bellani, L.; Giorgi, G.; Giorgetti, L. *Food Chem.* 2018, 262, 56-66.

(3) McCabe, C. S.; Blake, D. R.; Ho, M.; Robson, P.; Jubb, R. W. *Rheumatology.* 2005, 45, 50-52.

(4) Koppel, B. S.; Brust, J. C. M.; Fife, T.; Bronstein, J.; Youssof, S.; Gronseth, G.; Gloss, D. *Report of the Guideline Development Subcommittee of the American Academy of Neurology.* 2014, 82, 1556-1563.

(5) Borgelt, L. M.; Franson, K. L.; Nussbaum, A. M.; Wang, G. S. *Pharmacotherapy.* 2013, 33, 195-209.

(6) Whiting, P. F.; Wolff, R. F.; Deshpande, S.; Di Nisio, M.; Duffy, S.; Hernandez, A. V.; Keurentjes, J. C.; Lang, S.; Misso, K.; Ryder, S.; Schmidlkofer, S.; Westwood, M.; Kleijnen, J. *JAMA.* 2015, 313, 2456-2473.

(7) Moreno, J. L. L.-S.; Caldentey, J. G.; Cubillo, P. T.; Romero, C. R.; Ribas, G. G.; Arias, M. A. A.; De Yébenes, M. J. G.; Tolón, R. M.; Galve-Roperh, I.; Sagredo, O. J. *Neurol.* 2016, 263, 1390-1400.

(8) Keating, G. M. *Drugs.* 2017, 77, 563-574.

(9) Citti, C.; Braghiroli, D.; Vandelli, M. A.; Cannazza, G. *J. Pharm. Biomed. Anal.* 2018, 147, 565-579.

(10) Happyana, N.; Agnolet, S.; Muntendam, R.; Van Dam, A.; Schneider, B.; Kayser, O. *Phytochemistry.* 2013, 87, 51-59.

(11) Giese, M. W.; Lewis, M. A.; Giese, L.; Smith, K. M. *J. AOAC Int.* 2015, 98, 1503-1522.

(12) Radwan, M. M.; Wanas, A. S.; Chandra, S.; ElSohly, M. A. In *Cannabis sativa L.-Botany and Biotechnology; Natural Cannabinoids of Cannabis and Methods of Analysis*; Chandra, S.; Lata, H.; ElSohly, M. A., Eds. Springer International Publishing: Cham, 2017; pp 161-182.

(13) Mudge, E. M.; Murch, S. J.; Brown, P. N. *Anal. Bioanal. Chem.* 2017, 409, 3153-3163.

(14) Citti, C.; Ciccarella, G.; Braghiroli, D.; Parenti, C.; Vandelli, M. A.; Cannazza, G. *J. Pharm. Biomed. Anal.* 2016, 128, 201-209.

(15) Elkins, A. C.; Deseo, M. A.; Rochfort, S.; Ezernieks, V.; Spangenberg, G. *J. Chromatogr.* B. 2019, 1109, 76-83.

(16) Leghissa, A.; Smuts, J.; Qiu, C.; Hildenbrand, Z. L.; Schug, K. A. *SEPARATION SCIENCE PLUS.* 2018, 1, 37-42.

(17) Hall, R. D. In *Annual Plant Reviews online; Plant Metabolomics in a Nutshell: Potential and Future Challenges*; Roberts, J. A., Ed. 2018.

(18) Panda, A.; Parida, A. K.; Rangani, J. *In Plant Metabolites and Regulation Under Environmental Stress; Chapter 1 —Advancement of Metabolomics Techniques and Their Applications in Plant Science: Current Scenario and Future Prospective*; Ahmad, P.; Ahanger, M. A.; Singh, V. P.; Tripathi, D. K.; Alam, P.; Alyemeni, M. N., Eds. Academic Press: 2018; pp 1-36.

(19) Arno, H.; Katerina, T.; Stelios, P. *Cannabis and Cannabinoid Research.* 2016, 1, 202-215.

(20) Choi, Y. H.; Kim, H. K.; Hazekamp, A.; Erkelens, C.; Lefeber, A. W. M.; Verpoorte, R. *J. Nat. Prod.* 2004, 67, 953-957.

(21) Happyana, N.; Kayser, O. *Planta Med.* 2016, 82, 1217-1223.

(22) Citti, C.; Battisti, U. M.; Braghiroli, D.; Ciccarella, G.; Schmid, M.; Vandelli, M. A.; Cannazza, *G. Phytochem. Anal.* 2018, 29, 144-155.

(23) Citti, C.; Linciano, P.; Panseri, S.; Vezzalini, F.; Forni, F.; Vandelli, M. A.; Cannazza, G. *Front. Plant Sci.* 2019, 10.

(24) Citti, C.; Palazzoli, F.; Licata, M.; Vilella, A.; Leo, G.; Zoli, M.; Vandelli, M. A.; Forni, F.; Pacchetti, B.; Cannazza, G. *J. Pharm. Biomed. Anal.* 2018, 161, 1-11.

(25) Citti, C.; Pacchetti, B.; Vandelli, M. A.; Forni, F.; Cannazza, G. *J. Pharm. Biomed. Anal.* 2018, 149, 532-540.

(26) Palazzoli, F.; Citti, C.; Licata, M.; Vilella, A.; Manca, L.; Zoli, M.; Vandelli, M. A.; Forni, F.; Cannazza, G. *J. Pharm. Biomed. Anal.* 2018, 150, 25-32.

(27) Citti, C.; Linciano, P.; Forni, F.; Vandelli, M. A.; Gigli, G.; Laganá, A.; Cannazza, G. J. *Pharm. Biomed. Anal.* 2019, 175, 112752.

(28) Citti, C.; Linciano, P.; Forni, F.; Vandelli, M. A.; Gigli, G.; Lagana, A.; Cannazza, G. *Data in Brief.* 2019, 26, 104463.

(29) Berman, P.; Futoran, K.; Lewitus, G. M.; Mukha, D.; Benami, M.; Shlomi, T.; Meiri, D. *Sci. Rep.* 2018, 8, 14280.

(30) Calvi, L.; Pentimalli, D.; Panseri, S.; Giupponi, L.; Gelmini, F.; Beretta, G.; Vitali, D.; Bruno, M.; Zilio, E.; Pavlovic, R.; Giorgi, A. *J. Pharm. Biomed. Anal.* 2018, 150, 208-219.

(31) Kimura, M.; Okamoto, K. *Experientia.* 1970, 26, 819-20.

(32) Harvey, D. J. *J. Pharm. Pharmacol.* 1976, 28, 280-5.

(33) Martin Smith, R. *J. Forensic Sci.* 1997, 42, 610-618.

(34) Kirkland, J. J.; Schuster, S. A.; Johnson, W. L.; Boyes, B. E. *J. Pharm. Anal.* 2013, 3, 303-312.

(35) Citti, C.; Battisti, U. M.; Ciccarella, G.; Maiorano, V.; Gigli, G.; Abbate, S.; Mazzeo, G.; Castiglioni, E.; Longhi, G.; Cannazza, G. *J. Chromatogr. A.* 2016, 1467, 335-346.

(36) Gutman, A. L.; Nisnevich, G. A.; Rukhman, I.; Tishin, B.; Etinger, M.; Fedotev, I.; Pertsikov, B.; Khanolkar, R. US patent US20160199344A1, 2013.

(37) Koch, O. G., M. R.; Looft, J.; Voessing, T. European Patent 2842933A1, 2015.

(38) Kupper, R. J. International Patent Appl. WO 2006133941A2, 2006.

(39) Nikas, S.; Thakur, G.; Makriyannis, A. *J. Label. Compd. Radiopharm.* 2002, 45, 1065-1076.

(40) Banijamali, A. R.; Abou-Taleb, N.; Van Der Schyf, C. J.; Charalambous, A.; Makriyannis, A. *J. Label. Compd. Radiopharm.* 1988, 25, 73-82.

(41) Choi, Y. H.; Hazekamp, A.; Peltenburg-Looman, A. M.; Frederich, M.; Erkelens, C.; Lefeber, A. W.; Verpoorte, R. *Phytochem. Anal.* 2004, 15, 345-54.

(42) Mechoulam, R.; Braun, P.; Gaoni, Y. *J. Am. Chem. Soc.* 1972, 94, 6159-6165.

(43) Bow, E. W.; Rimoldi, J. M. *Perspect. Medicin. Chem.* 2016, 8, 17-39.

(44) Jung, S. W.; Cho, A. E.; Yu, W. *Sci. Rep.* 2018, 8, 13787-13787.

(45) Hua, T.; Vemurii, K.; Nikas, S. P.; Laprairie, R. B.; Wu, Y.; Qu, L.; Pu, M.; Korde, A.; Jiang, S.; Ho, J. H.; Han, G. W.; Ding, K.; Li, X.; Liu, H.; Hanson, M. A.; Zhao, S.; Bohn, L. M.; Makriyannis, A.; Stevens, R. C.; Liu, Z. *J. Nature.* 2017, 547, 468-471.

(46) Li, X.; Hua, T.; Vemuri, K.; Ho, J.-H.; Wu, Y.; Wu, L.; Popov, P.; Benchama, O.; Zvonok, N.; Locke, K. a.; Qu, L.; Han, G. W.; Iyer, M. R.; Cinar, R.; Coffey, N. J.; Wang, J.; Wu, M.; Katritch, V.; Zhao, S.; Kunos, G.; Bohn, L. M.; Makriyannis, A.; Stevens, R. C.; Liu, Z.-J. *Cell.* 2019, 176, 459-467.e13.

(47) Nikas, S. P.; Grzybowska, J.; Papahatjis, D. P.; Charalambous, A.; Banijamali, A. R.; Chari, R.; Fan, P.; Kourouli, T.; Lin, S.; Nitowski, A. J.; Marciniak, G.; Guo, Y.; Li, X.; Wang, C.-L. J.; Makriyannis, A. *AAPS J.* 2004, 6, e30-e30.

(48) Nikas, S. P.; Alapafuja, S. O.; Papanastasiou, I.; Paronis, C. A.; Shukla, V. G.; Papahatjis, D. P.; Bowman, A. L.; Halikhedkar, A.; Han, X.; Makriyannis, A. *J. Med. Chem.* 2010, 53, 6996-7010.

(49) Xie, X. Q.; Melvin, L. S.; Makriyannis, A. *J. Biol. Chem.* 1996, 271, 10640-7.

(50) Makriyannis, A.; Rapaka, R. S. *NIDA Res. Monogr.* 1987, 79, 204-10.

(51) Rodrigues, T.; Sieglitz, F.; Bernardes, G. J. L. *Chem. Soc. Rev.* 2016, 45, 6130-6137.

(52) Bundesinstitut für Arzneimittel und Medizinprodukte. *Cannabis* Flos. In *New text of the German Pharmacopoeia*, Germany, 2018.

(53) Rinaldi-Carmona, M.; Calandra, B.; Shire, D.; Bouaboula, M.; Oustric, D.; Barth, F.; Casellas, P.; Ferrara, P.; Le Fur, G. *J. Pharmacol. Exp. Ther.* 1996, 278, 871-878.

(54) Munro, S.; Thomas, K. L.; Abu-Shaar, M. *Nature.* 1993, 365, 61-5.

(55) Ponzoni, L.; Braida, D.; Pucci, L.; Andrea, D.; Fasoli, F.; Manfredi, I.; Papke, R. L.; Stokes, C.; Cannazza, G.; Clementi, F.; Gotti, C.; Sala, M. *Psychopharmacology (Berl.).* 2014, 231, 4681-4693.

(56) *Schrodinger Release* 2014-3*: Maestro, Schrodinger LLC*, New York, NY (USA), 2014.

(57) Battisti, U. M.; Jozwiak, K.; Cannazza, G.; Puia, G.; Stocca, G.; Braghiroli, D.; Parenti, C.; Brasili, L.; Carrozzo, M. M.; Citti, C.; Troisi, L. *ACS Med. Chem. Lett.* 2012, 3, 25-29.

(58) Citti, C.; Battisti, U. M.; Cannazza, G.; Jozwiak, K.; Stasiak, N.; Puja, G.; Ravazzini, F.; Ciccarella, G.; Braghiroli, D.; Parenti, C.; Troisi, L.; Zoli, M. *ACS Chem. Neurosci.* 2016, 7, 149-160.

(59) *Schrodinger Release* 2014-3*: LigPrep, Schrodinger LLC*, New York, NY (USA), 2014.

(60) *Schrodinger Release* 2014-3*: Glide* (*Version*6.8), *Schrodinger LLC*, New York, NY (USA), 2014.

(61) Abbott, F. V.; Guy, E. R. *Pain.* 1995, 62, 303-312.

(62) Metna-Laurent, M.; Mondésir, M.; Grel, A.; Vallée, M.; Piazza, P.-V. *Curr. Protoc. Neurosci.* 2017, 80, 9.59.1-9.59.10.

Example 3 a Novel Phytocannabinoid Isolated from *Cannabis sativa* L. With an In Vivo Cannabimimetic Activity Higher than $\Delta^9$-Tetrahydrocannabinol: $\Delta^9$-Tetrahydrocannabiphorol Abstract (−)-Trans-$\Delta^9$-tetrahydrocannabinol ($\Delta^9$-THC) is the main compound responsible for the intoxicant activity of *Cannabis sativa* L. The length of the side alkyl chain influences the biological activity of this cannabinoid. In particular, synthetic analogues of $\Delta^9$-THC with a longer side chain have shown cannabimimetic properties far higher than $\Delta^9$-THC itself. In the attempt to define the phytocannabinoids profile that characterizes a medicinal *cannabis* variety, a new phytocannabinoid with the same structure of $\Delta^9$-THC but with a seven-term alkyl side chain was identified. The natural compound was isolated and fully characterized and its stereochemical configuration was assigned by match with the same compound obtained by a stereoselective synthesis. This new phytocannabinoid has been called (−)-trans-$\Delta^9$-tetrahydrocannaphorol ($\Delta^9$-THCP). Along with $\Delta^9$-THCP, the corresponding cannabidiol (CBD) analog with seven-term side alkyl chain was also isolated and identified by match with its synthetic counterpart. The binding activity of $\Delta^9$-THCP against human $CB_1$ receptor in vitro ($K_i$=1.2 nM) resulted similar to that of CP55940 ($K_i$=0.9 nM), a potent full $CB_1$ agonist. In the cannabinoid tetrad pharmacological test, $\Delta^9$-THCP induced hypomotility, analgesia, catalepsy and decreased rectal temperature indicating a THC-like cannabimimetic activity. The presence of this new phytocannabinoid could account for the high efficacy of some extremely potent *cannabis* varieties.

INTRODUCTION

*Cannabis sativa* has always been a controversial plant due to its positive and negative implications, a lifesaver for several pathologies including glaucoma[1] and epilepsy[2], an invaluable source of nutrients[3], an environmentally friendly raw material for manufacturing[4] and textiles[5], but it is also the most widely spread illicit drug in the world, especially among young adults[6].

Its fundamental peculiarity is its ability to produce a class of organic molecules called phytocannabinoids, which derive from an enzymatic reaction between a resorcinol and an isoprenoid group. The modularity of these two parts is the key for the extreme variability of the resulting product that has led to almost 150 different known phytocannabinoids[7]. The precursors for the most commonly naturally occurring phytocannabinoids are olivetolic acid and geranyl pyrophosphate, which take part to a condensation reaction leading to the formation of cannabigerolic acid (CBGA). CBGA can be then converted into either tetrahydrocannabinolic acid (THCA) or cannabinolic acid (CBDA) or cannabichromenic acid (CBCA) by the action of a specific cyclase enzyme[7]. All phytocannabinoids are biosynthesized in the carboxylated form, which can be converted into the corresponding decarboxylated (or neutral) form by heat[8]. The best known neutral cannabinoids are undoubtedly $\Delta^9$-tetrahydrocannabinol ($\Delta^9$-THC) and cannabidiol (CBD), the former being responsible for the intoxicant properties of *cannabis* plant, and the latter being active as antioxidant, anti-inflammatory, anti-convulsant, but also as antagonist of THC negative effects[9].

All these cannabinoids are characterized by the presence of an alkyl side chain on the resorcinyl moiety made of five carbon atoms. However, other phytocannabinoids with a different number of carbon atoms on the side chain are known and they have been called varinoids (with three carbon atoms), such as cannabidivarin (CBDV) and $\Delta^9$-tetrahydrocannabivarin ($\Delta^9$-THCV), and orcinoids (with one carbon atom), such as cannabidiorcol (CBD-$C_1$) and tetrahydrocannabiorcol (THC-$C_1$)[7]. Both series are biosynthesized in the plant as the specific ketide synthases have been identified[10].

Our research group has recently reported the presence of a butyl phytocannabinoid series with a four-term alkyl chain, in particular cannabidibutol (CBDB) and $\Delta^9$-tetrahydrocannabutol ($\Delta^9$-THCB), in CBD samples derived from hemp and in a medicinal *cannabis* variety[11,12]. Since no evidence has been provided for the presence of plant enzymes responsible for the biosynthesis of these butyl phytocannabinoids, it has been suggested that they might derive from microbial ω-oxidation and decarboxylation of their corresponding five-term homologues[13].

The length of the alkyl side chain has indeed proved to be the key parameter, the pharmacophore, for the biological activity exerted by $\Delta^9$-THC on the human cannabinoid receptor $CB_1$ as evidenced by structure-activity relationship studies collected by Bow and Rimondi[14]. In particular, a minimum of three carbons is necessary to bind the receptor, then the highest activity has been registered with an eight-carbon side chain to finally decrease with a higher number of carbon atoms[14]. $\Delta^8$-THC homologues with more than five carbon atoms on the side chain have been synthetically produced and tested in order to have molecules several times more potent than $\Delta^9$-THC[15].

To the best of our knowledge, a phytocannabinoid with a linear alkyl side chain containing more than five carbon atoms has never been reported as naturally occurring. However, our research group disclosed for the first time the presence of seven-term homologues of CBD and $\Delta^9$-THC in a medicinal *cannabis* variety, the Italian FM2, provided by the Military Chemical Pharmaceutical Institute in Florence. The two new phytocannabinoids were isolated and fully characterized and their absolute configuration was determined by a stereoselective synthesis. According to the International Non-proprietary Name (INN), we suggested for these CBD and THC analogues the name "cannabidiphorol" (CBDP) and "tetrahydrocannabiphorol" (THCP), respectively. The suffix "-phorol" comes from "sphaerophorol", common name for 5-heptyl-benzen-1,3-diol, which constitutes the resorcinyl moiety of these two new phytocannabinoids. In particular, the seven-term $\Delta^9$-THC homologue showed surprisingly higher binding affinity to $CB_1$ in vitro and higher cannabimimetic activity in vivo in the tetrad test compared to $\Delta^9$-THC.

Figure 17A:
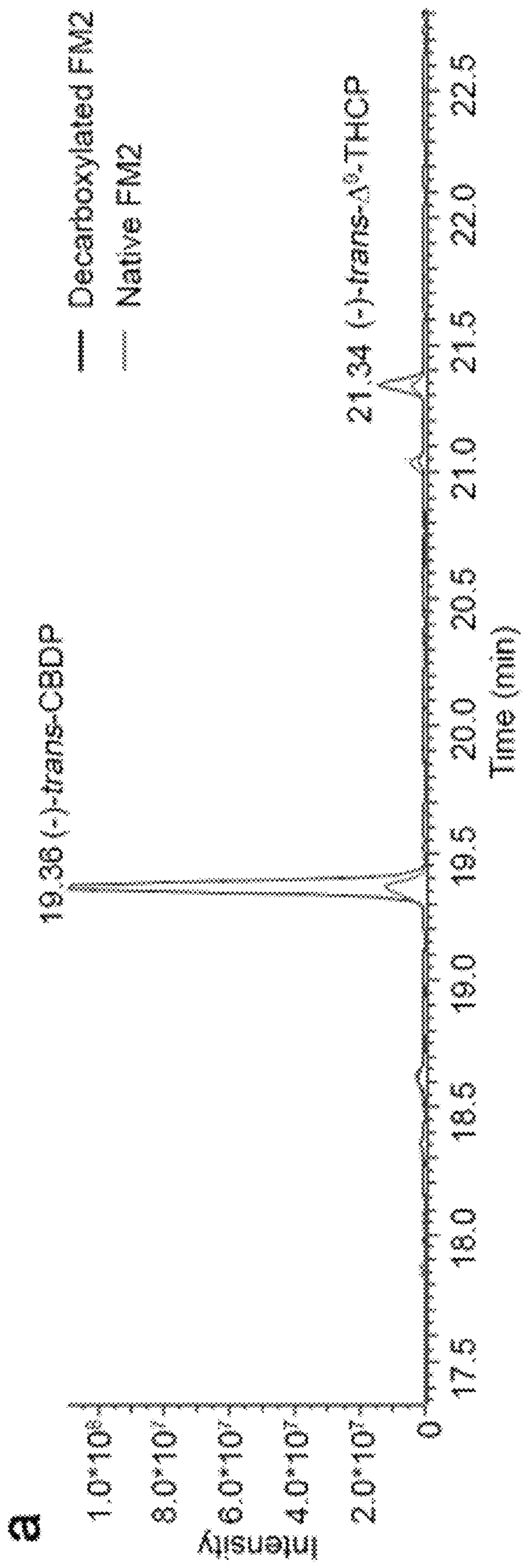
FIGS. 17(A), 17(B), 17(C) and 17(D), collectively, show UHPLC-HRMS identification of (−)-trans-CBDP and (−)-trans-$\Delta^9$-THCP, according to an exemplary embodiment of the present disclosure.
Figure 17B:
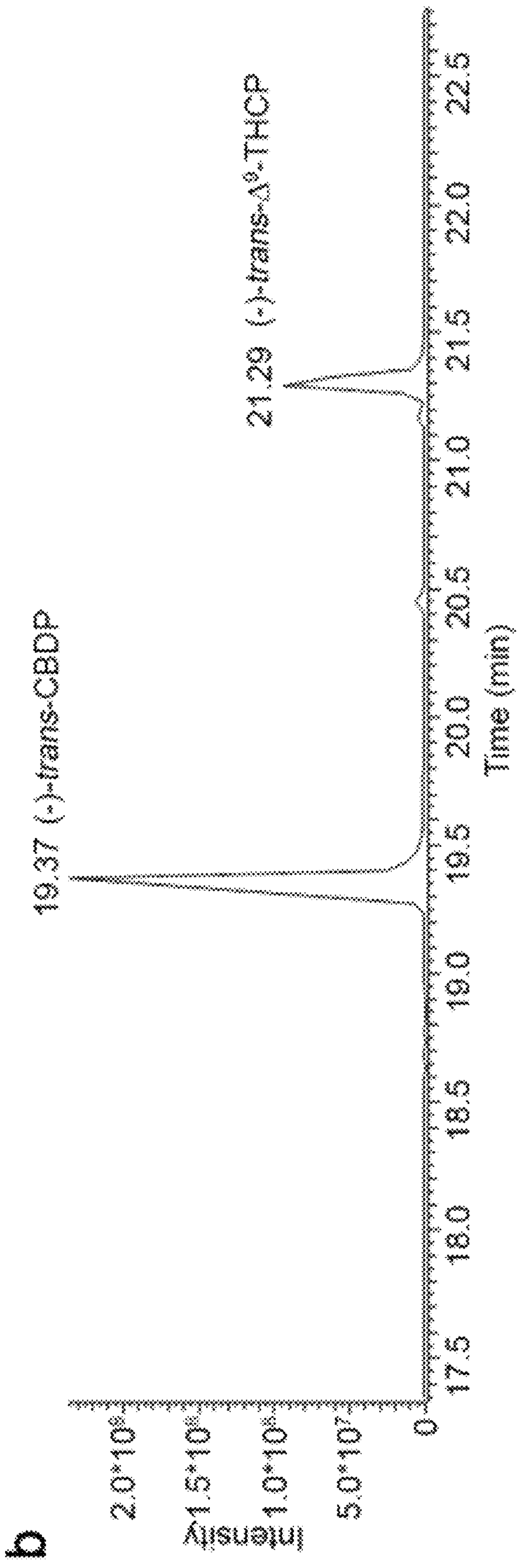
Figure 17C:
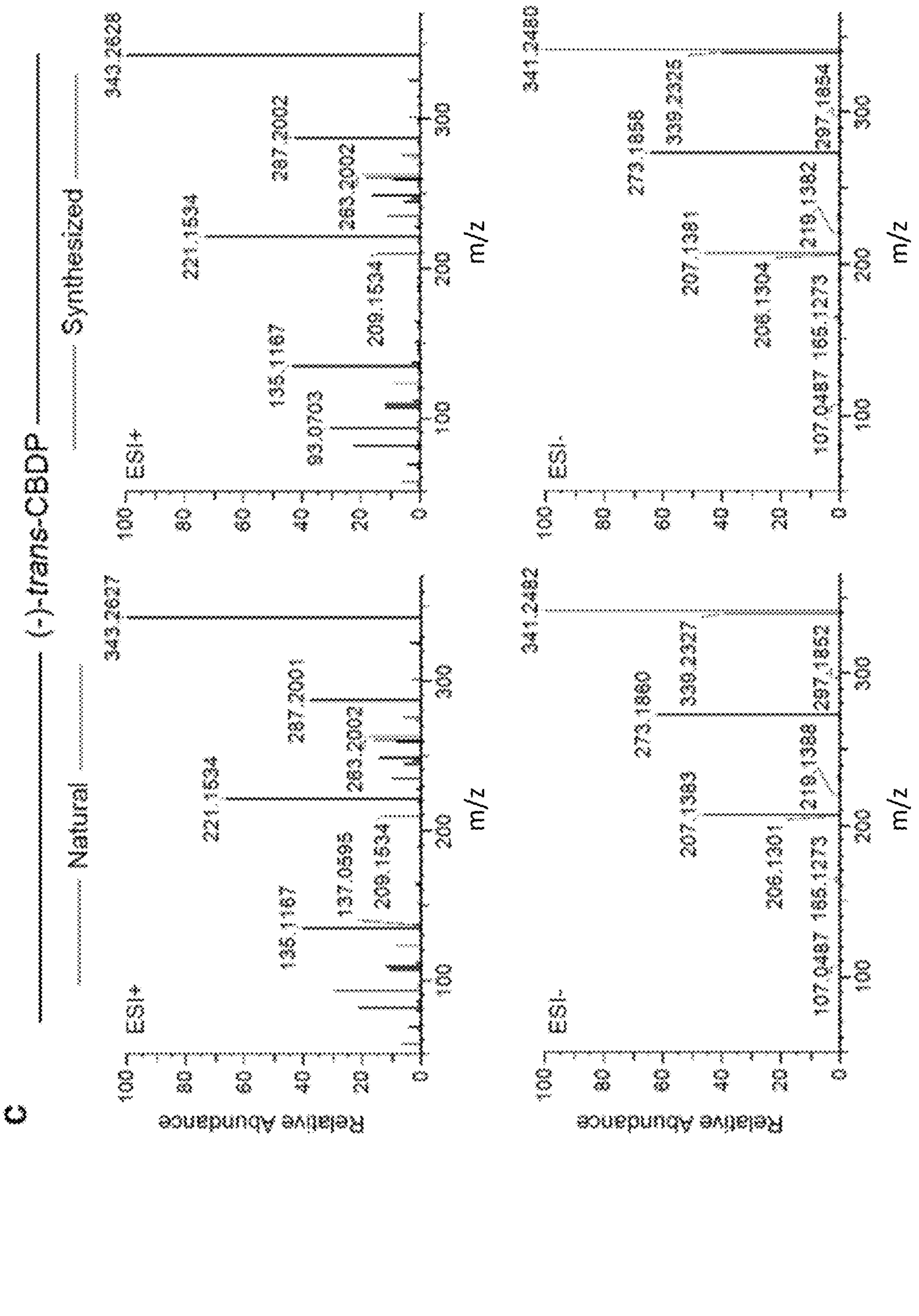
Figure 17D:
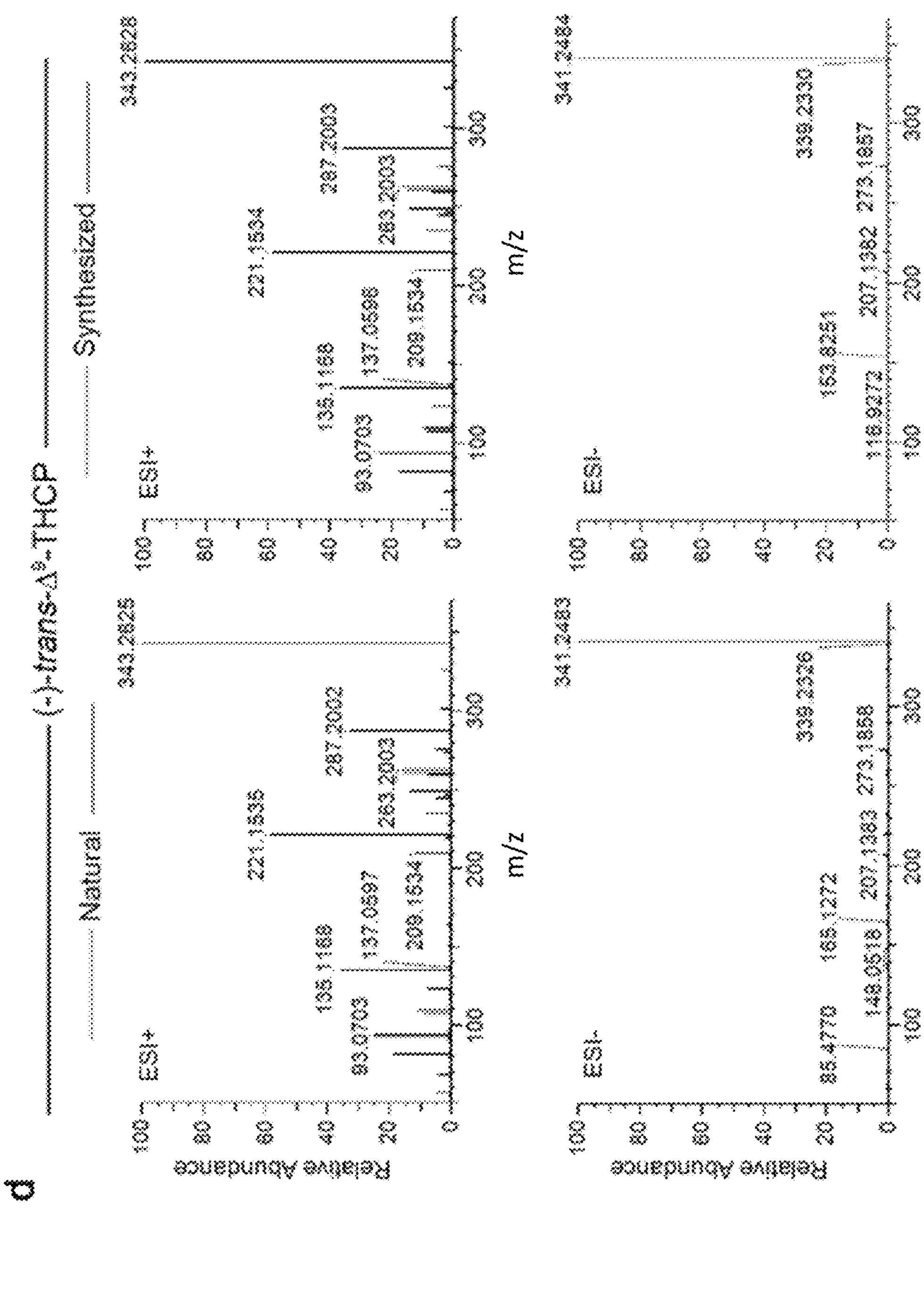

3.1 RESULTS 3.1.1 Identification of cannabidiphorol (CBDP) and $\Delta^9$-tetrahydrocannabiphorol (THCP) by liquid chromatography coupled to high-resolution mass spectrometry (LC-HRMS). The FM2 ethanolic extract was analyzed by an analytical method recently developed for the cannabinoid profiling of this medicinal *cannabis* variety[12,16]. As the native extract contains mainly the carboxylated forms of phytocannabinoids as a consequence of a cold extraction[17], part of the plant material was heated to achieve decarboxylation where the predominant forms are neutral phytocannabinoids. The advanced analytical platform of ultra-high performance liquid chromatography coupled to high resolution Orbitrap mass spectrometry was employed to analyze the FM2 extracts and study the fragmentation spectra of the analytes under investigation. The precursor ions of the neutral derivatives cannabidiphorol (CBDP) and $\Delta^9$-tetrahydrocannabiphorol ($\Delta^9$-THCP), 341.2486 for the $[M-H]^-$ and 343.2632 for the $[M+H]^+$, showed an elution time of 19.4 for CBDP and 21.3 for $\Delta^9$-THCP (FIG. 17*a*). Their identification was determined by the injection of a mixture (5 ng/mL) of the two chemically synthesized CBDP and $\Delta^9$-THCP (FIG. 17*b*) as it will be described later. As for their carboxylated counterpart, the precursor ions of the neutral forms CBDP and $\Delta^9$-THCP break in the same way in ESI+ mode, but they show a different fragmentation pattern in ESI−mode. Whilst $\Delta^9$-THCP shows only the precursor ion $[M-H]^-$ (FIG. 17*d*), CBDP molecule generates the fragments at m/z 273.1858 corresponding to a retro Diels-Alder reaction, and 207.1381 corresponding to the resorcinyl moiety after the break of the bond with the terpenoid group (FIG. 17*c*). It is noteworthy that for both molecules, CBDP and $\Delta^9$-THCP, each fragment in both ionization modes differ exactly by an ethylene unit $(CH_2)_2$ from the corresponding five-termed homologues CBD and THC. Moreover, the longer elution time corroborate the hypothesis of the seven-termed phytocannabinoids considering the higher lipophilicity of the latter.

3.1.2 Isolation and characterization of CBDP and $\Delta^9$-THCP. In order to selectively obtain a cannabinoid-rich fraction of FM2, n-hexane was used to extract the raw material instead of ethanol, which carries other contaminants such as flavonoids and chlorophylls along with cannabinoids[18]. An additional dewaxing step at −20° C. for 48 h and removal of the precipitated wax resulted in a pure cannabinoids extract. Semi-preparative liquid chromatography with a $C_{18}$ stationary phase allowed for the separation of 80 fractions, which were analyzed by LC-HRMS with the previously described method. In this way, the fractions containing predominantly CBDPA and THCPA were separately subject to heating at 120° C. for 2 h in order to obtain their corresponding neutral counterparts CBDP and $\Delta^9$-THCP as clear oils with a >95% purity. The material obtained was sufficient for a full characterization by $^1H$ and $^{13}C$ NMR, circular dichroism (CD) and UV absorption.

Figure 18A:
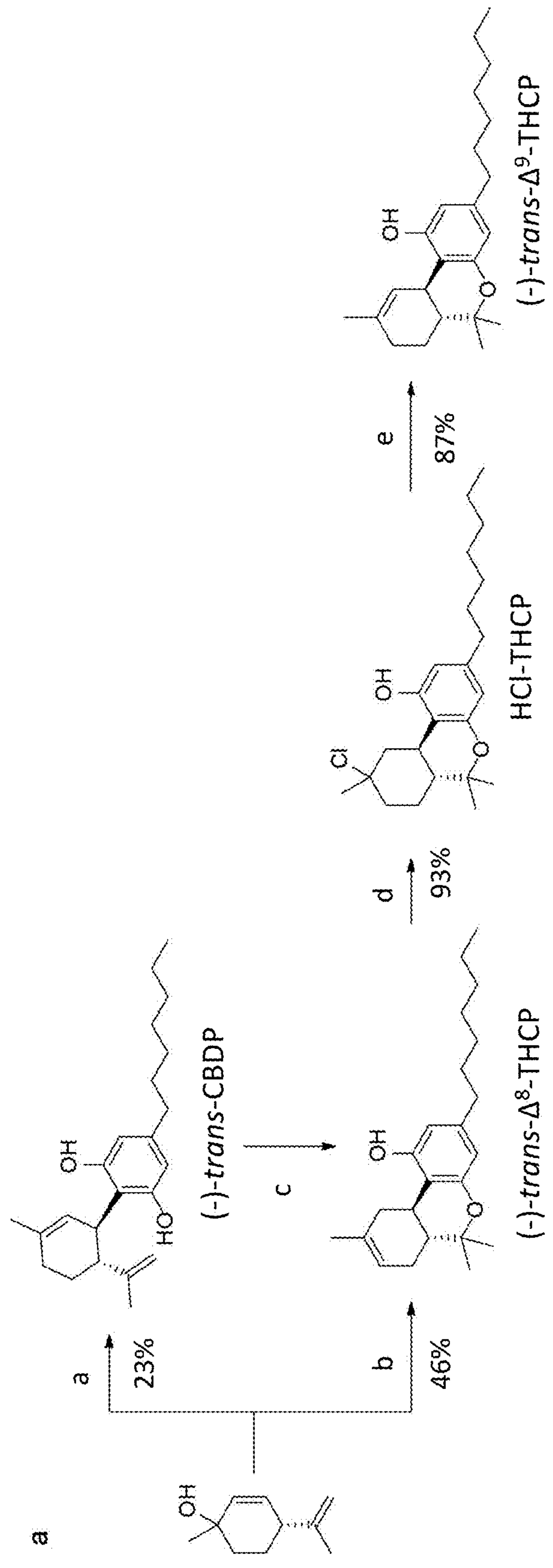
FIGS. 18(A), 18(B), 18(C), 18(D), 18(E), 18(F) and 18(G), collectively, show synthesis and spectroscopic characterization of (−)-trans-CBDP and (−)-trans-$\Delta^9$-THCP, according to an exemplary embodiment of the present disclosure.

3.1.3 Stereoselective synthesis of CBDP and THCP. (−)-trans-Cannabidiphorol ((−)-trans-CBDP) and (−)-trans-$\Delta^9$-tetrahydrocannabiphorol ((−)-trans-$\Delta^9$-THCP) were stereoselectively synthesized as previously reported for the synthesis of (−)-trans-CBDB and (−)-trans-$\Delta^9$-THCB homologues[11,16]. Accordingly, (−)-trans-CBDP was prepared by condensation of 5-heptylbenzene-1,3-diol (1) with (1S,4R)-1-methyl-4-(prop-1-en-2-yl)cycloex-2-enol, using pTSA as catalyst, for 90 min. Longer reaction time did not improve the yield of (−)-trans-CBDP because cyclization of (−)-trans-CBDP to (−)-trans-$\Delta^9$-THCP and then to (−)-trans-$\Delta^8$-THCP occurs. 5-heptylbenzene-1,3-diol (1) was synthesized first as reported in the Exhibit C—Supporting Information (Supplementary FIG. SI-1). The conversion of (−)-trans-CBDP to (−)-trans-$\Delta^9$-THCP using diverse Lewis' acids, as already reported in the literature for the synthesis of the homologue $\Delta^9$-THC[19-21], led to a complex mixture of isomers which results in an arduous and low-yield isolation of (−)-trans-$\Delta^9$-THCP by standard chromatographic techniques. Therefore, for the synthesis of (−)-trans-$\Delta^9$-THCP, its regioisomer (−)-trans-$\Delta^8$-THCP was synthesized first by condensation of 5-heptylbenzene-1,3-diol with (1S,4R)-1-methyl-4-(prop-1-en-2-yl)cycloex-2-enol, as described above, but the reaction was left stirring for 48 hours. Alternatively, (−)-trans-CBDP could be also quantitatively converted to (−)-trans-$\Delta^8$-THCP in the same conditions. Hydrochlorination of the $\Delta^8$ double bond of (−)-trans-$\Delta^8$-THCP, using ZnCl2 as catalyst, allowed to obtain (−)-trans-HCl-THCP, which was successively converted to (−)-trans-$\Delta^9$-THCP in 87% yield by selective elimination on 2 position of the terpene moiety using potassium t-amylate as base (FIG. 18*a*).

Figure 18B:
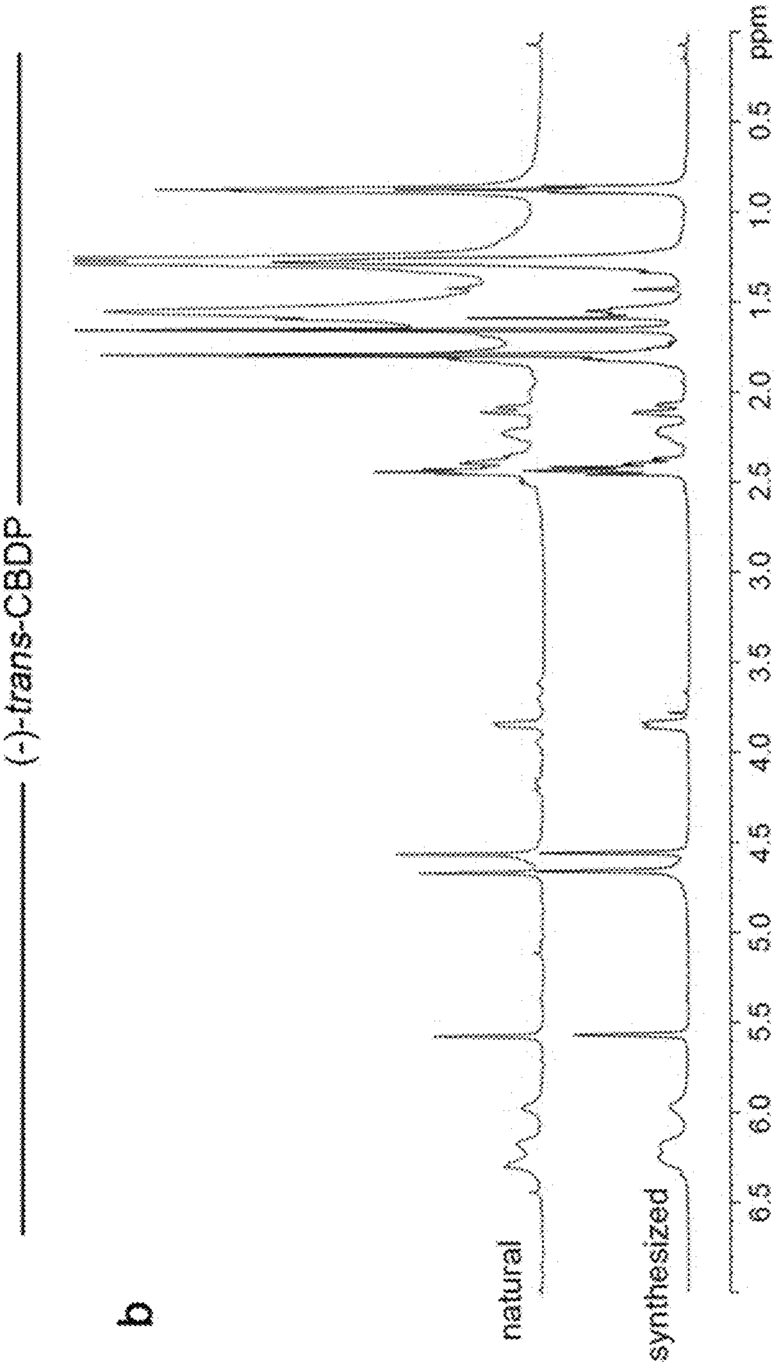
Figure 18C:
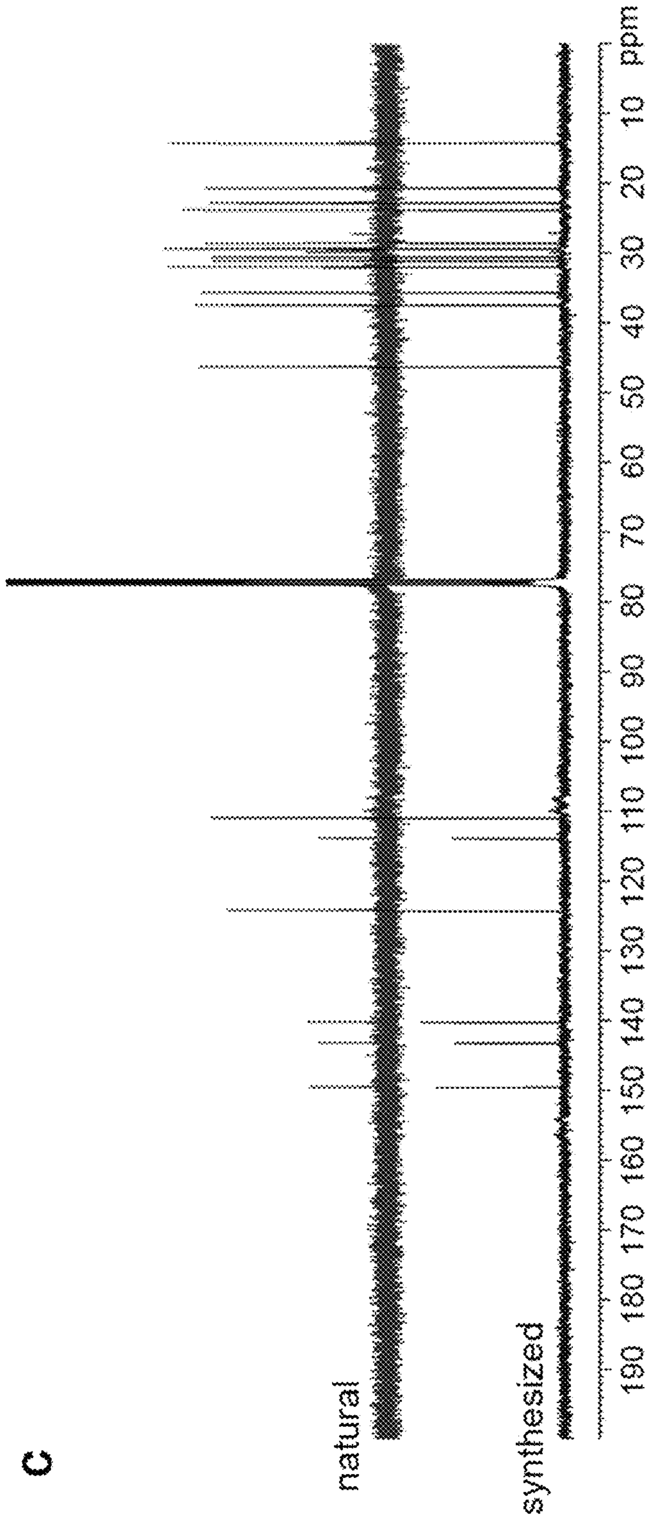
Figure 18D:
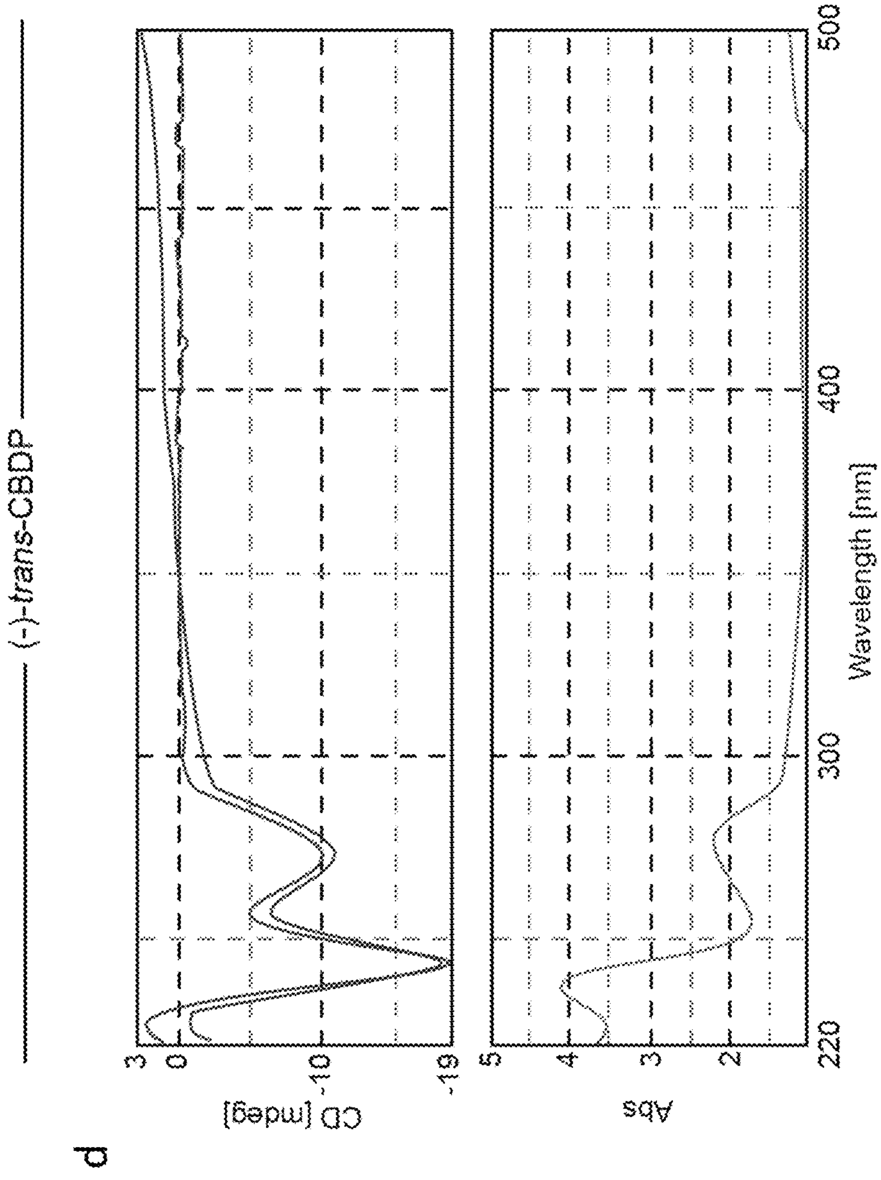
Figure 18E:
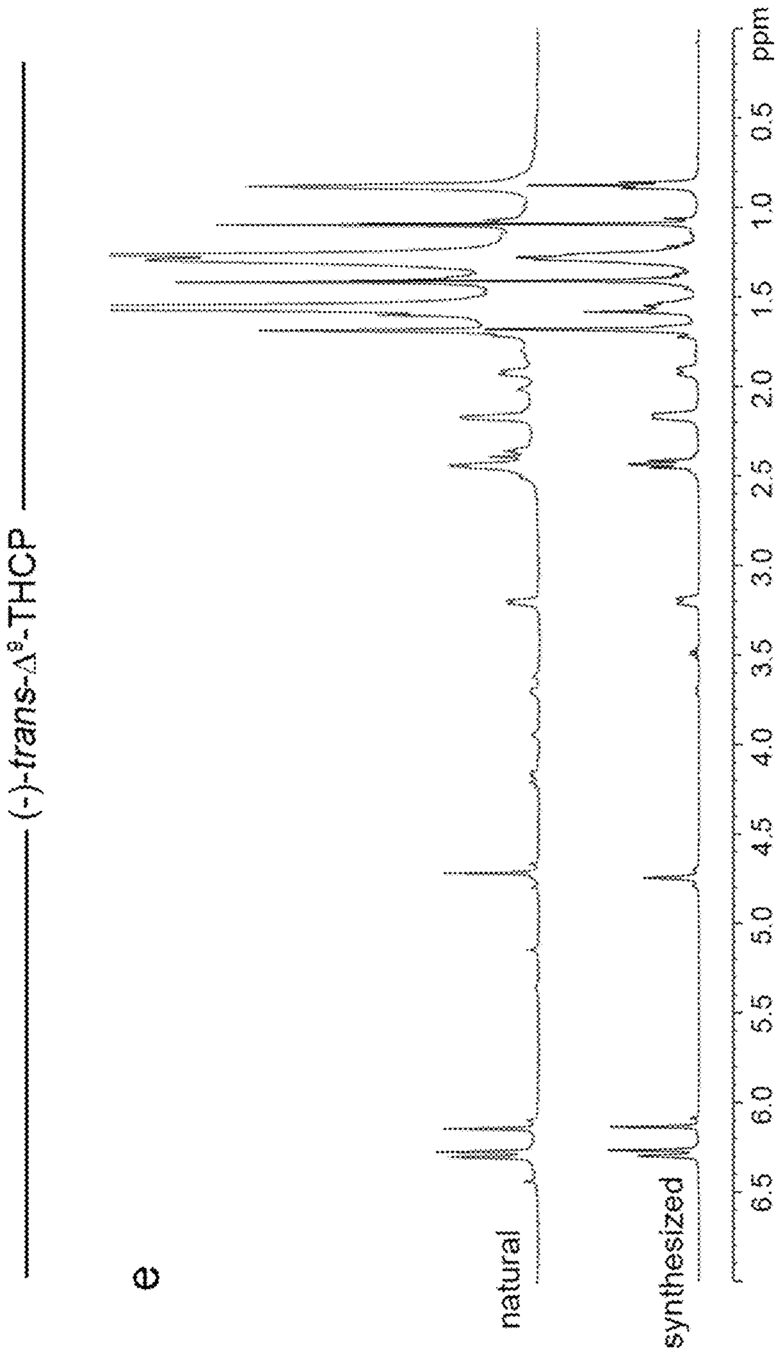
Figure 18F:
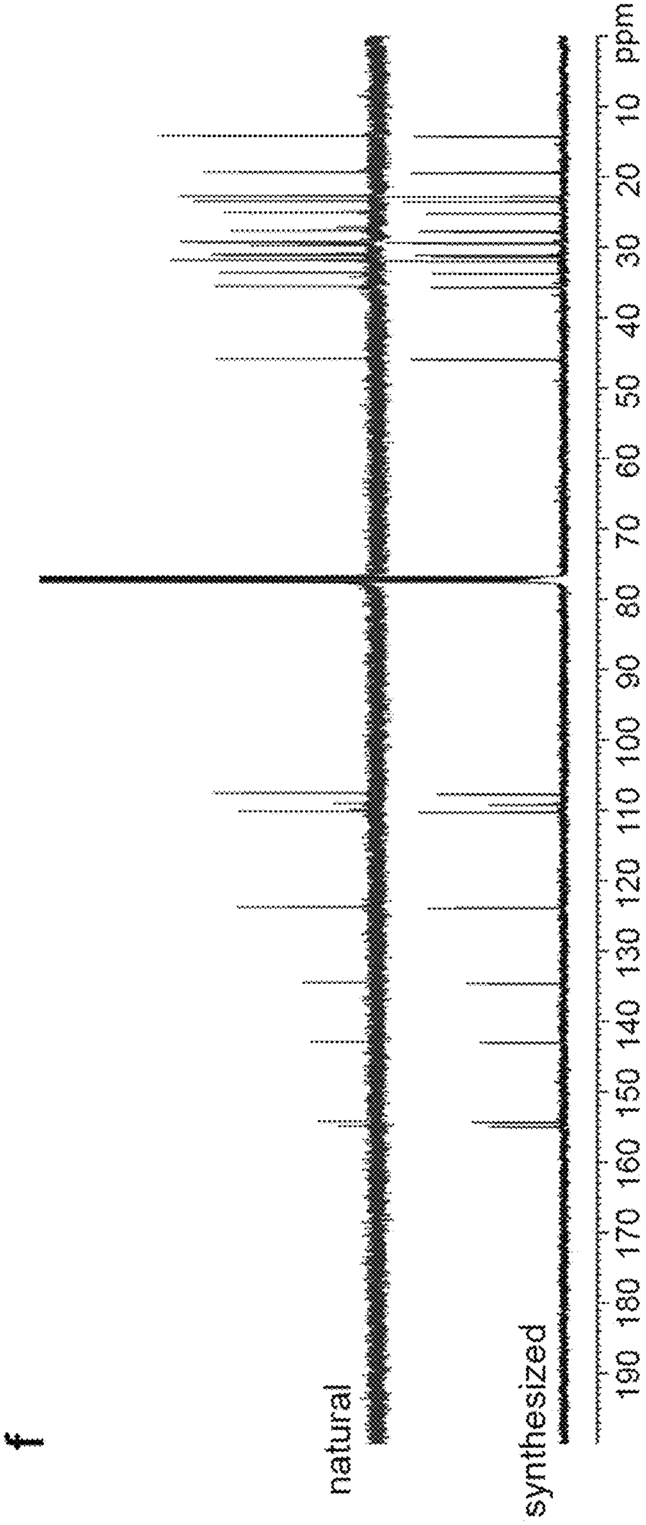
Figure 18G:
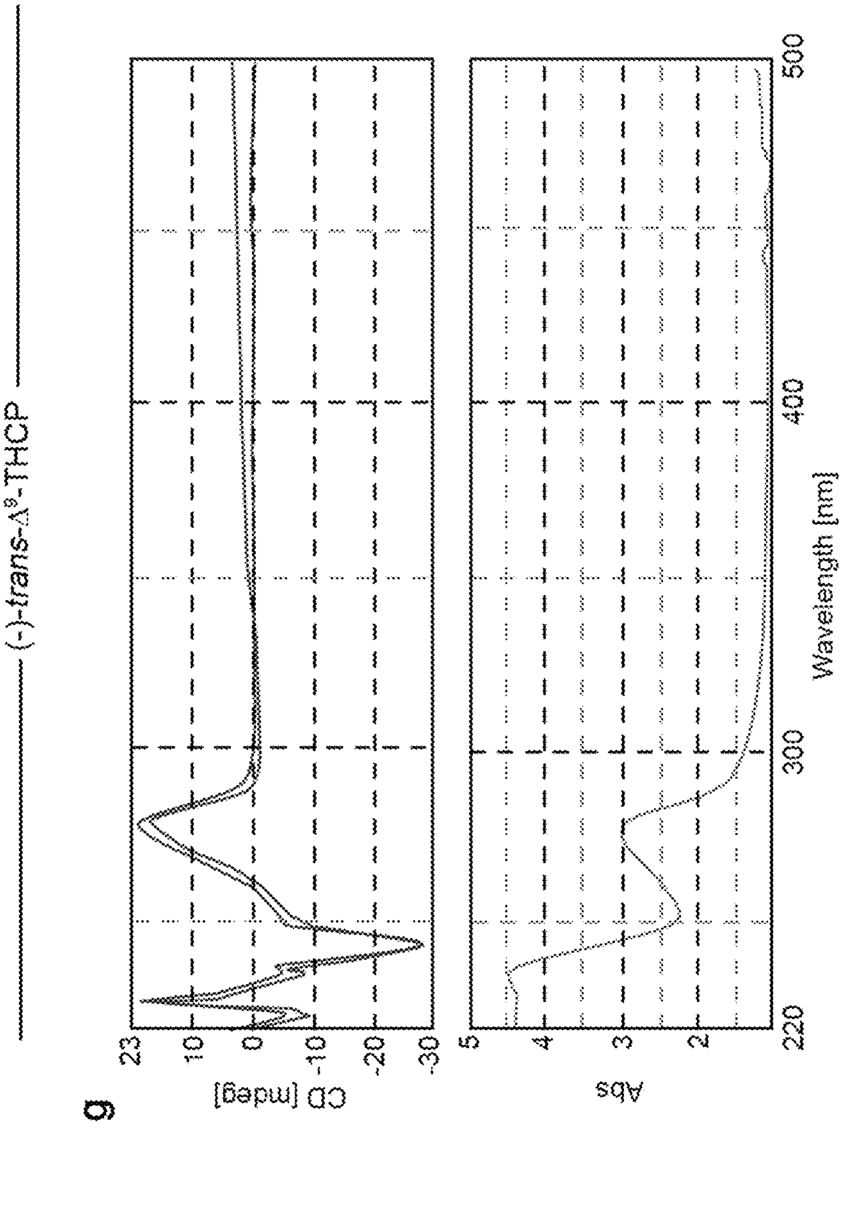

The chemical identification of synthetic (−)-trans-CBDP and (−)-trans-$\Delta^9$-THCP, and its $^1H$ and $^{13}C$ assignments were achieved by NMR spectroscopy (Supplementary Table SI-1,2 and Supplementary Figure SI-2,3 in Exhibit C). Since (−)-trans-CBDP and (−)-trans-$\Delta^9$-THCP differ from the respective homologues (CBD, CBDB, CBDV, $\Delta^9$-THC, $\Delta^9$-THCB and $\Delta^9$-THCV) solely for the length of the alkyl chain on the resorcinyl moiety, no significative differences in the proton chemical shifts of the terpene and aromatic moieties were observed for CBD and $\Delta^9$-THC homologues. The perfect match in the chemical shift of the terpene and aromatic among the synthesized (−)-trans-CBDP and (−)-trans-$\Delta^9$-THCP and the respective homologues[11, 16, 22], combined with the mass spectra and fragmentation pattern, allowed us to determine the chemical structures of the two new synthetic cannabinoids. The trans configuration at the terpene moiety was determined by optical rotatory power. The new cannabinoids (−)-trans-CBDP and (−)-trans-$\Delta^9$-THCP showed an $[\alpha]_D^{20}$ of −145° and 163°, respectively, in chloroform. The $[\alpha]_D^{20}$ values are in line with those of the homologues[11,23], suggesting a (1R,6R) configuration for both CBDP and $\Delta^9$-THCP. A perfect superimposition between the $^1$H (FIG. 18*b,e*) and $^{13}$C NMR spectra (FIG. 18*c,f*) and the circular dichroism absorption (FIG. 18*d,g*) of both synthetic and extracted (−)-trans-CBDP and (−)-trans-$\Delta^9$-THCP was observed, determining the identity of the two new cannabinoids identified in the FM2 *cannabis* variety.

Figure 19A:
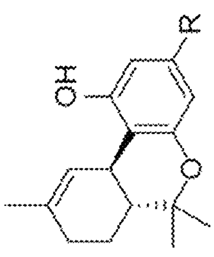
FIGS. 19(A) and 19(B) shows in vitro activity and docking calculation of $\Delta^9$-THCP, according to an exemplary embodiment of the present disclosure.
Figure 19B:
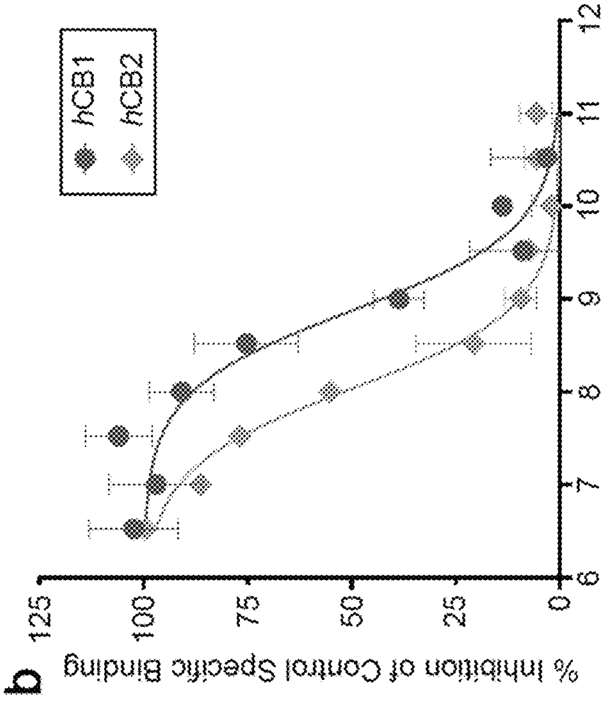

3.1.4 Binding affinity at human $CB_1$ and $CB_2$ receptors. The binding affinity of (−)-trans-$\Delta^9$-THCP against purified human $CB_1$ and $CB_2$ receptors was determined in a radioligand binding assay, using [$^3$H]CP55940 or [$^3$H]WIN 55212-2 as reference compounds, and dose-response curves were determined (FIGS. 19*a* and 19*b*). (−)-trans-$\Delta^9$-THCP binds with high affinity to both human $CB_1$ and $CB_2$ receptors with a $K_i$ of 1.2 and 6.2 nM, respectively. (−)-trans-$\Delta^9$-THCP results 33-times more active than (−)-trans-$\Delta^9$-THC ($K_i$=40 nM), 63-times more active than (−)-trans-$\Delta^9$-THCV ($K_i$ of 75.4 nM) and 13-times more active than the newly discovered (−)-trans-$\Delta^9$-THCB ($K_i$ of 15 nM) against $CB_1$ receptor[12,14]. Moreover, the new identified (−)-trans-$\Delta^9$-THCP resulted about 5- to 10-times more active against $CB_2$ receptor ($K_i$ of 6.2 nM), in contrast with (−)-trans-$\Delta^9$-THC, (−)-trans-$\Delta^9$-THCB and (−)-trans-$\Delta^9$-THCV, which instead show a comparable biding affinity with a $K_i$ ranging from 36 to 63 nM (FIG. 19*a*)[12,14].

Figure 19C:
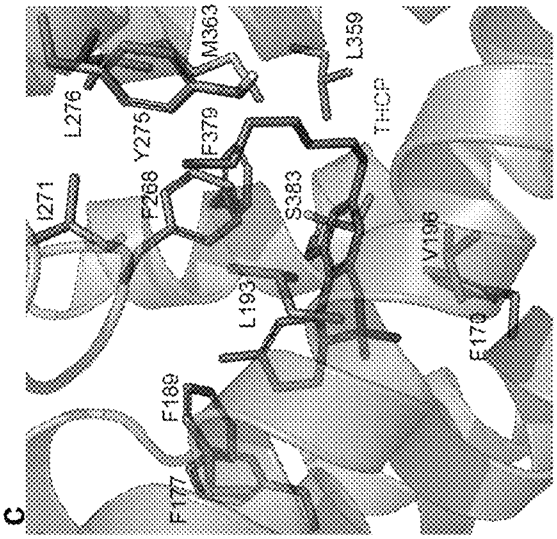
FIG. 19(C) shows docking pose of (−)-trans-$\Delta^9$-THCP (blue sticks), in complex with $hCB_1$ receptor (PDB ID: 5XRA, orange cartoon), according to an exemplary embodiment of the present disclosure. Key amino acidic residues are reported in orange sticks. H-bond are reported in yellow dotted line. Heteroatoms are color-coded: oxygen in red, nitrogen in blue and sulphur in yellow.
Figure 19D:
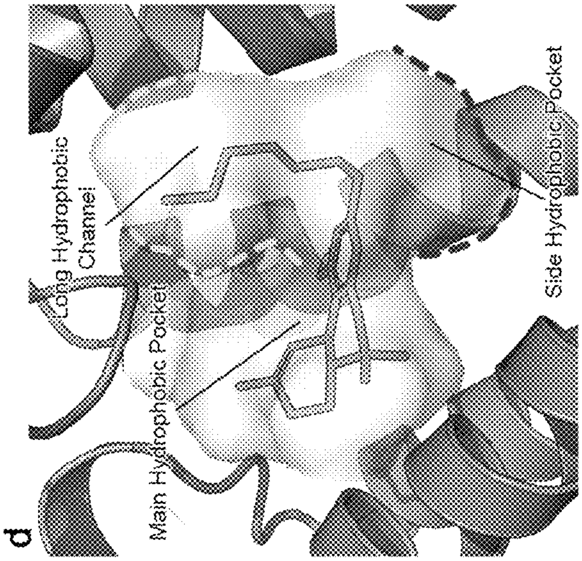
FIG. 19(D) shows binding pocket of $hCB_1$ receptor, highlighting the positioning of the heptyl chain within the long hydrophobic channel of the receptor (yellow dashed line), according to an exemplary embodiment of the present disclosure. The side hydrophobic pocket is bordered in magenta.

The highest activity of (−)-trans-$\Delta^9$-THCP, compared to the shorter homologues, was investigated by docking calculation. The X-ray structure of the active conformation of human $CB_1$ receptor in complex with the agonist AM11542 (PDB ID: 5XRA) was used as reference for docking since marked structural changes in the orthosteric ligand-binding site are observed in comparison with the conformation of the receptor bound to an antagonist[24,25]. AM11542 is a synthetic $\Delta^8$ cannabinoid with high affinity against $hCB_1$ receptor ($K_i$=0.11 nM) possessing a 7'-bromo-1',1'-dimethyl-heptyl aliphatic chain at C3 of the resorcinyl moiety. Due to the close chemical similarity, the predicted binding mode of (−)-trans-$\Delta^9$-THCP (FIG. 19*c*) reflects that of AM11542 in the $CB_1$ crystal structure (FIG. SI-6*a,b*)[18]. (−)-trans-$\Delta^9$-THCP binds in the active conformation of $CB_1$ in an L-shaped pose. The tetrahydro-6H-benzo[c]chromene ring system is located within the main hydrophobic pocket delimited by Phe174, Phe177, Phe189, Lys193, Pro269, Phe170 and Phe268. In particular, the aromatic ring of the resorcinyl moiety is involved in two edge-to-face π-π interactions with Phe170 and Phe268, whereas the phenolic hydroxyl group at C1 is engaged in a H-bond with Ser383 (FIG. 19*c*). Interestingly, the heptyl chain at C3 extends into a long hydrophobic tunnel formed by Leu193, Val196, Tyr275, Iso271, Leu276, Trp279, Leu359, Phe379 and Met363 (FIG. 19*c,d*). Because the predicted pose of the tricyclic tetrahydrocannabinol ring system is conserved among the four THC homologues (Supplementary FIG. SI-7*a-c* in Exhibit C), the length of the alkyl chain at C3 of the resorcinyl moiety could account for the different binding affinity observed among the four cannabinoids. (−)-trans-$\Delta^9$-THCP (FIG. 19*c*) and (−)-trans-$\Delta^9$-THC (Supplementary FIG. SI-7*a* in Exhibit C) share the same positioning of the alkyl 'tail' within the hydrophobic channel[12, 25, 26]. However, the long heptyl chain of $\Delta^9$-THCP is able to extend into the tunnel along its entire length, maximizing the hydrophobic interactions with the residues of the side channel. In contrast, the tunnel is only partially occupied by the shorter pentyl chain of (−)-trans-$\Delta^9$-THC, accounting for the higher affinity of $\Delta^9$-THCP ($K_i$=1.2 nM) compared to $\Delta^9$-THC ($K_i$=40 nM). A different positioning of the 'tail' is instead predicted for the shorter alkyl chain homologues, $\Delta^9$-THCV and $\Delta^9$-THCB. The propyl and butyl chain of $\Delta^9$-THCV and $\Delta^9$-THCB, respectively, are too short to effectively extend within the hydrophobic channel. As stated in our previous work[12], these shorter chains accommodate within a small hydrophobic pocket delimitated by Phe200, Leu359 and Met363 (Supplementary FIG. SI-7*b,c* in Exhibit C). This side pocket is located at the insertion between the main hydrophobic pocket and the long channel (FIG. 19*d*) and seems to accommodate small hydrophobic substituents (i.e. gem-dimethyl or cycloalkyl) introduced at C1' position of the side chain of several synthetic cannabinoids, rationalizing the notable enhancement in potency and affinity for these derivatives[27-31].

Figure 20A:
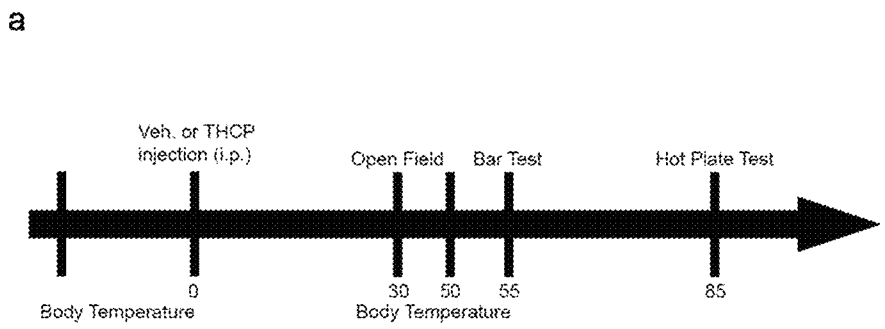
FIGS. 20(A), 20(B), 20(C), 20(D), 20(E) and 20(F), collectively, show dose-dependent effects of $\Delta^9$-THCP administration (2.5, 5, or 10 mg/kg, i.p.) on the tetrad phenotypes in mice in comparison to vehicle, according to an exemplary embodiment of the present disclosure.
Figure 20B:
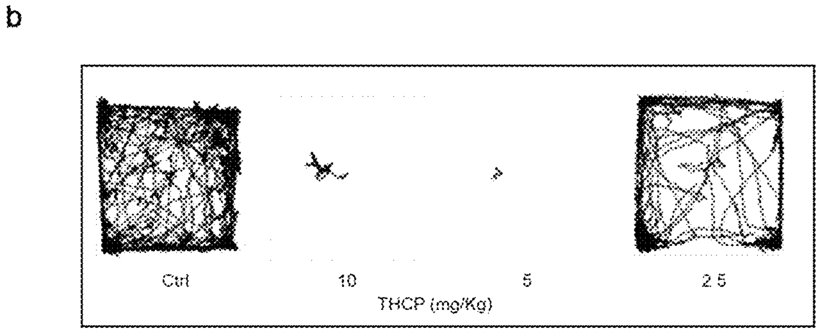
Figure 20C:
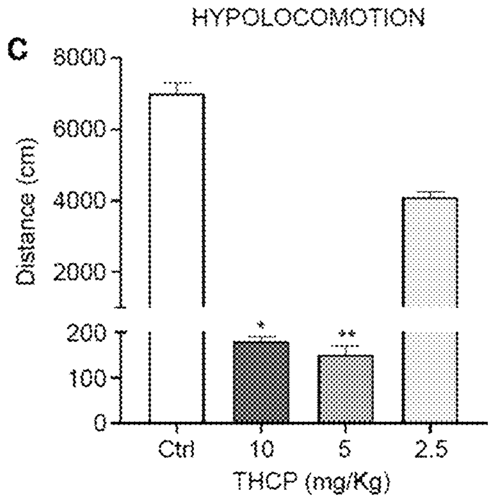
Figure 20D:
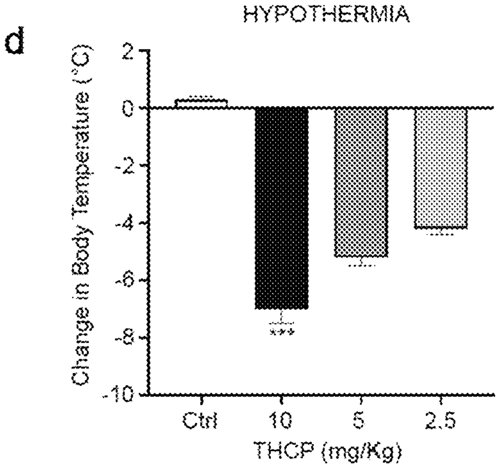
Figure 20E:
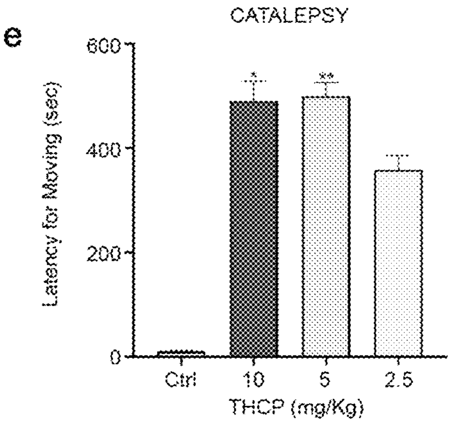
Figure 20F:
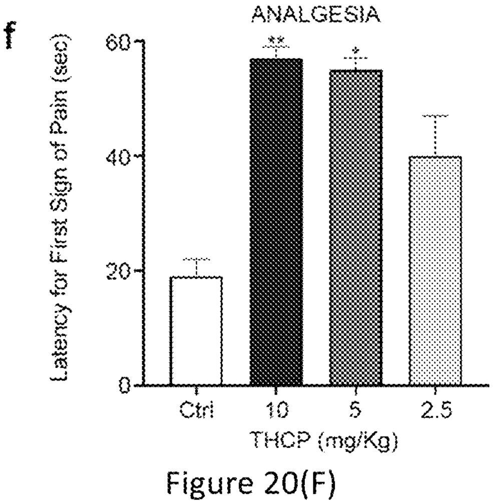

3.1.5 In vivo determination of the cannabinoid profile of THCP. The cannabinoid activity of $\Delta^9$-THCP was evaluated by the tetrad of behavioural tests on mice. The tetrad includes the assessment of spontaneous activity, immobility index (catalepsy), analgesia and changes in rectal temperature. Decrease of locomotor activity, catalepsy, analgesia and hypothermia are well-known signs of physiological manifestations of cannabinoid activity[32]. After intraperitoneal (i.p.) administration, $\Delta^9$-THCP at 2.5 mg/kg markedly reduced the spontaneous activity of mice in the open field, while at 5 and 10 mg/kg it induced catalepsy on the ring with the immobility as compared to the vehicle treated mice (FIG. 20*b,c*) (0: 6888 cm±474.8, 10 mg/kg: 166.8 cm±20.50, 5 mg/kg: 127.5 cm±31.32, 2.5 mg/kg: 4072 cm±350.8, p=0.0009). Moreover, $\Delta^9$-THCP administration induced a significant increase, at 10 and 5 mg/kg, in the latency for moving from the catalepsy bar (FIG. 20*e*) (0: 15.20 sec±4.33, 10 mg/kg: 484.5 sec±51.58, 5 mg/kg: 493.4 sec±35.68, 2.5 mg/kg: 346.1 sec±35.24, p=0.0051). In the hot plate test (FIG. 20*f*), $\Delta^9$-THCP (10 and 5 mg/kg) induced antinociceptive effect, whereas at 2.5 mg/kg there is a trend in the induction of antinociception, which resulted not statistically significant as compared to the vehicle treated mice (0: 19.20 sec±2.65, 10 mg/kg: 57.0 sec±2.0, 5 mg/kg: 54.38 sec±2.86, 2.5 mg/kg: 40.22 sec±5.8, p=0.0044). $\Delta^9$-THCP administration induced a dose dependent significant decrease, only 10 mg/kg, in body temperature as compared to vehicle (0: 0.40° C.±0.25, 10 mg/kg: −7.10° C.±0.43, 5 mg/kg: −5.28° C.±0.36, 2.5 mg/kg: −4.12° C.±0.38, p=0.0009) (FIG. 20*d*).

3.1.6 Semi-quantification of CBDP and $\Delta^9$-THCP in the FM2 extract. A semi-quantification method based on LC-HRMS allowed to provide an approximate amount of the two new phytocannabinoids in the FM2 ethanol extract. Their pentyl homologues, CBD and $\Delta^9$-THC, showed a concentration of 56 and 39 μg/mL respectively, in accordance with the values provided by the Military Chemical Pharmaceutical Institute (59 mg/g and 42 mg/g for CBD and $\Delta^9$-THC respectively), obtained by the official GC-FID quantitative method. The same semi-quantitative method provided an amount of about 243 and 29 μg/g for CBDP and $\Delta^9$-THCP respectively.

3.2 DISCUSSION

Up to now, almost 150 phytocannabinoids have been detected in *cannabis* plant[7, 33, 34], though most of them have neither been isolated nor characterized. The well-known CBD and $\Delta^9$-THC have been extensively characterized and proved to possess interesting pharmacological profiles[35-39], thus the attention towards the biological activity of their known homologues like CBDV and $\Delta^9$-THCV has recently grown as evidenced by the increasing number of publications per year appearing on Scopus. Other homologues like those belonging to the orcinoid series are scarcely investigated likely due to their low amount in the plant that makes their isolation challenging. In recent years, the agricultural genetics research has made great progresses on the selection of rare strains that produce high amounts of CBDV, CBG and $\Delta^9$-THCV[40-42], thus it would not be surprising to see in the near future *cannabis* varieties rich in other minor phytocannabinoids. This genetic selection would enable the production of extracts rich in a specific phytocannabinoid with a characteristic pharmacological profile. For this reason, it is important to carry out a comprehensive chemical profiling of a medicinal *cannabis* variety and a thorough investigation of the pharmacological activity of minor and less known phytocannabinoids.

As the pharmacological activity of $\Delta^9$-THC is particularly ascribed to its affinity for $CB_1$ receptor, the literature suggests that the latter can be increased by elongating the alkyl side chain, which represents the main cannabinoid pharmacophoric driving force[14]. Therefore, taking THC as the lead compound, a series of cannabinoids have been chemically synthesized and their biological potency resulted several times higher than $\Delta^9$-THC itself[15]. To the best of our knowledge, naturally occurring cannabinoids with a linear alkyl side chain longer than five terms have never been detected or even putatively identified in *cannabis* plant. However, the cutting-edge technological platform of the Orbitrap mass spectrometry and the use of advanced analytical techniques like metabolomics can enable the discovery and identification of new compounds with a high degree of confidence even when present in traces in complex matrices[34,43]. In the present work, we report for the first time the isolation and full characterization of two new CBD and $\Delta^9$-THC heptyl homologs, which we named cannabidiphorol (CBDP) and $\Delta^9$-tetrahydrocannabiphorol ($\Delta^9$-THCP), respectively. These common names were derived from the traditional naming of phytocannabinoids based on the resorcinyl residue, in this case corresponding to sphaerophorol.

The biological results obtained in the in vitro binding assay indicated an affinity for $CB_1$ receptor more than thirty-fold higher compared to the one reported for $\Delta^9$-THC in the literature[14]. Also, this encouraging data was supported by in vivo evaluation of the cannabimimetic activity by the tetrad test, where $\Delta^9$-THCP decreased locomotor activity and rectal temperature, induced catalepsy and produced analgesia miming the properties of full $CB_1$ receptor agonists (FIG. 20). In particular, $\Delta^9$-THCP proved to be as active as $\Delta^9$-THC but at lower doses. In fact, the minimum THC dose used in this kind of test is 10 mg/kg, whereas $\Delta^9$-THCP resulted active at 5 mg/kg in three of the four tetrad tests. These results, accompanied by the docking data, are in line with the extensive structure-activity relationship (SAR) studies performed through the years on synthetic cannabinoids, revealing the importance of the length of the alkyl chain in position 3 on the resorcinyl moiety in modulating the ligand affinity at $CB_1$ receptor.

Although the amount of the heptyl homologues of CBD and $\Delta^9$-THC in the FM2 variety could appear trifling, both in vitro and in vivo preliminary studies reported herein on $\Delta^9$-THCP showed a cannabimimetic activity several times higher than its pentyl homologue $\Delta^9$-THC. Moreover, it is reasonable to suppose that other *cannabis* varieties may contain even higher percentages of $\Delta^9$-THCP. It is also important to point out that there exists an astonishing variability of subject response to a *cannabis*-based therapy even with an equal $\Delta^9$-THC dose[44-46]. It is therefore possible that the psychotropic effects are due to other extremely active phytocannabinoids such as $\Delta^9$-THCP. However, up to now nobody has ever searched for this potent phytocannabinoid in medicinal *cannabis* varieties. In our opinion, this compound should be included in the list of the main phytocannabinoids to be determined for a correct evaluation of the pharmacological effect of the *cannabis* extracts administered to patients.

Ongoing studies are devoted to the investigation of the pharmacological activity of CBDP and to expand that of $\Delta^9$-THCP. It is known that CBD binds with poor affinity to both $CB_1$ and $CB_2$ receptors[47], thus the evaluation of the cannabimimetic activity of CBDP does not appear to be appropriate. On the other hand, more suitable tests should regard its anti-inflammatory, anti-oxidant and anti-epileptic activity typical of CBD[38]. Anyway, the discovery of an extremely potent THC-like phytocannabinoid may shed light on several pharmacological effects not ascribable solely to $\Delta^9$-THC.

3.3 METHODS

Plant Material. FM2 *cannabis* variety is obtained from the strain CIN-RO produced by the Council for Agricultural Research and Economics (CREA) in Rovigo (Italy) and provided to the Military Chemical Pharmaceutical Institute (MCPI, Firenze, Italy) for breeding. FM2 inflorescence (batch n. 6A 32/1) was supplied by the MCPI with the authorization of the Italian Ministry of Health (prot. n. SP/062). The raw plant material (10 g) was finely grinded and divided into two batches: one batch (500 mg) was extracted with 50 mL of ethanol 96% according to the procedure indicated by the monograph of *Cannabis Flos* of the German Pharmacopoeia[48] and was analyzed by UHPLC-HESI-Orbitrap after proper dilution with acetonitrile (×100). The remaining 9.5 g were extracted following the protocol of Pellati et al. with some modifications[18]. Briefly, freeze-dried plant material was extracted with 400 mL of n-hexane for 15 min under sonication in an ice bath. Samples were centrifuged for 10 min at 2000×g and the pellets were discarded. The procedure was repeated twice more. The supernatants were then dried under reduce pressure and resuspended in 10 mL of acetonitrile, filtered and used for the isolation of CBDPA and THCPA by semi-preparative liquid chromatography.

Isolation of Natural CBDP and $\Delta^9$-THCP. Aliquots (1 mL) of the solution obtained as described in the 'Plant Material' section were injected in a semi-preparative LC system (Octave 10 Semba Bioscience, Madison, USA). The chromatographic conditions used are reported in the paper by Citti et al.[11]. The column employed was a Luna Cis with a fully porous silica stationary phase (Luna 5 μm C18(2) 100 Å, 250×10 mm) (Phenomenex, Bologna, Italy) and a mixture of acetonitrile:0.1% aqueous formic acid 70:30 (v/v)

was used as mobile phase at a flow rate of 5 mL/min. CBDPA and THCPA (retention time 19.0 min and 75.5 min respectively) were isolated as reported in our previous work[11]. The fractions containing CBDBA and THCBA were analyzed by UHPLC-HESI-Orbitrap. The fractions containing predominantly either one or the other cannabinoid were separately combined and dried on the rotavapor at 70° C. Each residue was subjected to decarboxylation at 120° C. for two hours in oven. An amount of about 0.6 mg of CBDP and about 0.3 mg of $\Delta^9$-THCP were obtained.

UHPLC-HESI-Orbitrap Metabolomic Analysis. FM2 extracts were analyzed on a Thermo Fisher Scientific Ultimate 3000 system equipped with a vacuum degasser, a binary pump, a thermostated autosampler, a thermostated column compartment and interfaced to a heated electrospray ionization source and a Q-Exactive Orbitrap mass spectrometer (UHPLC-HESI-Orbitrap). The parameters of the HESI source were set according to Citti et al.[11]: capillary temperature, 320° C.; vaporizer temperature, 280° C.; electrospray voltage, 4.2 kV (positive mode) and 3.8 kV (negative mode); sheath gas, 55 arbitrary units; auxiliary gas, 30 arbitrary units; S lens RF level, 45. Analyses were acquired using the Xcalibur 3.0 software (Thermo Fisher Scientific, San Jose, CA, USA) in full scan data-dependent acquisition (FS-dd-$MS^2$) in positive (ESI+) and negative (ESI−) mode at a resolving power of 70,000 FWHM at m/z 200. A scan range of m/z 250-400, an AGC of 3e6, an injection time of 100 ms and an isolation window for the filtration of the precursor ions of m/z 0.7 were chosen as the optimal parameters for the mass analyzer. A normalized collision energy (NCE) of 20 was used to fragment the precursor ions. Extracted ion chromatograms (EIC) of the $[M+H]^+$ and $[M-H]^-$ molecular ions were derived from the total ion chromatogram (TIC) of the FM2 extracts and matched with pure analytical standards for accuracy of the exact mass (5 ppm), retention time and MS/MS spectrum.

The chromatographic separation was carried out on a Poroshell 120 SB-C18 (3.0×100 mm, 2.7 μm, Agilent, Milan, Italy) following the conditions employed for our previous work". A semi-quantitative analysis of $\Delta^9$-THC and CBD and their heptyl analogs CBDP and $\Delta^9$-THCP was achieved using a calibration curve with an external standard. A stock solution of CBD and $\Delta^9$-THC, CBDP and $\Delta^9$-THCP (1 mg/mL) were properly diluted to obtain five non-zero calibration points at the final concentrations of 50, 100, 250, 500 and 1000 ng/mL for CBD and $\Delta^9$-THC and of 1, 5, 10, 25 and 50 ng/mL for CBDP and $\Delta^9$-THCP. A deuterated standard of $\Delta^9$-THC-$d_3$ was added at each calibration standard at a final concentration of 50 ng/mL. The linearity was assessed by the coefficient of determination ($R^2$), which was greater than 0.993 for each analyte.

3.4 SYNTHETIC PROCEDURE

All commercially available reagents and solvents were used as purchased, without further purification unless otherwise specified. The following solvents have been abbreviated: diethyl ether ($Et_2O$); dichloromethane (DCM); cyclohexane (CE). Reactions were monitored by thin-layer chromatography on silica gel plates (60F-254, E. Merck) and visualized with UV light, or alkaline $KMnO_4$ aqueous solution. Reaction products were purified, when necessary, by flash chromatography on silica gel (40-63 μm) with the solvent system indicated. NMR spectra were recorded on a Bruker 400 or Bruker 600 spectrometer working respectively at 400.134 MHz and 600.130 MHz for $^1H$ and at 100.62 MHz or 150.902 MHz for $^{13}C$. Chemical shifts (δ) are in parts per million (ppm) and they were referenced to the solvent residual peaks ($CDCl_3$ δ=7.26 ppm for proton and δ=77.20 ppm for carbon). Coupling constants are reported in hertz (Hz). Splitting patterns are designed following abbreviations are used: singlet (s), doublet (d), triplet (t), quartet (q), double doublet (dd), quintet (quin), multiplet (m), broad signal (br s). Monodimensional spectra were acquired with a spectral width of 8278 Hz (for $^1H$-NMR) and 23.9 kHz (for $^{13}C$-NMR), a relaxation delay of 1 s, and 32 and 1024 number of transients for $^1H$-NMR and $^{13}C$-NMR, respectively. The COSY were recorded as a 2048×256 matrix with 2 transients per t1 increment and processed as a 2048×1024 matrix. The HSQC spectra were collected as a 2048×256 matrix with 4 transients per t1 increment and processed as a 2048×1024 matrix, and the one-bond heteronuclear coupling value was set to 145 Hz. The HMBC spectra were collected as a 4096×256 matrix with 16 transients per t1 increment and processed as a 4096×1024 matrix, and the long-range coupling value was set to 8 Hz. Circular dichroism (CD) and UV spectra were acquired on a Jasco (Tokyo, Japan) J-1100 spectropolarimeter using a 50 nm/min scanning speed. Quartz cells with a 10 mm path length were employed to record spectra in the 500-220 nm range. Optical rotation (λ) was measured with a Polarimeter 240C (cell-length 100 mm, volume 1 mL) from Perkin-Elmer (Milan, Italy).

3.4.1 Synthesis of (1'R,2'R)-4-heptyl-5'-methyl-2'-(prop-1-en-2-yl)-1',2',3',4'-tetrahydro-[1,1'-biphenyl]-2,6-diol, (−)-trans-CBDP (1S,4R)-1-methyl-4-(prop-1-en-2-yl)cycloex-2-enol (146 mg, 0.96 mmol, 0.9 eq.), solubilized in 15 mL of anhydrous DCM, was added over a period of 20 minutes to a stirred solution of 5-heptylbenzene-1,3-diol (1) (222 mg, 1.07 mmol, 1 eq.) and p-toluenesulfonic acid (20 mg, 0.11 mmol, 0.1 eq.) in anhydrous DCM (15 mL) at room temperature and over a positive pressure of argon. After stirring in the same conditions for 1 h, the reaction was quenched with 10 mL of a saturated aqueous solution of $NaHCO_3$. The mixture was partitioned between diethyl ether and water. The organic layer was separated and washed with brine, dried with anhydrous $Na_2SO_4$ and evaporated. The residue was chromatographed (ratio crude:silica 1/120, eluent:CE:DCM 8/2). All the chromatographic fractions were analyzed by HPLC-UV and UHPLC-HESI-Orbitrap and only the fractions containing exclusively CBDP were concentrated to give 76 mg of a colorless oil (23% yield, purity>99%). $^1H$ NMR (400 MHz, $CDCl_3$) δ 6.10-6.30 (m, 2H), 5.97 (bs, 1H), 5.57 (s, 1H), 4.66 (s, 1H), 4.66 (bs, 1H), 4.56 (s, 1H), 3.89-3.81 (m, 1H), 2.52-2.35 (m, 3H), 2.24 (td, J=6.1, 12.7 Hz, 1H), 2.09 (ddt, J=2.4, 5.1, 17.9 Hz, 1H), 1.89-1.74 (m, 5H), 1.65 (s, 3H), 1.55 (qnt, J=7.6 Hz, 2H), 1.28 (td, J=4.7, 8.2, 9.0 Hz, 8H), 0.87 (t, J=6.7 Hz, 3H). $^{13}C$ NMR (101 MHz, $CDCl_3$) δ 156.27, 154.09, 149.56, 143.23, 140.22, 124.30, 113.93, 111.01, 109.91, 108.26, 46.33, 37.46, 35.70, 31.99, 31.14, 30.59, 29.43, 29.35, 28.60, 23.86, 22.84, 20.71, 14.29. HRMS m/z $[M+H]^+$ calcd. for $C_{23}H_{35}O_2^+$: 343.2632. Found: 343.2629; $[M-H]^-$ calcd. for $C_{23}H_{33}O_2^-$: 341.2475. Found: 341.2482. $[\alpha]_D^{20}$−146° (c=1.0, ACN).

3.4.2 Synthesis of (6aR,10aR)-3-heptyl-6,6,9-trimethyl-6a,7,10,10a-tetrahydro-6H-benzo[c]chromen-1-ol, (−)-trans-$\Delta^8$-THCP The set-up of the reaction for the synthesis of (−)-trans-$\Delta^8$-THCP was performed as described for (−)-trans-CBDP and the resulting mixture was stirred at room temperature for 48 hours. The mixture was diluted with diethyl ether, and washed with a saturated solution of $NaHCO_3$(10 mL). The organic layer was collected, washed with brine, dried (anhydrous $Na_2SO_4$) and concentrated. After purification over silica gel (ratio crude:silica 1/150, eluent:CE:$Et_2O$ 95.5) 315 mg of a colorless oil (46% yield) were obtained. $^1H$ NMR (400 MHz, $CDCl_3$) δ 6.28 (d, J=1.6 Hz, 1H), 6.10 (d, J=1.6 Hz, 1H), 5.46-5.39 (m, 1H), 4.78 (s, 1H), 3.20 (dd, J=4.5, 16.0 Hz, 1H), 2.70 (td, J=4.7, 10.8 Hz, 1H), 2.44 (td, J=2.3, 7.4 Hz, 2H), 2.21-2.10 (m, 1H), 1.92-1.76 (m, 3H), 1.70 (s, 3H), 1.63-1.52 (m, 2H), 1.38 (s, 3H), 1.30 (tt, J=4.3, 9.4, 11.8 Hz, 8H), 1.11 (s, 3H), 0.88 (t, J=7.0 Hz, 3H).

3.4.3 Synthesis of (6aR,10aR)-3-heptyl-9-chloro-6,6,9-trimethyl-6a,7,8,9,10,10a-hexahydro-6H-benzo[c]chromen-1-ol (HCl-THCP)

$ZnCl_2$ 1N in $Et_2O$ (440 μL, 0.44 mmol, 0.5 eq.) was added to a stirred solution of $\Delta^8$-THCP (300 mg, 0.87 mmol, 1 eq.) in 20 mL of anhydrous DCM, at room temperature and under nitrogen atmosphere. After 30 minutes, the reaction was cooled at 0° C. and 2 mL of HCl 4N in dioxane was added. The resulting mixture was stirred at room temperature, overnight and then diluted with diethyl ether. The organic layer was collected and washed, in sequence, with an aqueous saturated solution of $NaHCO_3$ and brine. After dehydration anhydrous $Na_2SO_4$, the organic phase was concentrated to give 305 mg (93% yield) of a yellowish oil, pure enough to be used in the next step without further purification. $^1H$ NMR (400 MHz, $CDCl_3$) δ 6.24 (d, J=1.7 Hz, 1H), 6.07 (d, J=1.6 Hz, 1H), 4.94 (s, 1H), 3.45 (dd, J=2.9, 14.4 Hz, 1H), 3.05 (td, J=2.9, 11.3 Hz, 1H), 2.42 (td, J=1.5, 7.4 Hz, 2H), 2.20-2.12 (m, 1H), 1.80-1.71 (m, 1H), 1.66 (s, 4H), 1.60-1.51 (m, 2H), 1.49-1.42 (m, 1H), 1.38 (s, 3H), 1.34-1.18 (m, 10H), 1.13 (s, 3H), 0.87 (t, J=6.6 Hz, 3H). ESI–MS m/z $[M+H]^+$ calcd. for $C_{23}H_{36}{}^{35}[Cl]O_2{}^+$: 379.2. Found: 379.4. Calcd. for $C_{23}H_{36}{}^{37}[Cl]O_2{}^+$: 381.2. Found: 381.3.

3.4.4 Synthesis of (6aR,10aR)-3-heptyl-6,6,9-trimethyl-6a,7,8,10a-tetrahydro-6H-benzo[c]chromen-1-ol, (−)-trans-$\Delta^9$-THCP HCl-THCP (305 mg, 0.82 mmol, 1 eq.) was solubilized in 10 mL of anhydrous toluene and cooled at −15° C. 1.75 N potassium t-amilate in toluene (1.17 mL, 2.05 mmol, 2.5 eq.) was added dropwise with a syringe to the first solution under a positive pressure of argon. The mixture was stirred in the same condition for 15 minutes and then at 60° C. for 1 h. After cooling at room temperature, the reaction was quenched with a 1% solution of ascorbic acid and diluted with diethyl ether. The organic layer was washed with brine, dried over anhydrous $Na_2SO_4$ and concentrated. The residue was chromatographed (ratio crude/silica 1:300, hexane:i-propyl ether 9.1) to give 232 mg of a greenish oil (83% yield). 50 mg of (−)-trans-$\Delta^9$-THCP were further purified by semipreparative HPLC to prepare a pure analytic standard (purity>99.9%). $^1H$ NMR (600 MHz, $CDCl_3$) δ 6.30 (t, J=2.0 Hz, 1H), 6.27 (d, J=1.6 Hz, 1H), 6.14 (d, J=1.5 Hz, 1H), 4.75 (s, 1H), 3.20 (dt, J=2.5, 10.8 Hz, 1H), 2.43 (dd, J=6.4, 8.9 Hz, 2H), 2.22-2.11 (m, 2H), 1.97-1.87 (m, 1H), 1.69-1.65 (m, 4H), 1.58-1.50 (m, 2H), 1.43-1.37 (m, 4H), 1.34-1.21 (m, 8H), 1.09 (s, 3H), 0.87 (t, J=6.6 Hz, 3H). $^{13}C$ NMR (151 MHz, $CDCl_3$) δ 154.97, 154.34, 143.02, 134.59, 123.92, 110.30, 109.22, 107.72, 77.38, 46.01, 35.72, 33.78, 31.99, 31.37, 31.16, 29.50, 29.38, 27.77, 25.22, 23.55, 22.87, 19.47, 14.29. HRMS m/z $[M+H]^+$ calcd. for $C_{23}H_{35}O_2{}^+$: 343.2632. Found: 343.2633; $[M-H]^-$ calcd. for $C_{23}H_{33}O_2{}^-$: 341.2475. Found: 341.2481. $[\alpha]_D{}^{20}$=−166° (c 1.0, ACN).

3.5 BINDING AT $CB_1$ AND $CB_2$ RECEPTORS

The binding affinity of (−)-trans-$\Delta^9$-THCP against human $CB_1$ and $CB_2$ receptors was assessed by Eurofins Discovery using a radioligand binding assay. Ten concentrations of the phytocannabinoid from 1 nM to 30 μM were tested in duplicate. [$^3$H]CP55940 (at 2 nM, $K_d$=2.4 nM) and [$^3$H] WIN 55212-2 (at 0.8 nM, $K_d$=1.5 nM) were used as specific radioligand for hCB1 and $hCB_2$, respectively[49,50]. Eq. 1 was employed to calculate the percent inhibition of control specific binding obtained in the presence of the tested compounds.

$$\%\ in = 100 - \left(\frac{\text{measured specific binding}}{\text{control specific binding}} * 100\right) \qquad \text{eq. 1}$$

A non-linear regression analysis of the competition curves generated with mean replicate values (eq. 2) was used to calculate the $IC_{50}$ values (concentration causing a half-maximal inhibition of control specific binding)[51].

$$Y = D + \left[\frac{A - D}{1 + \left(\frac{C}{C_{50}}\right)^{nH}}\right] \qquad \text{eq. 2}$$

Where Y is the specific binding, A is the left asymptote of the curve, D is the right asymptote f the curve, C is the compound concentration, $C_{50}$ is the $IC_{50}$ value and nH is the slope factor. This analysis was carried out using a software developed at Cerep (Hill software) and validated by comparing the data with that generated by the commercial software SigmaPlot® 4.0 for Windows® (© 1997 by SPSS Inc.). The inhibition constants ($K_i$) were determined using the Cheng Prusoff equation (eq. 3):

$$Ki = \frac{IC_{50}}{\left(1 + \frac{L}{K_D}\right)} \qquad \text{eq. 3}$$

where L is the concentration of the radioligand, and $K_D$ is the affinity of the radioligand for the receptor.

The data obtained for CP 55940 ($CB_1$ $IC_{50}$=1.7 nM, $CB_1$ $K_i$=0.93 nM) and WIN 55212-2 ($CB_2$ $IC_{50}$=2.7 nM, $CB_2$ $K_i$=1.7 nM) were in accordance with the values reported in literature[49,50].

Docking simulation. The prediction of the binding mode of THCB in complex with human $CB_1$ receptor was performed using Maestro 10.3 of the Schrödinger Suite[52]. The crystallographic structure of the active conformation of $CB_1$ in complex with AM11542 (PDB ID: 5XRA) was downloaded from the Protein Data Bank and was used as reference for docking calculation. The protein was prepared using the Protein Preparation Wizard module[53]. The protonation and tautomeric states of the residues were adjusted at pH 7.0, water molecules were removed, and the hydrogens position was minimized with the OPLS_2005 force field. The chemical structure of (−)-trans-$\Delta^9$-THCP were sketched with ChemDraw 12.0 and converted from 2D to 3D with the LigPrep utility[54]. Five conformations per ligand were initially generated, and appropriate ionization state and tautomers were evaluated for each conformation at physiological pH[55,56]. Afterwards, ligand conformations were minimized with the OPLS_2005 force field. Rigid docking was performed in extra precision mode with Glide version 6.8[57].

3.6 TETRAD TEST

Male C57BL6/J mice (7 weeks old; n=5) were treated with $\Delta^9$-THCP (10, 5 and 2.5 mg/kg) or vehicle (1:1:18; ethanol:Kolliphor EL:0.9% saline) by i.p. administration. Mice were evaluated for hypomotility (open field test), hypothermia (body temperature), antinociceptive (hot plate test), and cataleptic (bar test) effects, using the tetrad tests[58]. Statistical analysis was performed using the Kruskall-Wallis test and Dunn's post hoc tests.

Body temperature. The mouse was immobilized and the probe gently inserted for 1 cm into the rectum until stabilization of temperature. Between each mouse the probe was cleaned with 70% ethanol and dried with paper towel.

Openfield. The open field test was used for the evaluation of motor activity. Behavioral assays were performed 30 min after drug (or vehicle) injection. The apparatus was cleaned before each behavioral session by solution of 70% ethanol. Naïve mice were randomly assigned to a treatment group. Behaviors were recorded, stored, and analyzed using an automated behavioral tracking system (Smart v3.0, Panlab Harvard Apparatus). Mice were placed in an OFT arena (l×w×h: 25 cm×25 cm), and ambulatory activity (total distance travelled in centimeter), were recorded for 15 minutes and analyzed.

Bar test. The bar test was used for the evaluation of catalepsy. Bar was a 40 cm in length and 0.4 cm in diameter glass rod, which was horizontally elevated by 5 cm above the surface. Both forelimbs of mice were positioned on the bar and its hind legs on the floor of the cage, ensuring that the mouse was not lying down on the floor. The chronometer was stopped when the mouse descends from the bar (i.e., when the two forepaws touched the floor) or when 10 min have elapsed (i.e., cut-off time). Catalepsy was measured as the time duration each mouse held the elevated bar by both his forelimbs (latency for moving in seconds).

Hot plate. Changes in nociception were evaluated by the hot plate test. On the day of experiment each mouse was placed on a hot plate (Ugo Basiele) at a constant temperature of 52° C. Licking of the hind paws, as well as jumping, were considered as a nociceptive response (NR) and the latency was measured in seconds 85 minutes after drug or vehicle administration. The latency to the NR was recorded and a 30 or 60 s cut-off time was used in order to prevent tissue damage.

3.7 REFERENCES

1 Novack, G. D. Cannabinoids for treatment of glaucoma. *Curr. Opin. Ophthalmol.* 27, 146-150 (2016).
2 Russo, E. B. *Cannabis* and epilepsy: an ancient treatment returns to the fore. *Epilepsy Behav.* 70, 292-297 (2017).
3 Zeremski, T., Kiprovski, B., Sikora, V., Miladinović, J. & Tubić, S. in *III International Congress, "Food Technology, Quality and Safety", 25-27 Oct. 2016, Novi Sad, Serbia. Proceedings.* 10-15 (University of Novi Sad, Institute of Food Technology).
4 Mutje, P., Lopez, A., Vallejos, M., Lopez, J. & Vilaseca, F. Full exploitation of *Cannabis sativa* as reinforcement/filler of thermoplastic composite materials. *Composites Part A: Applied Science and Manufacturing* 38, 369-377 (2007).
5 Westerhuis, W. *Hemp for textiles: plant size matters*, Wageningen University, (2016).
6 Center for Behavioral Health Statistics and Quality. 2015 National Survey on Drug Use and Health: Detailed Tables. (Rockville, MD, 2016).
7 Hanuš, L. O., Meyer, S. M., Muñoz, E., Taglialatela-Scafati, O. & Appendino, G. Phytocannabinoids: a unified critical inventory. *Nat. Prod. Rep.* 33, 1357-1392, doi: 10.1039/C6NP00074F (2016).
8 Schultz, O.-E. & Haffner, G. Zur Frage der Biosynthese der Cannabinole. *Arch. Pharm.* 293, 1-8, doi: 10.1002/ardp.19602930102 (1960).
9 Niesink, R. J. M. & van Laar, M. Does Cannabidiol Protect Against Adverse Psychological Effects of THC? *Frontiers in Psychiatry* 4, doi: 10.3389/fpsyt.2013.00130 (2013).
10 Kajima, M. & Piraux, M. The biogenesis of cannabinoids in *Cannabis sativa. Phytochemistry* 21, 67-69, doi: doi.org/10.1016/0031-9422 (82) 80016-2 (1982).
11 Citti, C. et al. Analysis of impurities of cannabidiol from hemp. Isolation, characterization and synthesis of cannabidibutol, the novel cannabidiol butyl analog. *J. Pharm. Biomed. Anal.* 175, 112752, doi: doi.org/10.1016/1 ipba.2019.06.049 (2019).
12 Linciano, P. et al. Isolation of a high affinity cannabinoid for human CB1 receptor from a medicinal *cannabis* variety: D9-Tetrahydrocannabutol, the butyl homologue of D9-tetrahydrocannabinol. *J. Nat. Prod.* accepted with revisions (2019).
13 Robertson, L. W., Lyle, M. A. & Billets, S. Biotransformation of cannabinoids by *Syncephalastrum racemosum. Biomed. Mass Spectrom.* 2, 266-271, doi: 10.1002/bms.1200020505 (1975).
14 Bow, E. W. & Rimoldi, J. M. The Structure-Function Relationships of Classical Cannabinoids: CB1/CB2 Modulation. *Perspect. Medicin. Chem.* 8, PMC.S32171, doi: 10.4137/pmc.s32171 (2016).
15 Martin, B. R. et al. Manipulation of the Tetrahydrocannabinol Side Chain Delineates Agonists, Partial Agonists, and Antagonists. *J. Pharmacol. Exp. Ther.* 290, 1065-1079 (1999).
16 Citti, C. et al. Chemical and spectroscopic characterization data of 'cannabidibutol', a novel cannabidiol butyl analog. *Data in Brief* 26, 104463, doi: doi.org/10.1016/j.dib.2019.104463 (2019).
17 Citti, C. et al. A Metabolomic Approach Applied to a Liquid Chromatography Coupled to High-Resolution Tandem Mass Spectrometry Method (HPLC-ESI-HRMS/MS): Towards the Comprehensive Evaluation of the Chemical Composition of *Cannabis* Medicinal Extracts. *Phytochemical Analysis* 29, 144-155, doi: 10.1002/pca.2722 (2018).
18 Pellati, F. et al. New Methods for the Comprehensive Analysis of Bioactive Compounds in *Cannabis sativa* L. (hemp). *Molecules* 23, doi: 10.3390/molecules23102639 (2018).
19 Koch, O. G., Marcus, Rudolf; Looft, Jan; Voessing, Tobias. Preparation of mixtures of cannabinoid compounds useful for therapeutic treatment. Germany patent (2015).
20 Kupper, R. J. Cannabinoid active pharmaceutical ingredient for improved dosage forms. (2006).
21 Nikas, S., Thakur, G. & Makriyannis, A. Synthesis of side chain specifically deuterated (−)-Δ9-tetrahydrocannabinols. *Journal of Labelled Compounds and Radiopharmaceuticals* 45, 1065-1076, doi: 10.1002/jlcr.626 (2002).

22 Choi, Y. H. et al. NMR assignments of the major cannabinoids and cannabiflavonoids isolated from flowers of *Cannabis sativa. Phytochem Anal* 15, 345-354, doi: 10.1002/pca. 787 (2004).

23 Mechoulam, R., Braun, P. & Gaoni, Y. Syntheses of.DELTA. 1-tetrahydrocannabinol and related cannabinoids. *J. Am. Chem. Soc.* 94, 6159-6165, doi: 10.1021/ja00772a038 (1972).

24 Jung, S. W., Cho, A. E. & Yu, W. Exploring the Ligand Efficacy of Cannabinoid Receptor 1 (CB1) using Molecular Dynamics Simulations. *Sci. Rep.* 8, 13787-13787, doi: 10.1038/s41598-018-31749-z (2018).

25 Hua, T. et al. Crystal structures of agonist-bound human cannabinoid receptor CB1. *Nature* 547, 468-471, doi: 10.1038/nature23272 (2017).

26 Shao, Z. et al. High-resolution crystal structure of the human CB1 cannabinoid receptor. *Nature* 540, 602-606, doi: 10.1038/nature20613 (2016).

27 Nikas, S. P. et al. Novel 1',1'-Chain Substituted Hexahydrocannabinols: 9β-Hydroxy-3-(1-hexyl-cyclobut-1-yl)-hexahydrocannabinol (AM2389) a Highly Potent Cannabinoid Receptor 1 (CB1) Agonist. *J. Med. Chem.* 53, 6996-7010, doi: 10.1021/jm100641g (2010).

28 Papahatjis, D. P. et al. Pharmacophoric Requirements for the Cannabinoid Side Chain. Probing the Cannabinoid Receptor Subsite at C1'. *J. Med. Chem.* 46, 3221-3229, doi: 10.1021/jm020558c (2003).

29 Huffman, J. W. et al. Structure-activity relationships for 1', 1'-dimethylalkyl-Δ8-tetrahydrocannabinols. *Bioorg. Med. Chem.* 11, 1397-1410, doi: doi.org/10.1016/S0968-0896 (02) 00649-1 (2003).

30 Nikas, S. P. et al. The role of halogen substitution in classical cannabinoids: a CB1 pharmacophore model. *AAPS J* 6, e30-e30, doi: 10.1208/aapsj060430 (2004).

31 Papahatjis, D. P., Nikas, S. P., Andreou, T. & Makriyannis, A. Novel 1',1'-chain 31 substituted Δ8-tetrahydrocannabinols. *Bioorg. Med. Chem. Lett.* 12, 3583-3586, doi: doi.org/10.1016/S0960-894X (02) 00785-0 (2002).

32 Varvel, S. A. et al. Δ9-tetrahydrocannbinol accounts for the antinociceptive, hypothermic, and cataleptic effects of marijuana in mice. *J. Pharmacol. Exp. Ther.* 314, 329-337 (2005).

33 Citti, C. et al. Cannabinoid Profiling of Hemp Seed Oil by Liquid Chromatography Coupled to High-Resolution Mass Spectrometry. *Frontiers in Plant Science* 10, doi: 10.3389/fpls.2019.00120 (2019).

34 Pavlovic, R. et al. Phytochemical and Ecological Analysis of Two Varieties of Hemp (*Cannabis sativa* L.) Grown in a Mountain Environment of Italian Alps. *Frontiers in Plant Science* 10, doi: 10.3389/fpls.2019.01265 (2019).

35 Citti, C., Pacchetti, B., Vandelli, M. A., Forni, F. & Cannazza, G. Analysis of cannabinoids in commercial hemp seed oil and decarboxylation kinetics studies of cannabidiolic acid (CBDA). *J. Pharm. Biomed. Anal.* 149, 532-540, doi: doi.org/10.1016/j.jpba.2017.11.044 (2018).

36 Citti, C. et al. Untargeted rat brain metabolomics after oral administration of a single high dose of cannabidiol. *J. Pharm. Biomed. Anal.* 161, 1-11, doi: doi.org/10.1016/j.jpba.2018.08.021(2018).

37 Palazzoli, F. et al. Development of a simple and sensitive liquid chromatography triple quadrupole mass spectrometry (LC-MS/MS) method for the determination of cannabidiol (CBD), Δ9-tetrahydrocannabinol (THC) and its metabolites in rat whole blood after oral administration of a single high dose of CBD. *J. Pharm. Biomed. Anal.* 150, 25-32, doi: doi.org/10.1016/j.jpba.2017 11.054 (2018).

38 Russo, E. B. Cannabidiol Claims and Misconceptions. *Trends Pharmacol. Sci.* 38, 198-201, doi: doi.org/10.1016/j.tips.2016.12.004 (2017).

39 Carlini, E. The good and the bad effects of (−) trans-delta-9-tetrahydrocannabinol (Δ9-THC) on humans. *Toxicon* 44, 461-467 (2004).

40 Brierley, D. I., Samuels, J., Duncan, M., Whalley, B. J. & Williams, C. M. A cannabigerol-rich *Cannabis sativa* extract, devoid of [INCREMENT] 9-tetrahydrocannabinol, elicits hyperphagia in rats. *Behav. Pharmacol.* 28, 280-284, doi: 10.1097/fbp.0000000000000285 (2017).

41 Hill, T. D. M. et al. Cannabidivarin-rich *cannabis* extracts are anticonvulsant in mouse and rat via a CB1 receptor-independent mechanism. *Br. J. Pharmacol.* 170, 679-692, doi: 10.1111/bph.12321 (2013).

42 de Meijer, E. P. M. & Hammond, K. M. The inheritance of chemical phenotype in *Cannabis sativa* L. (V): regulation of the propyl-/pentyl cannabinoid ratio, completion of a genetic model. *Euphytica* 210, 291-307, doi: 10.1007/s10681-016-1721-3 (2016).

43 Citti, C., Braghiroli, D., Vandelli, M. A. & Cannazza, G. Pharmaceutical and biomedical analysis of cannabinoids: A critical review. *J. Pharm. Biomed. Anal.* 147, 565-579, doi: doi.org/10.1016/j.jpba.2017.06.003 (2018).

44 Wardle, M. C., Marcus, B. A. & de Wit, H. A Preliminary Investigation of Individual Differences in Subjective Responses to D-Amphetamine, Alcohol, and Delta-9-Tetrahydrocannabinol Using a Within-Subjects Randomized Trial. *PLOS One* 10, e0140501, doi: 10.1371/journal.pone.0140501 (2015).

45 Wachtel, S. R., ElSohly, M. A., Ross, S. A., Ambre, J. & de Wit, H. Comparison of the subjective effects of Delta (9)-tetrahydrocannabinol and marijuana in humans. *Psychopharmacology* (*Berl.* ) 161, 331-339, doi: 10.1007/s00213-002-1033-2 (2002).

46 Bedi, G., Cooper, Z. D. & Haney, M. Subjective, cognitive and cardiovascular dose-effect profile of nabilone and dronabinol in marijuana smokers. *Addict. Biol.* 18, 872-881, doi: 10.1111/j.1369-1600.2011.00427.x (2013).

47 Pertwee, R. The diverse CB1 and CB2 receptor pharmacology of three plant cannabinoids: Δ9-tetrahydrocannabinol, cannabidiol and Δ9-tetrahydrocannabivarin. *Br. J. Pharmacol.* 153, 199-215 (2008).

48 Bundesinstitut für Arzneimittel und Medizinprodukte. *Cannabis* Flos. *New text of the German Pharmacopoeia* (2018).

49 Rinaldi-Carmona, M. et al. Characterization of two cloned human CB1 cannabinoid receptor isoforms. *J. Pharmacol. Exp. Ther.* 278, 871-878 (1996).

50 Munro, S., Thomas, K. L. & Abu-Shaar, M. Molecular characterization of a peripheral receptor for cannabinoids. *Nature* 365, 61-65, doi: 10.1038/365061a0 (1993).

51 Ponzoni, L. et al. The cytisine derivatives, CC4 and CC26, reduce nicotine-induced conditioned place preference in zebrafish by acting on heteromeric neuronal nicotinic acetylcholine receptors. *Psychopharmacology* (*Berl.* ) 231, 4681-4693, doi: 10.1007/s00213-014-3619-x (2014).

52 Schrodinger Release 2014-3: Maestro, Schrodinger LLC (New York, NY (USA), 2014).

53 Schrödinger Suite 2014-3: Protein Preparation Wizard; Epik, Schrödinger, LLC (New York, NY (USA), 2014).

54 Schrodinger Release 2014-3: LigPrep, Schrodinger LLC (New York, NY (USA), 2014).

55 Citti, C. et al. 7-Chloro-5-(furan-3-yl)-3-methyl-4H-benzo[e] [1,2,4] thiadiazine 1,1-Dioxide as Positive Allosteric Modulator of α-Amino-3-hydroxy-5-methyl-4-isoxazolepropionic Acid (AMPA) Receptor. The End of the Unsaturated-Inactive Paradigm? *ACS Chem. Neurosci.* 7, 149-160, doi: 10.1021/acschemneuro.5b00257 (2016).

56 Battisti, U. M. et al. 5-Arylbenzothiadiazine Type Compounds as Positive Allosteric Modulators of AMPA/Kainate Receptors. *ACS Med. Chem. Lett.* 3, 25-29, doi: 10.1021/ml200184w (2012).

57 Schrodinger Release 2014-3: Glide (Version6.8), Schrodinger LLC (New York, NY (USA), 2014).

58 Metna-Laurent, M., Mondésir, M., Grel, A., Vallée, M. & Piazza, P. V. Cannabinoid-Induced Tetrad in Mice. *Curr. Protoc. Neurosci.* 80, 9.59. 51-59.59. 10 (2017).

While the present disclosure has been discussed in terms of certain embodiments, it should be appreciated that the present disclosure is not so limited. The embodiments are explained herein by way of example, and there are numerous modifications, variations and other embodiments that may be employed that would still be within the scope of the present disclosure.

What is claimed is:

1. A method to produce cannabinoid compound (−)-trans-(1R,6R)-cannabidibutol (CBDB) of formula (I), (I)

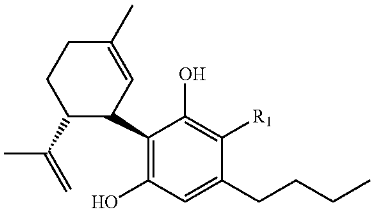

wherein $R_1$ is —H, comprising reacting (1S,4R)-1-methyl-4-(prop-1-en-2-yl)cycloex-2-enol with 5-butylbenzene-1,3-diol according to scheme (I)

Scheme (I)

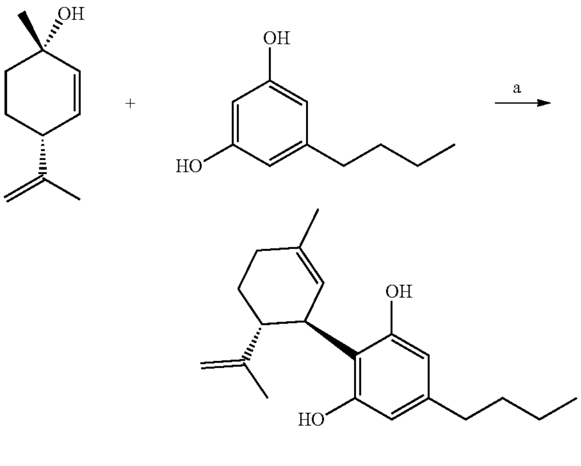

in presence of an acidic catalyst, obtaining CBDB.

2. A method to produce cannabinoid compound (−)-trans-(1R,6R)-cannabidiphorol (CBDP) of formula (IV), (IV)

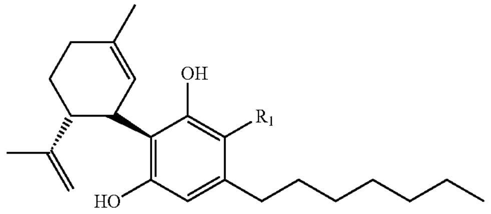

wherein $R_1$ is —H, comprising reacting (1S,4R)-1-methyl-4-(prop-1-en-2-yl)cycloex-2-enol with 5-heptylbenzene-1,3-diol according to scheme (II)

Scheme (II)

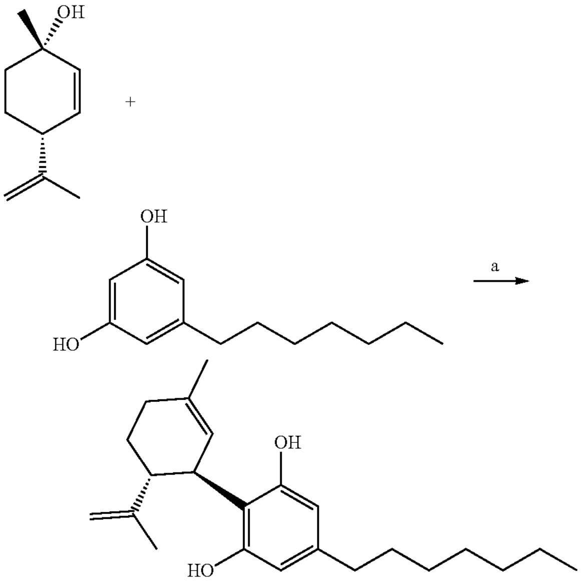

in presence of an acidic catalyst, obtaining CBDP.

3. The method of claim 1, wherein the acidic catalyst is p-toluensulphonic acid.

4. The method of claim 2, wherein the acidic catalyst is p-toluensulphonic acid.

5. The method of claim 1, wherein the reaction is performed under inert atmosphere in a halogenated organic solvent at a temperature of-10±5° C., for a time ranging from 30 to 90 min.

6. The method of claim 2, wherein the reaction is performed under inert atmosphere in a halogenated organic solvent at a temperature of-10±5° C., for a time ranging from 30 to 90 min.

7. A method to produce the cannabinoid compound (−)-trans-(1R,6R)-$\Delta^9$-tetrahydrocannabutol ($\Delta^9$-THCB) of formula (II), (II)

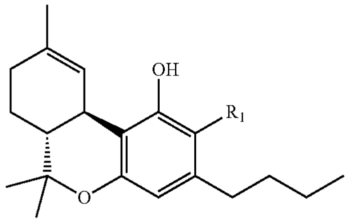

wherein $R_1$ is —H, comprising reacting (−)-trans-(1R,6R)-cannabidibutol (CBDB) of formula (I), (I)

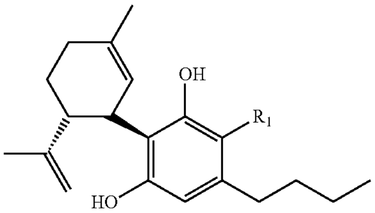

wherein $R_1$ is —H, with hydrochloric acid, obtaining (−)-trans-HCl-THCB of formula (V), (V)

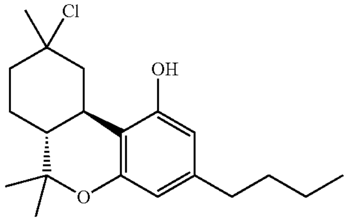

(-)-trans-HCl-THCB followed by treating the compound (V) with a basic compound, obtaining $\Delta^9$-THCB.

8. A method to produce cannabinoid compound (−)-trans-(1R,6R)-$\Delta^9$-tetrahydrocannabiphorol ($\Delta^9$-THCP) of formula (III)

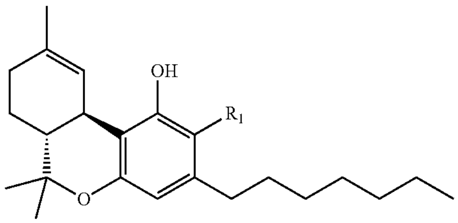

(III), wherein $R_1$ is —H, comprising reacting (−)-trans-(1R,6R)-cannabidiphorol (CBDP) of formula (IV), (IV)

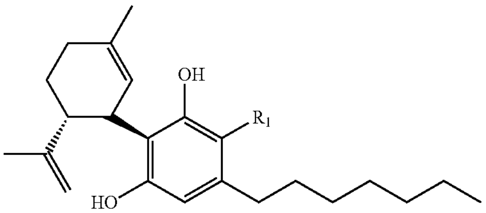

with hydrochloric acid, obtaining (−)-trans-HCl-THCP of formula (VI), (VI)

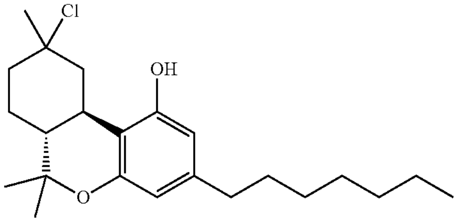

wherein $R_1$ is —H, followed by treating the compound (VI) with a basic compound, obtaining $\Delta^9$-THCP.

9. The method of claim 7, wherein said CBDB is in a mixture with (−)-trans-$\Delta^8$-THCB of formula (VII)

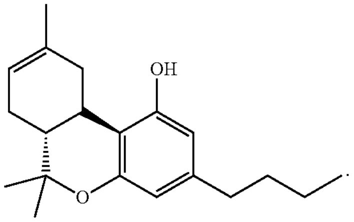

(-)-trans$\Delta^8$-THGB

10. The method of claim 8, wherein said CBDP is in a mixture with (−)-trans-$\Delta^8$-THCP of formula (VIII)

(VIII)

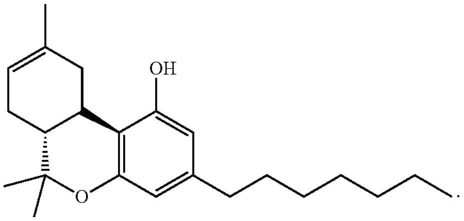

11. The method of claim 7, wherein said basic compound is potassium amylate.

12. The method of claim 8, wherein said basic compound is potassium amylate.

* * * * *